(12) United States Patent
Tsujimoto et al.

(10) Patent No.: US 8,318,781 B2
(45) Date of Patent: Nov. 27, 2012

(54) G-PROTEIN-CONJUGATED RECEPTOR AGONIST

(75) Inventors: Gozoh Tsujimoto, Kyoto (JP); Akira Hirasawa, Kyoto (JP); Naoki Miyata, Nagoya (JP); Takayoshi Suzuki, Nagoya (JP); Yoshiyuki Takahara, Kyoto (JP); Masaji Ishiguro, Takarazuka (JP); Mie Hata, Kyoto (JP)

(73) Assignees: Japan Science and Technology Agency, Saitama (JP); Kyoto University, Kyoto (JP); Nagoya City University, Aichi (JP)

( * ) Notice: Subject to any disclaimer, the term of this patent is extended or adjusted under 35 U.S.C. 154(b) by 214 days.

(21) Appl. No.: 12/597,281

(22) PCT Filed: Apr. 25, 2008

(86) PCT No.: PCT/JP2008/058457
§ 371 (c)(1),
(2), (4) Date: Jan. 29, 2010

(87) PCT Pub. No.: WO2008/139987
PCT Pub. Date: Nov. 20, 2008

(65) Prior Publication Data
US 2011/0184031 A1   Jul. 28, 2011

(30) Foreign Application Priority Data
Apr. 26, 2007   (JP) .................. 2007-116374

(51) Int. Cl.
| | |
|---|---|
| A01N 43/40 | (2006.01) |
| A01N 43/78 | (2006.01) |
| A01N 37/12 | (2006.01) |
| A01N 37/44 | (2006.01) |
| A01N 43/00 | (2006.01) |
| A61K 31/445 | (2006.01) |
| A61K 31/425 | (2006.01) |
| A61K 31/33 | (2006.01) |
| C07D 213/72 | (2006.01) |
| C07D 213/78 | (2006.01) |
| C07D 277/82 | (2006.01) |
| C07C 63/00 | (2006.01) |
| C07C 65/00 | (2006.01) |

(52) U.S. Cl. ........ 514/352; 514/370; 514/567; 514/183; 546/312; 548/161; 562/405

(58) Field of Classification Search ........... None
See application file for complete search history.

(56) References Cited

U.S. PATENT DOCUMENTS

| | | | | |
|---|---|---|---|---|
| 4,218,475 | A | 8/1980 | Wagner et al. | 424/319 |
| 4,999,378 | A | 3/1991 | Fujii et al. | 514/567 |
| 2005/0089866 | A1 | 4/2005 | Hinuma et al. | 435/6 |
| 2006/0258722 | A1 | 11/2006 | Yasuma et al. | 514/367 |
| 2008/0160033 | A1 | 7/2008 | Ito et al. | 424/172.1 |
| 2008/0269220 | A1 | 10/2008 | Yasuma et al. | 514/237.5 |

FOREIGN PATENT DOCUMENTS

| | | |
|---|---|---|
| JP | 2005-015358 | 1/2005 |
| JP | 2005-015461 | 1/2005 |
| WO | WO89/03819 | 5/1989 |
| WO | WO00/00611 | 1/2000 |
| WO | WO00/50596 | 8/2000 |
| WO | WO02/067868 | 9/2002 |
| WO | WO03/068959 | 8/2003 |
| WO | WO2004/065960 | 8/2004 |
| WO | WO2005/087710 | 9/2005 |

OTHER PUBLICATIONS

Gotoh et al., "The regulation of adipogenesis through GPR120", Biochemical and Biophysical Research Communications 354 (2007) 591-597.*
Ahrén, B. "GLP-1 and Extra-islet Effects" Hormone and Metabolic Research 2004 36:842-845.
Beglinger, C. and Degan, L. "Fat in the Intestine as a Regulator of Appetite—Role of CCK" Physiology and Behavior 2004 83:617-621.
Benito et al. "Glucagon-Like Peptide-1-(7-36)Amide Increases Pulmonary Surfactant Secretion through a Cyclic Adenosine 3',5'-Monophosphate-Dependent Protein Kinase Mechanism in Rat Type II Pneumocytes" Endocrinology 1998 139(5):2363-2368.
Briscoe et al. "Pharmacological Regulation of Insulin Secretion in MIN6 Cells through the Fatty Acid Receptor GPR40: Identification of Agonist and Antagonist Small Molecules" British Journal of Pharmacology 2006 148:619-628.
Brubaker, P. L. and Drucker, D. J. "Minireview: Glucagon-Like Peptides Regulate Cell Proliferation and Apoptosis in the Pancreas, Gut, and Central Nervous System" Endocrinology 2004 145(6):2653-2659.
Chen et al. "Gastric Phenotypic Abnormality in Cholecystokinin 2 Receptor Null Mice" Pharmacology and Toxicology 2002 91:375-381.

(Continued)

*Primary Examiner* — Jeffrey S. Lundgren
*Assistant Examiner* — William Lee
(74) *Attorney, Agent, or Firm* — Licata & Tyrrell P.C.

(57) ABSTRACT

Disclosed is a novel aralkyl carboxylic acid compound which has an agonistic activity on GPR-120 and/or GPR-40, particularly GPR-120, and is therefore useful as an appetite regulator, an anti-obesity agent, a therapeutic agent for diabetes, a pancreatic beta differentiating cell growth enhancer, a therapeutic agent for metabolic syndrome, a therapeutic agent for a gastrointestinal disease, a therapeutic agent for a neuropathy, a therapeutic agent for a mental disorder, a therapeutic agent for a pulmonary disease, a therapeutic agent for a pituitary hormone secretion disorder or a lipid flavoring/seasoning agent. The aralkyl carboxylic acid compound is represented by the general formula (I). (I) wherein the ring Q represents a pyridyl or the like; $R^1$ represents a $C_{1-6}$ alkyl group or the like; $R^2$ represents a hydrogen atom, a $C_{1-4}$ alkyl group or a $C_{1-4}$ alkoxy group; m and n independently represent an integer of 1 to 5; and X represents an oxygen atom, a sulfur atom or $-NR^3-$ [wherein $R^3$ represents a hydrogen atom or a $C_{1-4}$ alkyl group].

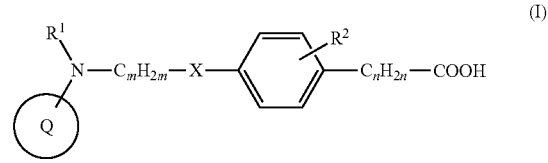

(I)

15 Claims, 8 Drawing Sheets

OTHER PUBLICATIONS

Dhillo, W. S. and Bloom, S. R. "Gastrointestinal Hormones and Regulation of Food Intake" Hormone and Metabolic Research 2004 36:846-851.

Dunning et al. "Alpha Cell Function in Health and Disease: Influence of Glucagon-Like Peptide-1" Diabetologia 2005 48:1700-1713.

Eppstein et al. "Biological Activity of Liposome-Encapsulated Murine Interferon γ is Mediated by a Cell Membrane Receptor" Proceedings of the National Academy of Sciences USA 1985 82:3688-3692.

Garrido et al. "Synthesis and Activity of Small Molecule GPR40 Agonists" Bioorganic and Medicinal Chemistry Letters 2006 16:1840-1845.

Herranz, R. "Cholecystokinin Antagonists: Pharmacological and Therapeutic Potential" Medicinal Research Reviews 2003 23(5):559-605.

Hirasawa et al. "Free Fatty Acids Regulate Gut Incretin Glucagon-Like Peptide-1 Secretion through GPR120" Nature Medicine 2005 11(1):90-94.

Hwang et al. "Hepatic Uptake and Degradation of Unilamellar Sphingomyelin/Cholesterol Liposomes: A Kinetic Study" Proceedings of the National Academy of Sciences USA 1980 77(7):4030-4034.

Kwon et al. "Signaling Elements Involved in the Metabolic Regulation of mTOR by Nutrients, Incretins, and Growth Factors in Islets" Diabetes 2004 53(3):S225-S232.

Lehmann et al. "New Molecular Targets for Treatment of Peptic Ulcer Disease" Drugs 2003 63(17):1785-1797.

Martin, F. J. and Papahadjopoulos, D. "Irreversible Coupling of Immunoglobulin Fragments to Preformed Vesicles" The Journal of Biological Chemistry 1982 257(1):286-288.

McKeown et al. "Solid Phase Synthesis and SAR of Small Molecule Agonists for the GPR40 Receptor" Bioorganic and Medicinal Chemistry Letters 2007 17:1584-1589.

Nyström et al. "Effects of Glucagon-Like Peptide-1 on Endothelial Function in Type 2 Diabetes patients with Stable Coronary Artery Disease" Am J Physiol Endocrinol Metab 2004 287:E1209-E1215.

Owyang, C. and Logsdon, C. D. "New Insights into Neurohormonal Regulation of Pancreatic Secretion" Gastroenterology 2004 127:957-969.

Perry, T. and Greig, N. H. "A New Alzheimer's Disease Interventive Strategy: GLP-1" Current Drug Targets 2004 5:565-571.

Perry, T. and Greig, N. H. "Enhancing Central Nervous System Endogenous GLP-1 Receptor Pathways for Intervention in Alzheimer's Disease" Current Alzheimer Research 2005 2:377-385.

Rehfeld, J. F. "Cholecystokinin" Best Practice and Research Clinical Endocrinology and Metabolism 2004 18(4):569-586.

Small, C. J. and Bloom, S. R. "Gut Hormones and the Control of Appetite" Trends in Endocrinology and Metabolism 2004 15(6):259-263.

Small, C. J. and Bloom, S. R. "Gut Hormones as Peripheral Anti Obesity Targets" Current Drug Targets—CNS and Neurological Disorders 2004 3:379-388.

Thorens, B. "Physiology of GLP-1—Lessons from Glucoincretin Receptor Knockout Mice" Hormone and Metabolic Research 2004 36:766-770.

Tirassa et al. "Cholecystokinin-8 and Nerve Growth Factor: Two Endogenous Molecules Working for the Upkeep and Repair of the Nervous System" Current Drug Targets—CNS and Neurological Disorders 2002 1(5):495-510.

Usui et al. "Design, Synthesis, and Biological Activity of Novel PPARγ Ligands Based on Rosiglitazone and 15d-PGJ$_2$" Bioorganic and Medicinal Chemistry Letters 2005 15:1547-1551.

Usui et al. "Identification of Novel PPARα Ligands by the Structural Modification of a PPARγ Ligand" Bioorganic and Medicinal Chemistry Letters 2006 16:3249-3254.

Vara et al. "Glucagon-Like Peptide-1(7-36) Amide Stimulates Surfactant Secretion in Human Type II Pneumocytes" Am J Respir Crit Care Med 2001 163:840-846.

Varga et al. "Involvement of Endogenous CCK and CCK$_1$ Receptors in Colonic Motor Function" British Journal of Pharmacology 2004 141:1275-1284.

West, S. D. and Mercer, P.W. "Cholecystokinin-Induced Gastroprotection: A Review of Current Protective Mechanisms" Digestive Diseases and Sciences 2004 49(3):361-369.

Winter et al. "Impaired Pancreatic Secretion in Severely Malnourished Patients Is a Consequence of Primary Pancreatic Dysfunction" Nutrition 2001 17:230-235.

Wøjdemann et al. "Inhibition of Human Gastric Lipase Secretion by Glucagon-Like Peptide-1" Digestive Diseases and Sciences 1998 43(4):799-805.

* cited by examiner

1 A

DM　　PMA　　10　　100　　10　　100
　　　　　　　　　LA　　　　　NCG21

1 B

DM　　PMA　　10　　100　　10　　100
　　　　　　　　　LA　　　　　NCG28

1 C

DM　　PMA　　10　　100　　10　　100
　　　　　　　　　LA　　　　　NCG21

1 D

DM　　PMA　　10　　100　　10　　100
　　　　　　　　　LA　　　　　NCG28

5 A

DM　　　PMA　　　10　　100　　10　　100
　　　　　　　　　　　　LA　　　　　NCG21

5 B

DM　　　PMA　　　10　　100　　10　　100
　　　　　　　　　　　　LA　　　　　NCG28

5 C

DM　　　PMA　　　10　　100　　10　　100
　　　　　　　　　　　　LA　　　　　NCG21

5 D

DM　　　PMA　　　10　　100　　10　　100
　　　　　　　　　　　　LA　　　　　NCG28

G-PROTEIN-CONJUGATED RECEPTOR AGONIST

This patent application is a U.S. National Stage Application of International Application No. PCT/JP2008/058457, filed Apr. 25, 2008, which claims the benefit of priority from Japanese Patent Application No. 2007-116374, filed Apr. 26, 2007, teachings of each of which are herein incorporated by reference in their entirety.

TECHNICAL FIELD

The present invention relates to a novel phenyl compound, particularly an aralkylcarboxylic acid compound, having an agonistic activity for GPR120 and/or GPR40. The present invention also relates to an agonistic agent (agonist) for a G protein-coupled (conjugated) receptor (GPCR) comprising said compound or a salt thereof as an active ingredient. The present invention also relates to an appetite suppressant, an obesity inhibitor, a therapeutic agent for diabetes, a differentiation and proliferation enhancer of pancreatic beta cells, a therapeutic agent for metabolic syndrome, a therapeutic for digestive organ diseases, a therapeutic for neurological disorders, a therapeutic for psychological disorders, a therapeutic for lung diseases, a therapeutic for pituitary hormone secretion incompetence, and a fat flavoring, comprising said G protein-coupled receptor (GPCR) agonist as an active ingredient.

BACKGROUND ART

A GPCR is a transmembrane receptor that receives a specific extracellular ligand as a stimulus, transmits the signal to and activates the intracellular G protein. GPCR has a characteristic structure that it penetrates the cell membrane seven times. Upon being bound by a specific ligand, GPCR greatly changes in its structure and thereby activates the G protein.

Among G protein-coupled receptors (GPCR) that binds a fatty acid as a ligand are GPR120 and GPR40 and their analogous molecules, and GPR41 and GPR42 as analogous molecules of GPR40.

A fatty acid receptor GPR120 exists in the intestinal tract, lung, brain, etc., specifically in the intestinal tract, and is known to have 95% identity in amino acid sequence with a G protein-coupled 14273 receptor. It is known that the cells expressing GPR120 in intestinal tract release intestinal hormone peptides, such as glucagon-like peptide (GLP-1) and cholecystokinin (CCK), when it is treated with a fatty acid which functions as an activating ligand of GPR120.

GLUCKSMANN, M. Alexandra, et al. first described 14273 receptor as a novel GPCR, and reported a method for identifying agonists and antagonists by using this GPCR (WO00/00611, WO00/50596).

Further, GIMENO, Ruth et al. reported a method for identifying nucleic acid molecules and polypeptides that are involved in metabolic diseases, and a method for identifying compounds for metabolic diseases that are characterized by the activity of 14273 polypeptide. They also reported that the 14273 receptor could be used for diagnosis, prevention, or treatment of metabolic diseases such as obesity, cibophobia, hyperphagia and diabetes (WO02/067868).

These peptides control the physiological functions involved in feeding. For example, they control the secretion of insulin from pancreatic β cells, the secretion of pancreatic fluid from pancreas, the secretion of bile from gallbladder, and the appetite suppression in the central nervous system. Therefore, an administration of the substance that activates the function of GPR120 to an organisms would be useful for preventing and/or treating diabetes by accelerating the secretion of insulin, for treating incompetent digestive function by promoting the secretion of digestive juice, and for preventing and/or treating obesity by suppressing appetite. Moreover, these peptides are involved in maintenance of nerve cells in the central nervous system. GPR120 exists not only in intestinal tract but also in lung, pituitary gland, adipocyte and tongue, and they play important roles in each organ. They are considered to be involved in secretion of pituitary hormone in pituitary gland, decomposition of fat in adipocyte, gustatory sense in tongue, and lung cell protection in lung.

The present inventors previously analyzed the function of a polypeptide derived from a GPCR gene GT01 (GPR120) and carried out intensive researches to identify compounds that act on the peptide. They unexpectedly found that GT01 polypeptide is distributed on the surface of secreting cells in the human intestine and it has a function of accelerating the secretion of CCK, which functions in feeding control, and identified the compounds which function as the ligand for GT01 polypeptide. More specifically, the present inventors have proposed the compounds for the pharmaceutical composition for treating feeding disorders, and as examples of such compounds, free fatty acids such as capric acid, lauric acid, myristic acid, pentadecanoic acid, palmitic acid, stearic acid, arachic acid, behenic acid, margaric acid, palmitoleic acid, eicosatrienoinic acid, elaidic acid, petroselinic acid, oleinic acid, linolenic acid, γ-linolenic acid, homo-γ-linolenic acid, arachidonic acid, eicosadienoic acid, eicosatrienoic acid, eicosapentanoic acid, docosahexanoic acid, linolic acid, eicosatetraenoic acid, and vaccenic acid (Japanese Patent Laid-open No. 2005-15358).

GPR40 was found in 1997 as an orphan receptor whose ligand was unknown. Later researches revealed that the receptor is expressed in pancreas and its ligand is a fatty acid, and that free fatty acids such as oleic acid and linolenic acid act on GPR40 to promote secretion of insulin from pancreatic β cells. Therefore, it is expected that a compound that acts on GPR40 will function as a preventive or therapeutic drug for diabetes through a novel action mechanism (WO03/068959A1).

On the other hand, Miyata and Suzuki reported that the following compounds have an activity as ligands for PPARγ (Bioorganic & Medicinal Chemistry Letters (2005), 15(6), 1547-1551).

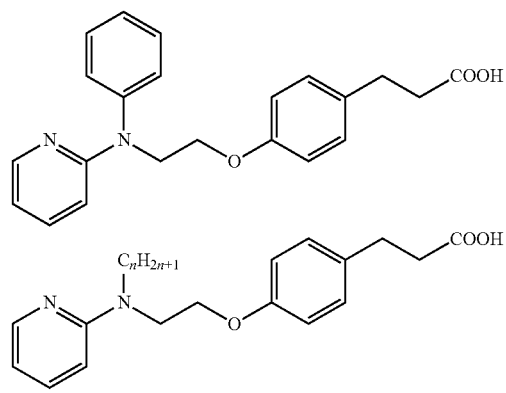

n = 1-6

However, PPARγ is an intranuclear receptor and is basically different from GPCR.

Miyata and Suzuki also reported that the following compound has an activity as ligands for PPARα (Bioorganic & Medicinal Chemistry Letters (2006), 16(12), 3249-3254).

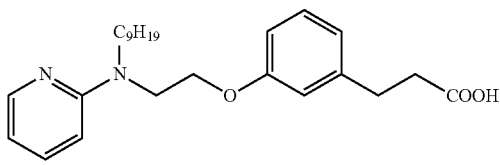

However, PPARα is an intranuclear receptor and is basically different from GPCR.

The following compound (GW9508) is known as an agonist compound for GPR40 and GPR120 (Br J Pharmacol. 2006 July; 148(5) 619-628).

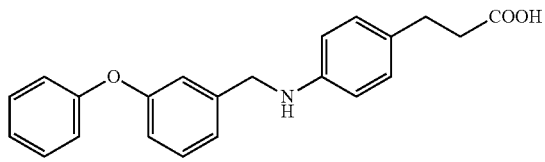

DISCLOSURE OF THE INVENTION

Problem to be Solved by the Invention

Although the in vivo distribution, function and role of GPR120 and GPR40 had been known as mentioned above, no specific agonist compounds for them, especially an agonist compound that can be expected as a medicament for practical use has been proposed yet.

Thus, it is an object of the present invention to propose a compound, which exhibits a good agonistic activity for GPR120 and/or GPR40. It is another object of the present invention to provide a pharmaceutical composition comprising said compound as an active ingredient, especially an agonist, and an appetite suppressant, an obesity inhibitor, a therapeutic for diabetes, a differentiation and proliferation enhancer of pancreatic beta cells, a therapeutic drug for metabolic syndrome, a therapeutic drug for digestive organ disease, a therapeutic drug for neurological disorder, a therapeutic drug for psychological disorder, a therapeutic drug for lung disease, a therapeutic drug for pituitary hormone secretion incompetence, and a fat flavoring comprising said agonist as an active ingredient.

The recent increasing interest in customized medicine has stimulated the research and development of drugs having different mechanisms. Under these circumstances, it is common recognition that one therapeutic drug for diabetes is regarded to be a different medicament from another if their action mechanisms are different. Therefore, the agonist for GRP120 and/or GPR40 according to the present invention is greatly expected as a drug based on a new action mechanism. Particularly, it is expected to be an agonist for GPR120.

Means for Solving the Problem

The present inventors had previously found that, GPR120 is expressed in intestinal tract, lung and brain, and the cells expressing GPR120 in intestinal tract release intestinal tract hormone peptides such as glucagon-like peptide (GLP-1) and cholecystokinin (CCK) upon the activation of GPR120 by a fatty acid. The subsequent investigation based on this finding identified the compounds having an outstanding agonistic activity and thus completed the present invention.

More specifically, the present invention provides a phenyl compound, such as aralkylcarboxylic acid compound, and a salt thereof, having an outstanding agonistic activity for GPR120 and/or GPR40. The present invention also provide a pharmaceutical composition comprising said compound as an active ingredient, particularly an agonist, and an appetite suppressant, an obesity inhibitor, a therapeutic for diabetes, a differentiation and proliferation enhancer of pancreatic beta cells, a therapeutic drug for metabolic syndrome, a therapeutic drug for digestive organ disease, a therapeutic drug for neurological disorder, a therapeutic drug for psychological disorder, a therapeutic drug for lung disease, a therapeutic drug for pituitary hormone secretion incompetence comprising said compound or a pharmaceutically acceptable salt thereof as an active ingredient, as well as a fat flavoring material comprising said compound or a salt thereof as an active ingredient.

The present invention is specifically illustrated in hereinbelow.

1. An agonist for G protein-coupled receptor (GPCR) comprising as an active ingredient a phenyl compound represented by the general formula (i) or a pharmaceutically acceptable salt thereof:

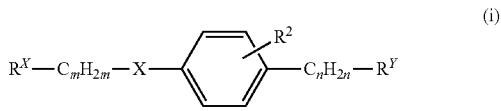

wherein, $R^X$ denotes an aromatic hydrocarbon group, an aromatic heterocyclic group having 1 to 4 heteroatoms (wherein said aromatic hydrocarbon group or aromatic heterocyclic group may be substituted with 1 to 3 substituents), or a substituted amino group represented by the general formula (ii):

wherein:

$R^Y$ denotes a carboxyl group, a 5- or 6-membered aromatic heterocyclic group having 1 to 4 heteroatoms (wherein said aromatic hydrocarbon group or aromatic heterocyclic group may be substituted with 1 to 3 substituents), or a carbamoyl group which may be substituted;

the ring Q denotes an aromatic hydrocarbon group or an aromatic heterocyclic group having 1 to 3 heteroatoms (wherein said aromatic hydrocarbon group or aromatic heterocyclic group may be substituted with 1 to 3 substituents);

$R^1$ denotes a $C_{1-6}$ alkyl group, aromatic hydrocarbon group, or aromatic heterocyclic group having 1 to 3 heteroatoms (wherein said $C_{1-6}$ alkyl group, aromatic hydrocarbon group, or aromatic heterocyclic group may be substituted with 1 to 3 substituents);

$R^2$ denotes a hydrogen atom, $C_{1-4}$ alkyl group, or $C_{1-4}$ alkoxyl group;

X denotes an oxygen atom, a sulfur atom or —NR³— (where R³ denotes a hydrogen atom or a $C_{1-4}$ alkyl group); and m and n are identical or different and each denotes an integer of 1 to 5, provided that when $R^X$ is a phenoxyphenyl group, $R^Y$ is a 5- or 6-membered aromatic heterocyclic group having 1 to 4 heteroatoms (wherein said aromatic hydrocarbon group or aromatic heterocyclic group may be substituted with 1 to 3 substituents) or a carbamoyl group which may be substituted.

2. The phenyl compound as defined in 1 above wherein $R^X$ is a quinolyl group, $R^Y$ is a carboxyl group, teterazolyl group, or alkylsulfonyl-substituted carbamoyl group, X is a nitrogen atom, and $R^2$ is a hydrogen atom; or an agonist for G protein-coupled receptor (GPCR) comprising as an active ingredient the phenyl compound according to 1 above, wherein $R^X$ is a phenoxyphenyl group, $R^Y$ is a teterazolyl group or alkylsulfonyl-substituted carbamoyl group, X is a nitrogen atom, and $R^2$ is a hydrogen atom, or a pharmaceutically acceptable salt thereof.

3. The agonist for G protein-coupled receptor (GPCR) comprising as an active ingredient a phenyl compound or pharmaceutically acceptable salt thereof according to 2 above, selected from the group of compounds shown below.

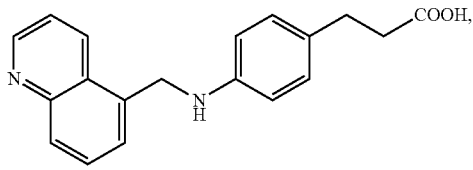
NCG14

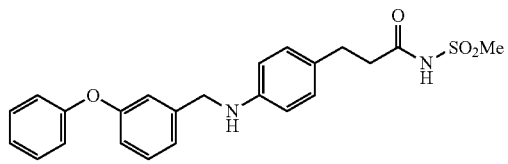
NCG19 and

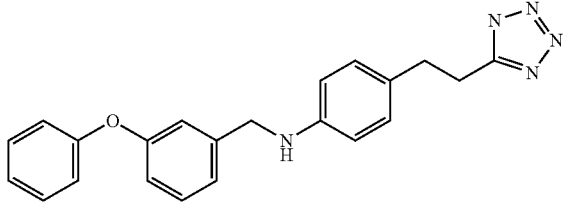
NCG17

4. The agonist for G protein-coupled receptor (GPCR) comprising as an active ingredient a phenyl compound represented by the general formula (i) in 1 above, wherein:

$R^X$ is a substituted amino group represented by the general formula (ii):

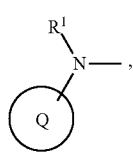
(ii)

and $R^Y$ is a carboxyl group, the phenyl compound is an aralkylcarboxylic acid compound represented by the general formula (I):

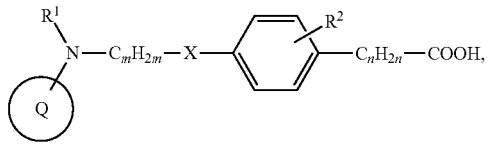
(I)

or pharmaceutically acceptable salt thereof wherein, the ring Q denotes an aromatic hydrocarbon group or an aromatic heterocyclic group having 1 to 3 heteroatoms (wherein said aromatic hydrocarbon group or aromatic heterocyclic group may be substituted with 1 to 3 substituents); $R^1$ denotes a $C_{1-6}$ alkyl group, aromatic hydrocarbon group or an aromatic heterocyclic group having 1 to 3 heteroatoms (wherein said $C_{1-6}$ alkyl group, aromatic hydrocarbon group or aromatic heterocyclic group may be substituted with 1 to 3 substituents); $R^2$ denotes a hydrogen atom, a $C_{1-4}$ alkyl group, or a $C_{1-4}$ alkoxyl group; X denotes an oxygen atom, a sulfur atom, or —NR³— (where R³ denotes a hydrogen atom or a $C_{1-4}$ alkyl group); and m and n are identical or different and each denotes an integer of 1 to 5.

5. The agonist for G protein-coupled receptor (GPCR) comprising as an active ingredient an aralkylcarboxylic acid compound or pharmaceutically acceptable salt thereof according to 4 above, wherein the ring Q is a monocyclic aromatic hydrocarbon group or monocyclic aromatic heterocyclic group having 1 to 3 heteroatoms (wherein said aromatic heterocyclic group may be condensed with a benzene ring, and said aromatic hydrocarbon group or aromatic heterocyclic group may be substituted with 1 to 3 substituents selected from the following group A):

[Group A]
(1) a $C_{1-4}$ alkyl group (which may be substituted with 1 to 3 substituents selected from a halogen atom, a $C_{1-4}$ alkoxyl group, a carboxyl group, a $C_{1-4}$ alkoxycarbonyl group, and an amino group),
(2) a halogen atom,
(3) a $C_{1-4}$ alkoxyl group,
(4) a $C_{1-4}$ alkoxy $C_{1-4}$ alkyl group,
(5) an amino group, and
(6) a hydroxyl group;

$R^1$ is a $C_{1-6}$ alkyl group (which may be substituted with 1 to 3 substituents selected from a halogen atom, a $C_{1-4}$ alkoxyl group, a carboxyl group, a $C_{1-4}$ alkoxycarbonyl group, and an amino group), a monocyclic aromatic hydrocarbon group or a monocyclic aromatic heterocyclic group having 1 to 3 heteroatoms (wherein said aromatic heterocyclic group may be condensed with a benzene ring, and said aromatic hydrocarbon group or aromatic heterocyclic group may be substituted with 1 to 3 substituents selected from the following group B):

[Group B]
(1) $C_{1-4}$ alkyl group (which may be substituted with 1 to 3 substituents selected from a halogen atom, a $C_{1-4}$ alkoxyl group, a carboxyl group, a $C_{1-4}$ alkoxycarbonyl group, and an amino group),
(2) a halogen atom,
(3) a $C_{1-4}$ alkoxyl group,
(4) a $C_{1-4}$ alkoxy $C_{1-4}$ alkyl group,
(5) an amino group, and
(6) a hydroxyl group.

$R^2$ is a hydrogen atom, a $C_{1-4}$ alkyl group, or a $C_{1-4}$ alkoxyl group; X is an oxygen atom, a sulfur atom, or —NH—; and m and n are identical or different integers of 1 to 5.

6. The agonist for G protein-coupled receptor (GPCR) comprising as an active ingredient an aralkylcarboxylic acid compound or pharmaceutically acceptable salt thereof according to 5 above, wherein:

the ring Q is a 5- or 6-membered monocyclic aromatic heterocyclic group having a phenyl group or at least one nitrogen atom (wherein said aromatic heterocyclic group may be condensed with the benzene ring, and said phenyl group or aromatic heterocyclic group may be substituted with 1 to 3 substituents selected from the following group A1):

[Group A1]
(1) $C_{1-4}$ alkyl group (which may be substituted with 1 to 3 substituents selected from a fluorine atom, a chlorine atom, a $C_{1-4}$ alkoxyl group, a carboxyl group, a $C_{1-4}$ alkoxycarbonyl group, and an amino group),
(2) a fluorine atom, a chlorine atom,
(3) a $C_{1-4}$ alkoxyl group,
(4) a $C_{1-4}$ alkoxy $C_{1-4}$ alkyl group,
(5) an amino group, and
(6) a hydroxyl group;

$R^1$ is a $C_{1-6}$ alkyl group (which may be substituted with 1 to 3 substituents selected from a fluorine atom, a chlorine atom, a $C_{1-4}$ alkoxyl group, a carboxyl group, a $C_{1-4}$ alkoxycarbonyl group, and an amino group), a phenyl group or a 5- or 6-membered aromatic heterocyclic group having at least one nitrogen atom (wherein said aromatic hydrocarbon group or aromatic heterocyclic group may be substituted with 1 to 3 substituents selected from the following group B1):

[Group B1]
(1) a $C_{1-4}$ alkyl group (which may be substituted with 1 to 3 substituents selected from a halogen atom, a $C_{1-4}$ alkoxyl group, a carboxyl group, a $C_{1-4}$ alkoxycarbonyl group, and an amino group),
(2) a halogen atom,
(3) a $C_{1-4}$ alkoxyl group,
(4) a $C_{1-4}$ alkoxy $C_{1-4}$ alkyl group,
(5) an amino group, and
(6) a hydroxyl group;

$R^2$ is a hydrogen atom, a $C_{1-4}$ alkyl group or a $C_{1-4}$ alkoxyl group;

X is an oxygen atom, a sulfur atom or —NH—; and
m and n are identical or different integers of 1 to 4.

7. The agonist for G protein-coupled receptor (GPCR) comprising as an active ingredient an aralkylcarboxylic acid compound or pharmaceutically acceptable salt thereof according to 6 above, wherein:

the ring Q is a phenyl group, pyridyl group which may be condensed with a benzene ring, or thiazolyl group which may be condensed with a benzene ring (wherein said phenyl group, pyridyl group, and thiazolyl group may be substituted with 1 or 2 substituents selected from the group consisting of a halogen atom, a hydroxyl group, a $C_{1-4}$ alkoxyl group and an amino group);

$R^1$ is a $C_{1-6}$ alkyl group, a phenyl group, or a pyridyl group (wherein said phenyl group and pyridyl group may be substituted with 1 or 2 substituents selected from the group consisting of a halogen atom, a hydroxyl group, a $C_{1-4}$ alkoxyl group, and an amino group);

$R^2$ is a hydrogen atom;

X is an oxygen atom, sulfur atom or —NH—; and
m and n are identical or different integers of 1 to 4.

8. The agonist for G protein-coupled receptor (GPCR) comprising as an active ingredient an aralkylcarboxylic acid compound or pharmaceutically acceptable salt thereof according to 4 above, wherein the compound is selected from the group of the following compounds.

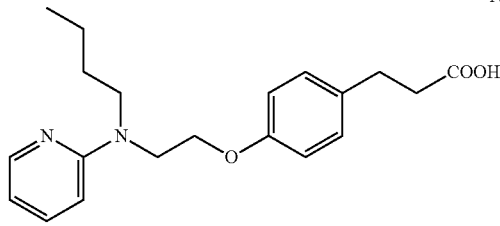

NCP04

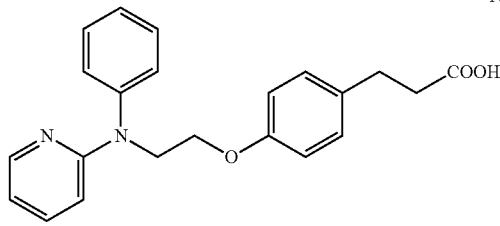

NCP14

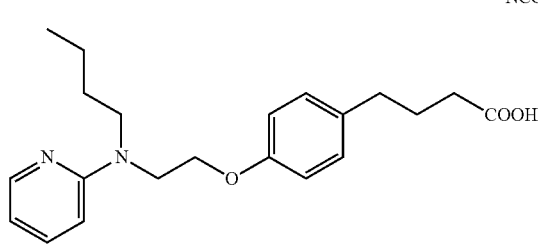

NCG20

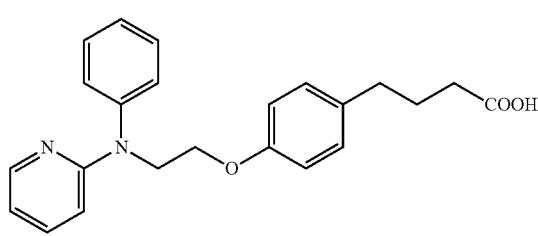

NCG21

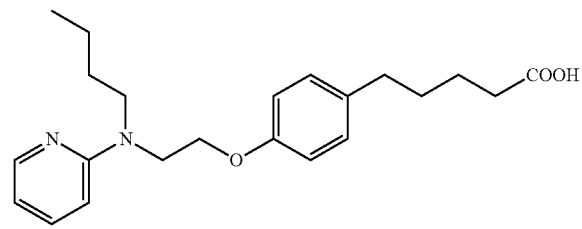

NCG22

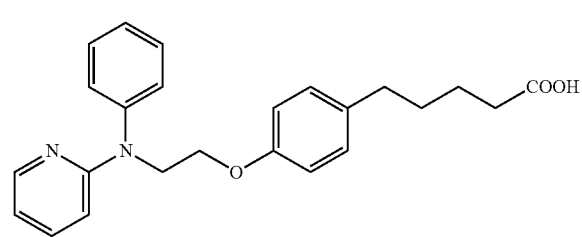

NCG23

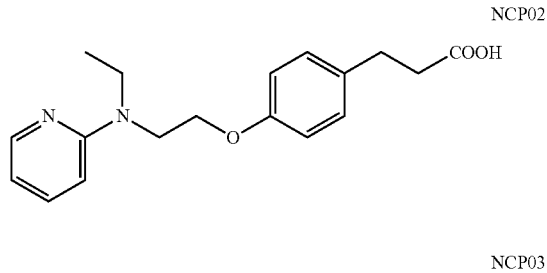
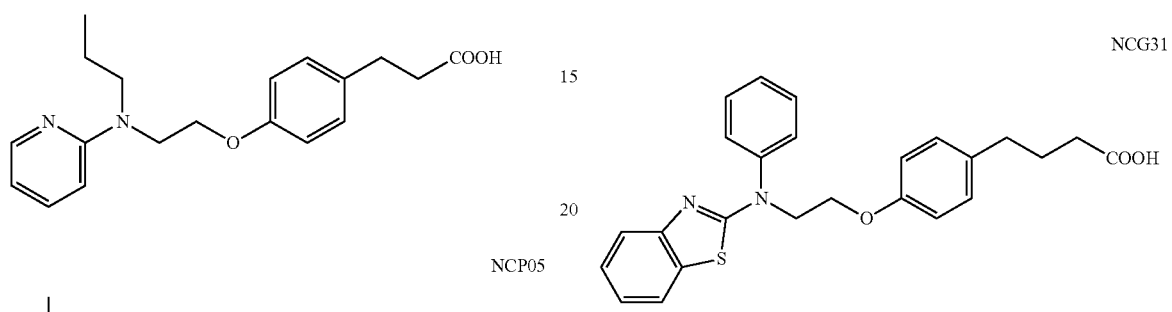
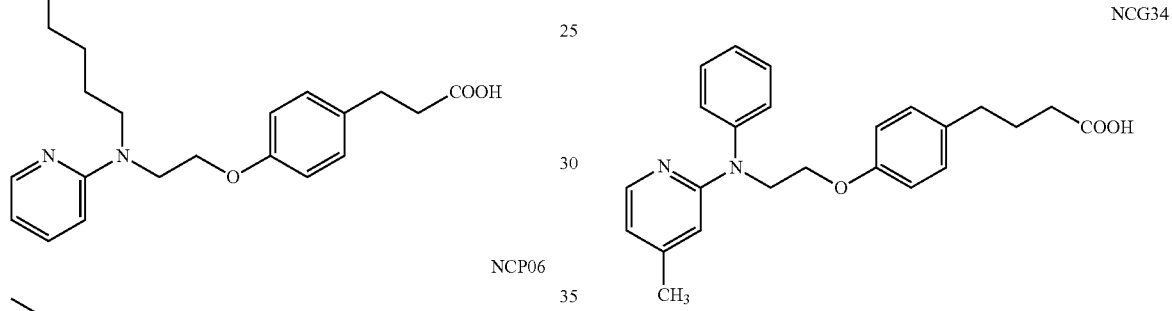
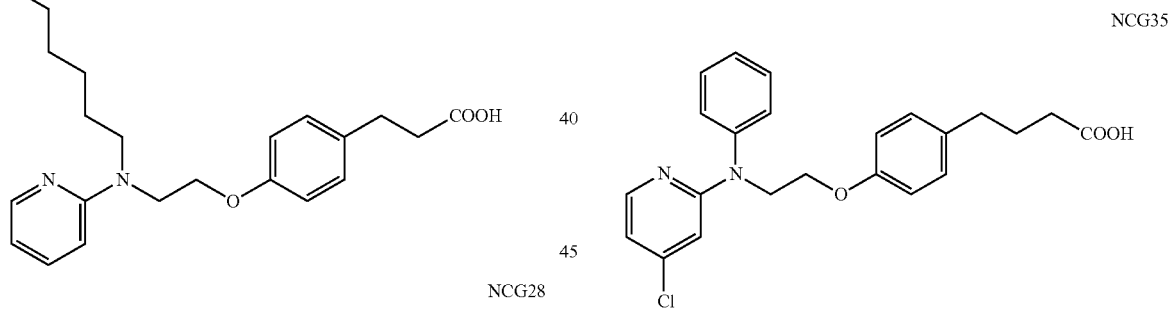
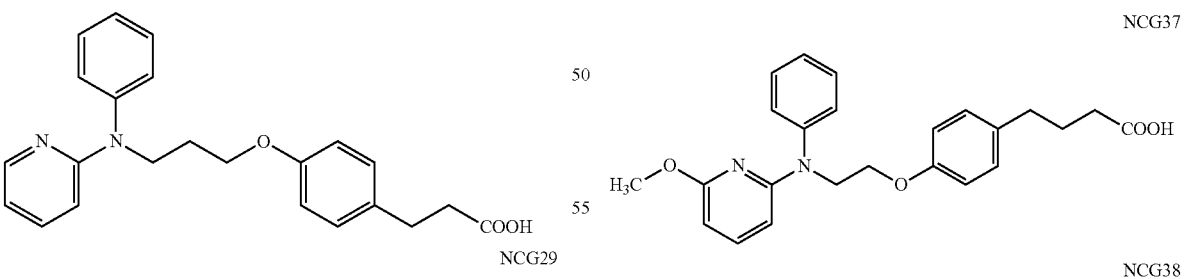
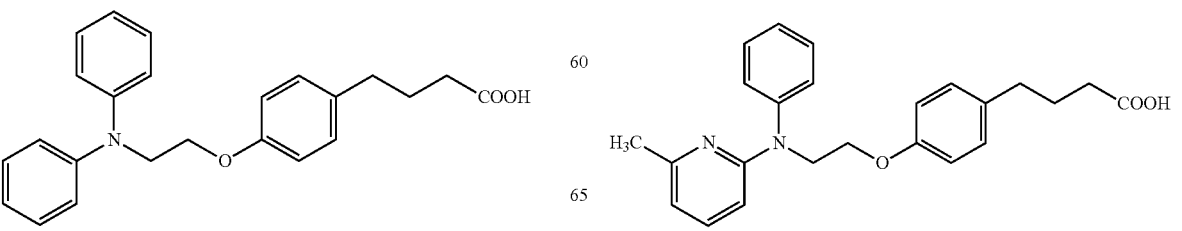

NCG44

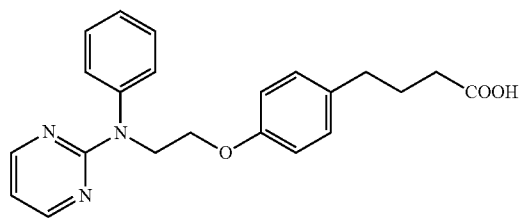

NCG30

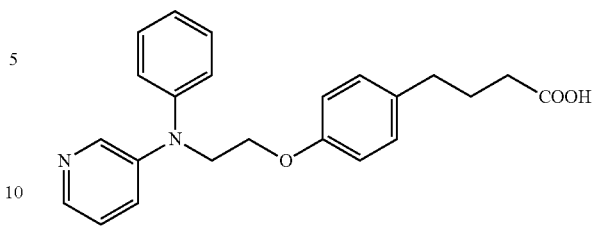

NCG45

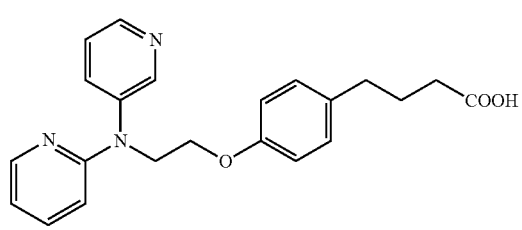

NCG37

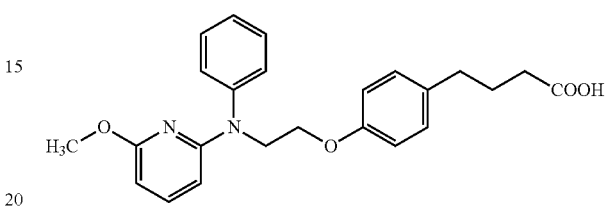

NCG46

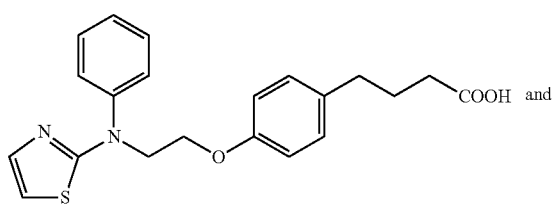 and

NCG46

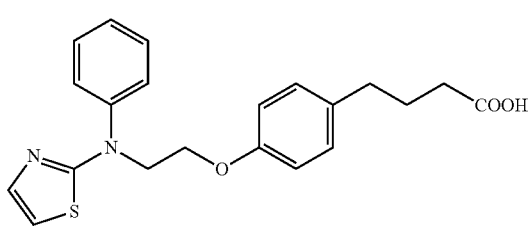

NCG54

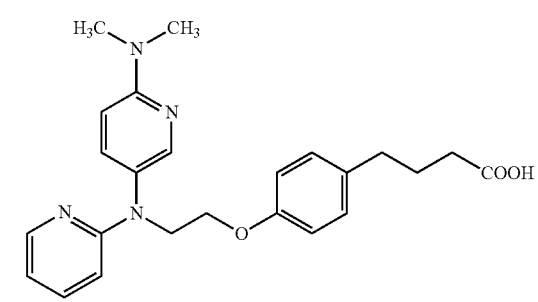

NCG54

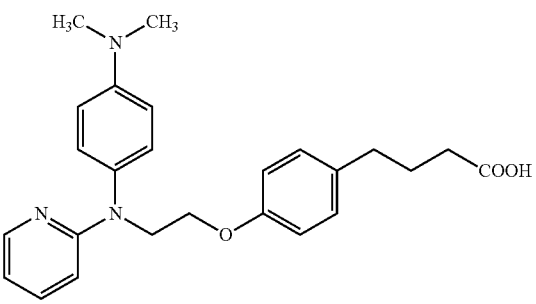

9. The agonist for G protein-coupled receptor (GPCR) comprising as an active ingredient an aralkylcarboxylic acid compound or pharmaceutically acceptable salt thereof according to 8 above, said aralkylcarboxylic acid compound being NCG21, NCG30, NCG37, NCG46, or NCG54 shown below.

NCG21

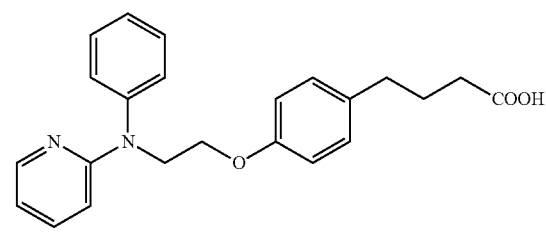

10. The agonist for G protein-coupled receptor (GPCR) according to any of 1 to 9 above, wherein said G protein-coupled receptor (GPCR) is GPR120.

11. The agonist for G protein-coupled receptor (GPCR) according to any of 1 to 9 above, wherein said G protein-coupled receptor (GPCR) is GPR40.

12. A pharmaceutical composition for treatment or prevention of diseases associated with GPR120 and/or GPR40, comprising as an active ingredient an agonist for G protein-coupled receptor (GPCR) according to any of 1 to 11 above.

13. The pharmaceutical composition according to paragraph 12 above, which is an appetite suppressant, an obesity inhibitor, a therapeutic drug for diabetes, a differentiation and proliferation enhancer of pancreatic beta cells, a therapeutic drug for metabolic syndrome, a therapeutic drug for digestive organ diseases, a therapeutic drug for neurological disorders, a therapeutic drug for psychological disorders, a therapeutic drug for lung diseases, or a therapeutic drug for pituitary hormone secretion incompetence.

14. A fat flavoring comprising as an active ingredient an agonist for G protein-coupled receptor (GPCR) according to any of 1 to 11 above.

15. A phenyl compound represented by the general formula (i) in 1 above or a pharmaceutically acceptable salt thereof (in which n is 1, 3, 4, or 5, when the ring Q is a pyridyl group, $R^1$ is a $C_{1-6}$ alkyl group or phenyl group, X is an oxygen atom, $R^2$ is a hydrogen atom, $R^Y$ is a carboxyl group and m is 2; or $R^Y$ is a 5- or 6-membered aromatic heterocyclic group having 1 to 4 heteroatoms (wherein the aromatic hydrocarbon group or aromatic heterocyclic group may be substituted with 1 to 3 substituents) or a carbamoyl group which may be substituted, when $R^X$ is a phenoxyphenyl group)).

16. The phenyl compound represented by the general formula (i) below according to 1 above:

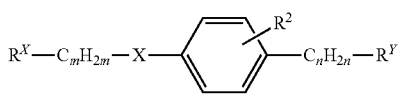

(i)

wherein the compound is the phenyl compound according to claim 14, wherein $R^X$ is a quinolyl group, $R^Y$ is a carboxyl group, a tetrazolyl group or an alkylsulfonyl-substituted carbamoyl group, X is a nitrogen atom, and $R^2$ is a hydrogen atom, or the compound is the phenyl compound or a pharmaceutically acceptable salt thereof according to 15 above, wherein $R^X$ is a phenoxyphenyl group, $R^Y$ is a tetrazolyl group or an alkylsulfonyl-substituted carbamoyl group, X is a nitrogen atom, and $R^2$ is a hydrogen atom.

17. The phenyl compound or a pharmaceutically acceptable salt thereof according to 16 above, which is selected from the group of the compounds shown below.

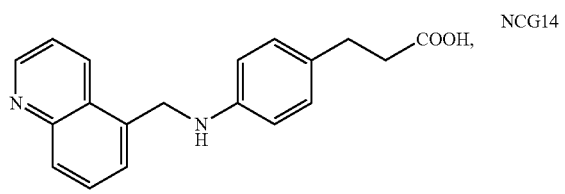

NCG14

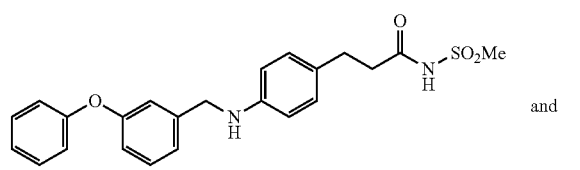

NCG19 and

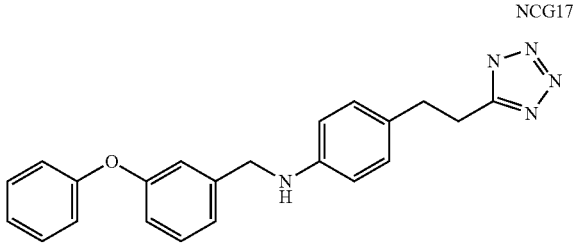

NCG17

18. An aralkylcarboxylic acid compound represented by the general formula (I) below (which has been shown in 4 above):

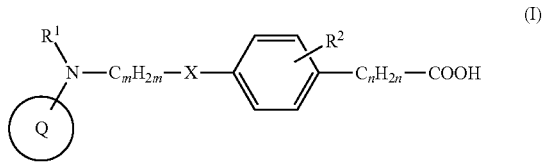

(I)

or a pharmaceutically acceptable salt thereof (in which n is 1, 3, 4, or 5, when the ring Q is a pyridyl group, $R^1$ is a $C_{1-6}$ alkyl group or phenyl group, X is an oxygen atom, $R^2$ is a hydrogen atom and m is 2).

19. The aralkylcarboxylic acid compound or a pharmaceutically acceptable salt thereof according to 18 above, wherein the ring Q is a monocyclic aromatic hydrocarbon group or a monocyclic aromatic heterocyclic group having 1 to 3 heteroatoms (wherein said aromatic heterocyclic group may be condensed with a benzene ring, and said aromatic hydrocarbon group or aromatic heterocyclic group may be substituted with 1 to 3 substituents selected from the following group A):
[Group A]
(1) a $C_{1-4}$ alkyl group (which may be substituted with 1 to 3 substituents selected from a halogen atom, a $C_{1-4}$ alkoxyl group, a carboxyl group, a $C_{1-4}$ alkoxycarbonyl group and an amino group),
(2) a halogen atom,
(3) a $C_{1-4}$ alkoxyl group,
(4) a $C_{1-4}$ alkoxy $C_{1-4}$ alkyl group,
(5) an amino group, and
(6) a hydroxyl group;
$R^1$ is a $C_{1-6}$ alkyl group (which may be substituted with 1 to 3 substituents selected from a halogen atom, a $C_{1-4}$ alkoxyl group, a carboxyl group, a $C_{1-4}$ alkoxycarbonyl group and an amino group) or a monocyclic aromatic hydrocarbon group or a monocyclic aromatic heterocyclic group having 1 to 3 heteroatoms (wherein said aromatic heterocyclic group may be condensed with a benzene ring, and said aromatic hydrocarbon group or aromatic heterocyclic group may be substituted with 1 to 3 substituents selected from the following group B):
[Group B]
(1) a $C_{1-4}$ alkyl group (which may be substituted with 1 to 3 substituents selected from a halogen atom, a $C_{1-4}$ alkoxyl group, a carboxyl group, a $C_{1-4}$ alkoxycarbonyl group, and an amino group),
(2) a halogen atom,
(3) a $C_{1-4}$ alkoxyl group,
(4) a $C_{1-4}$ alkoxy $C_{1-4}$ alkyl group,
(5) an amino group, and
(6) a hydroxyl group;
$R^2$ is a hydrogen atom, a $C_{1-4}$ alkyl group, or a $C_{1-4}$ alkoxyl group; X is an oxygen atom, a sulfur atom or —NH—; and m and n are identical or different integers of 1 to 5 (in which n is 1, 3, 4, or 5, when the ring Q is a pyridyl group, $R^1$ is a $C_{1-6}$ alkyl group or phenyl group, X is an oxygen atom, $R^2$ is a hydrogen atom and m is 2).

20. The aralkylcarboxylic acid compound or a pharmaceutically acceptable salt thereof according to 19 above, wherein:
the ring Q is a phenyl group or a 5- or 6-membered monocyclic aromatic heterocyclic group having at least one nitrogen atom (wherein said aromatic heterocyclic group may be condensed with a benzene ring, and said phenyl group or aromatic heterocyclic group may be substituted with 1 to 3 substituents selected from the following group A1):
[Group A1]

(1) a $C_{1-4}$ alkyl group (which may be substituted with 1 to 3 substituents selected from a fluorine atom, a chlorine atom, a $C_{1-4}$ alkoxyl group, a carboxyl group, a $C_{1-4}$ alkoxycarbonyl group and an amino group), (2) a fluorine atom, a chlorine atom, (3) a $C_{1-4}$ alkoxyl group, (4) a $C_{1-4}$ alkoxy $C_{1-4}$ alkyl group, (5) an amino group, and (6) a hydroxyl group;

$R^1$ is a $C_{1-6}$ alkyl group (which may be substituted with 1 to 3 substituents selected from a fluorine atom, a chlorine atom, a $C_{1-4}$ alkoxyl group, a carboxyl group, a $C_{1-4}$ alkoxycarbonyl group and an amino group), a phenyl group, or a 5- or 6-membered aromatic heterocyclic group having at least one nitrogen atom (said aromatic hydrocarbon group or aromatic heterocyclic group may be substituted with 1 to 3 substituents selected from the following group B1):

[Group B1]

(1) a $C_{1-4}$ alkyl group (which may be substituted with 1 to 3 substituents selected from a halogen atom, a $C_{1-4}$ alkoxyl group, a carboxyl group, a $C_{1-4}$ alkoxycarbonyl group, and an amino group), (2) a halogen atom, (3) a $C_{1-4}$ alkoxyl group, (4) a $C_{1-4}$ alkoxy $C_{1-4}$ alkyl group, (5) an amino group, and (6) a hydroxyl group;

$R^2$ is a hydrogen atom, a $C_{1-4}$ alkyl group or a $C_{1-4}$ alkoxyl group; X is an oxygen atom, a sulfur atom or —NH—; and m and n are identical or different integers of 1 to 4 (wherein n is 1, 3, 4, or 5, when the ring Q is a pyridyl group, $R^1$ is a $C_{1-6}$ alkyl group or phenyl group, X is an oxygen atom, $R^2$ is a hydrogen atom and m is 2).

21. The aralkylcarboxylic acid compound or a pharmaceutically acceptable salt thereof according to 20 above, wherein:

the ring Q is a phenyl group, a pyridyl group which may be condensed with a benzene ring, or a thiazolyl group which may be condensed with a benzene ring (these phenyl group, pyridyl group, and thiazolyl group may be substituted with 1 or 2 substituents selected from the group consisting of a halogen atom, a hydroxyl group, a $C_{1-4}$ alkoxyl group and an amino group);

$R^1$ is a $C_{1-6}$ alkyl group, a phenyl group or pyridyl group (these phenyl group and pyridyl group may be substituted 1 or 2 substituents selected from the group consisting of a halogen atom, a hydroxyl group, a $C_{1-4}$ alkoxyl group and an amino group);

$R^2$ is a hydrogen atom;

X is an oxygen atom, a sulfur atom or —NH—; and m and n are identical or different integers of 1 to 4 (provided that n is 1, 3, 4, or 5, when the ring Q is a pyridyl group, $R^1$ is a $C_{1-6}$ alkyl group or phenyl group, X is an oxygen atom, $R^2$ is a hydrogen atom and m is 2).

22. The aralkylcarboxylic acid compound or a pharmaceutically acceptable salt thereof according to 21 above, which is selected from the group of the following compounds.

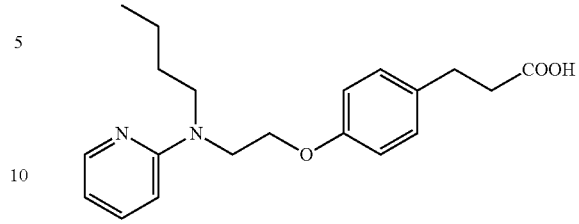

NCP04

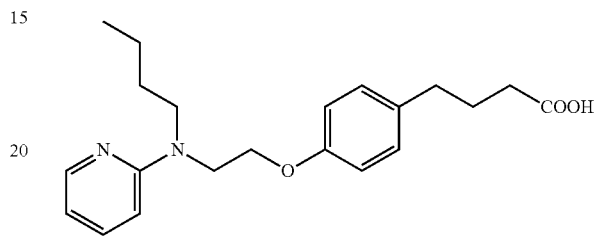

NCG20

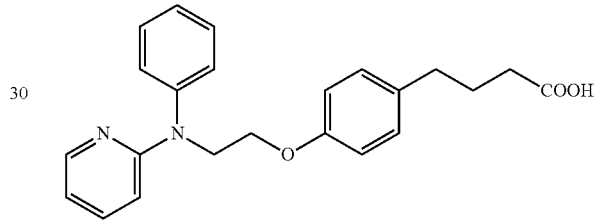

NCG21

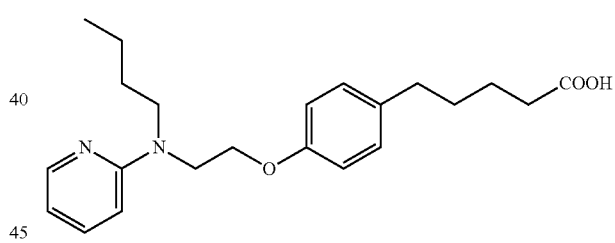

NCG22

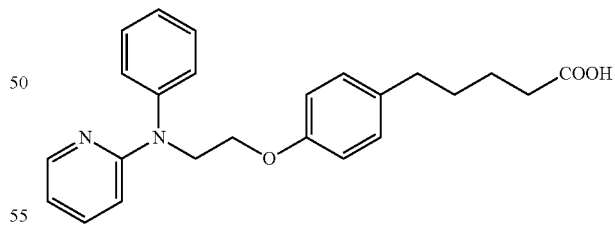

NCG23

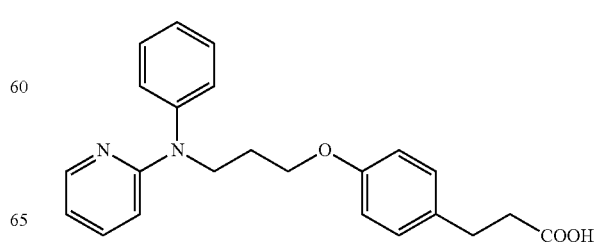

NCG28

NCG29
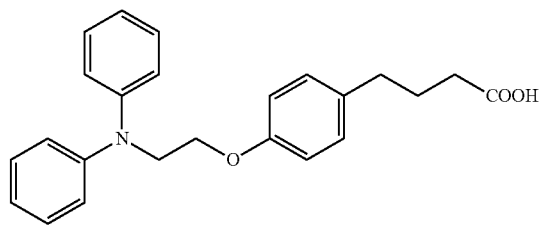
NCG30
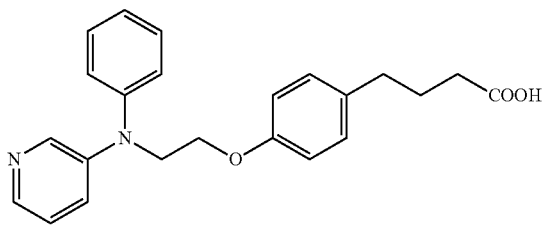
NCG31
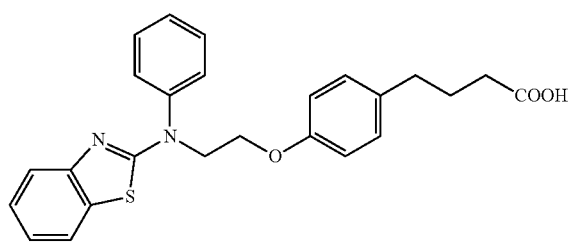
NCG34
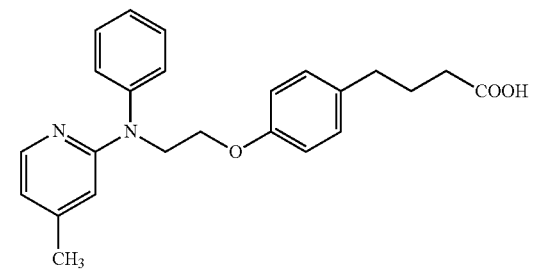
NCG35
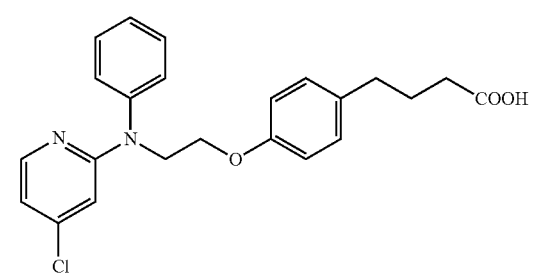
NCG37
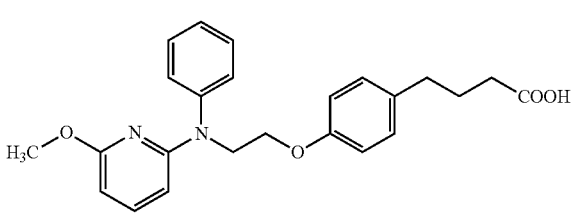
NCG38
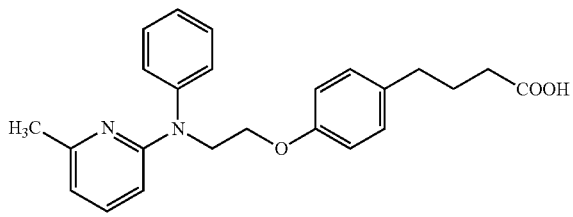
NCG44
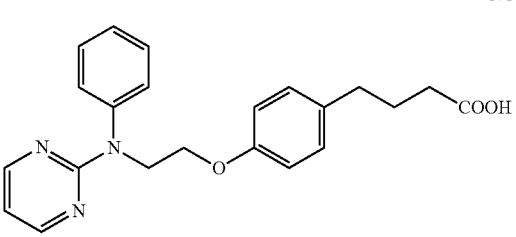
NCG45
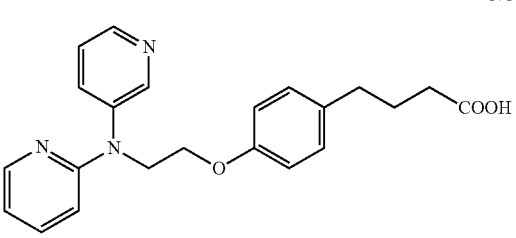
NCG46
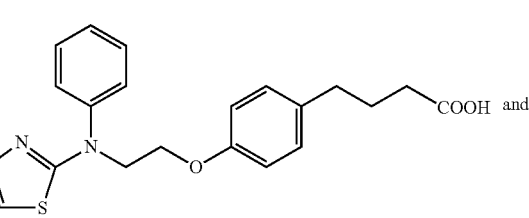 and
NCG54
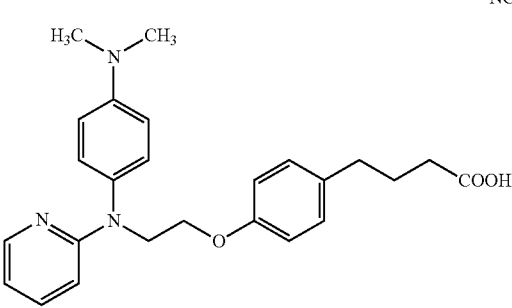
23. The aralkylcarboxylic acid compound or a pharmaceutically acceptable salt thereof according to 22 above, said aralkylcarboxylic acid compound is NCG21, NCG30, NCG37, NCG46, or NCG54 shown below.

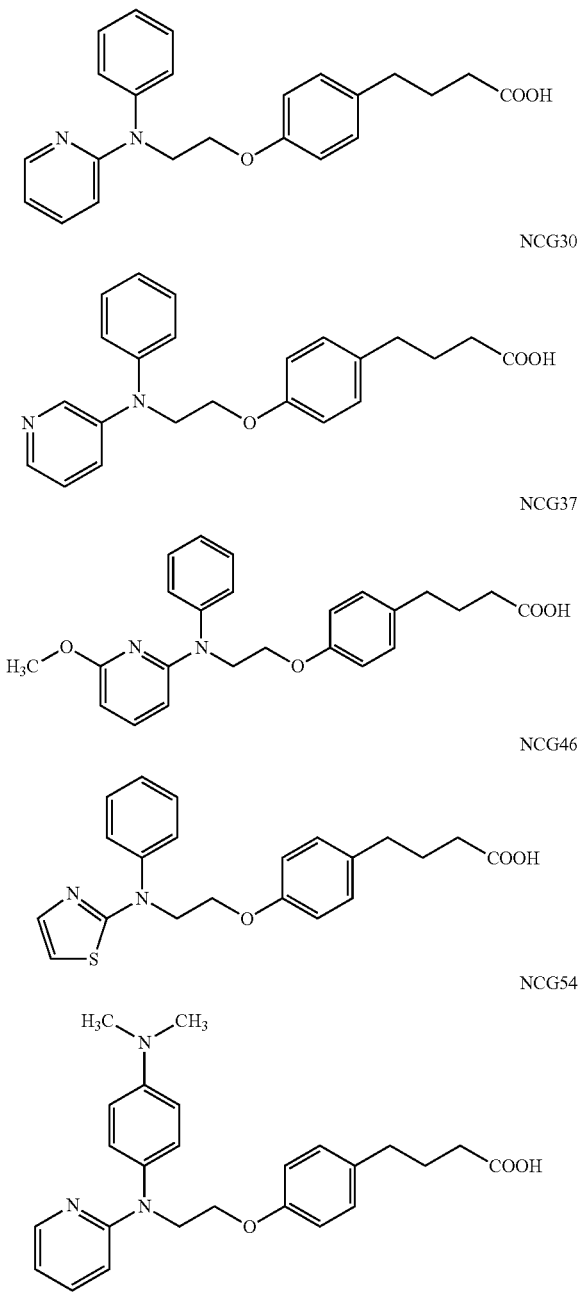

Effect of the Invention

The phenyl compounds, such as aralkylcarboxylic acids, according to the present invention have an outstanding agonistic activity for G protein-coupled receptor (GPCR), particularly GPR120 and/or GPR40. Therefore, the compounds according to the present invention is capable of acting on GPR120, thereby enables the release of the intestinal hormone peptides, such as glucagon-like peptide 1 (GLP-1) and cholecystokinin (CCK). They are useful as an appetite suppressant, an obesity inhibitor, a therapeutic for diabetes, a differentiation and proliferation enhancer of pancreatic beta cells, a therapeutic for metabolic syndrome, a therapeutic drug for digestive organ diseases, a therapeutic drug for neurological disorders, a therapeutic drug for psychological disorders, a therapeutic drug for lung diseases, and a therapeutic drug for pituitary hormone secretion incompetence.

Further, owing to their outstanding agonistic activity for GPR40, the compounds of the present invention are capable of promoting the secretion of insulin from pancreas β cells, and hence expected to be a prophylactic and therapeutic drug for diabetes that works via a new action mechanism.

Accordingly, a pharmaceutical composition comprising as an active ingredient the phenyl compounds, such as aralkylcarboxylic acids, of the present invention, particularly GPCR agonists, more specifically a GPR120 agonist and GPR40 agonist, is expected to be a medicament based on a novel mechanism of action. Specifically, they are effective as an appetite suppressant, an obesity inhibitor, a therapeutic for diabetes, a differentiation and proliferation enhancer of pancreatic beta cells, a therapeutic for metabolic syndrome, a therapeutic drug for digestive organ diseases, a therapeutic drug for neurological disorders, a therapeutic drug for psychological disorders, a therapeutic drug for lung diseases, and a therapeutic drug for pituitary hormone secretion incompetence. Since GPR120 is also involved in gustatory sense, the compound of the present invention would be found a use as a fat flavoring material.

DM denotes DMSO as a negative control, and PMA denotes Phorbol-12-myristate-13-acetate as a positive control. LA denotes cis-α-linolenic acid as a positive object. The compounds tested are NCG21 and NCG28.

1A shows the results of total ERK detection by Western blotting in a cell line TXGPR40 stimulated with NCG21.

1B shows the results of total ERK detection by Western blotting in cell line TXGPR40 stimulated with NCG28.

1C shows the results of phosphorylated ERK detection by Western blotting in cell line TXGPR40 stimulated with NCG21.

1D shows the results of phosphorylated ERK detection by Western blotting in cell line TXGPR40 stimulated with NCG28.

Figure 2:
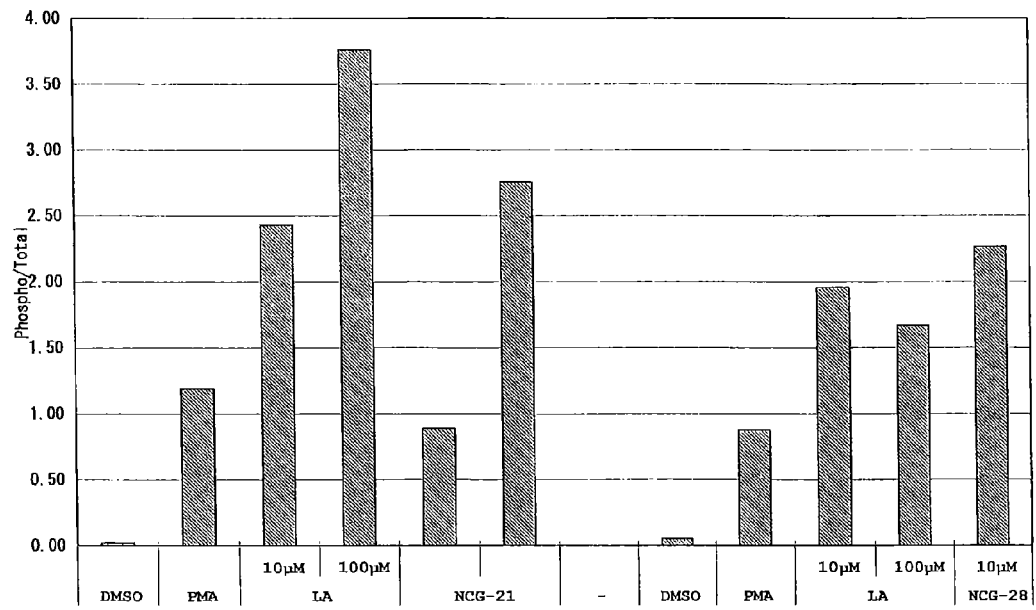

FIG. 2 is a diagram showing the results of the screening for GPR40 ligand by ERK assay in Test Example 1. The vertical axis represents phospho-ERK/total ERK.

Figure 3:
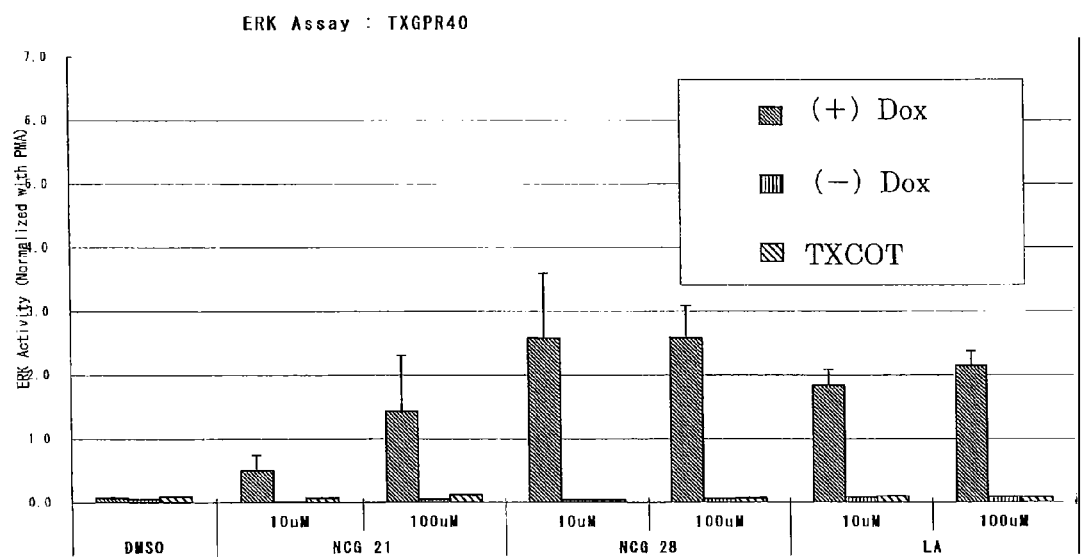

FIG. 3 is a diagram showing the comparison in ERK activity of the compounds (NCG21 and NCG28) using cell line TXGPR40.

Figure 4:
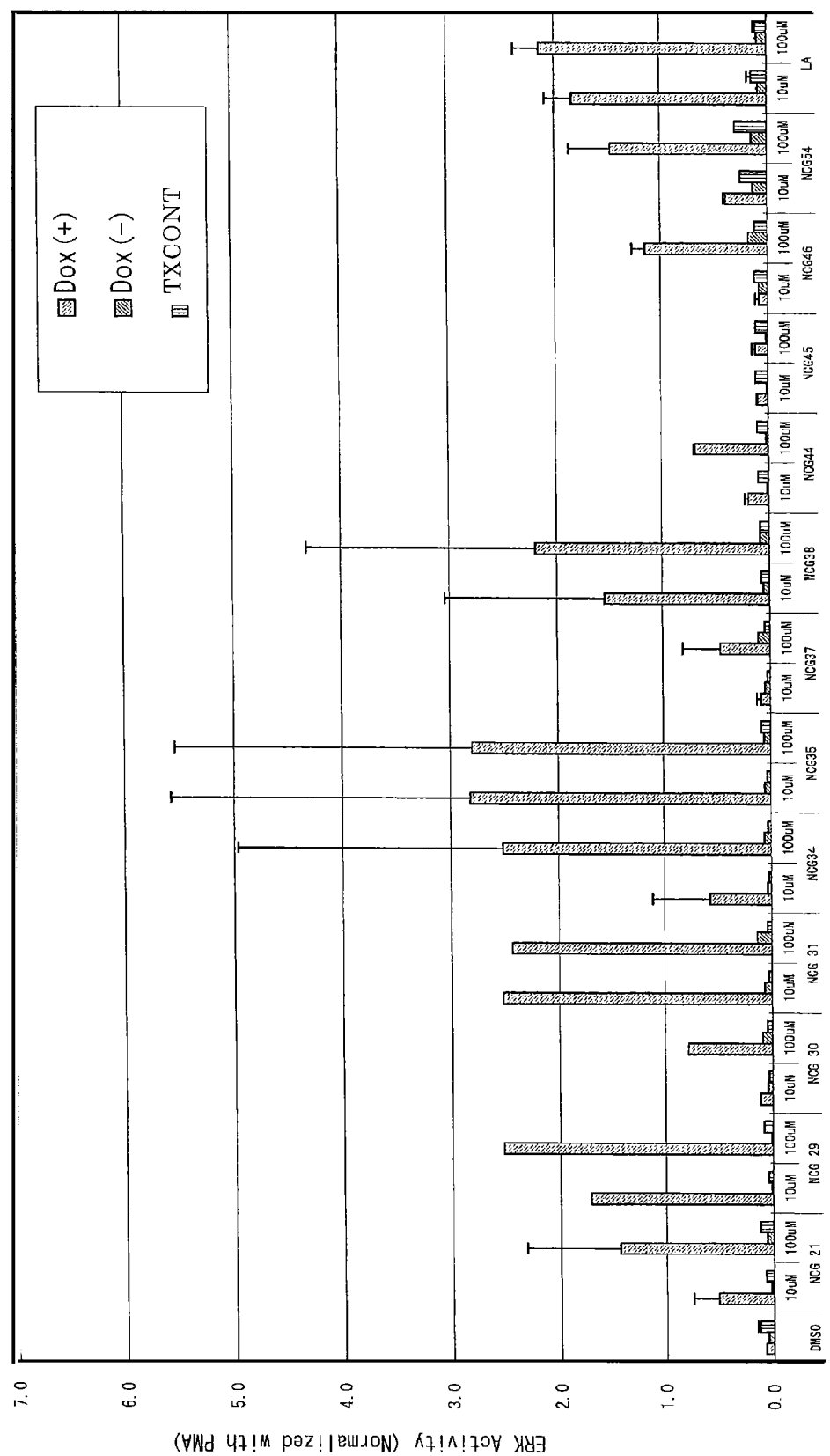

FIG. 4 is a diagram showing the comparison in ERK activity of other compounds of the present invention (NCG29, NCG30, NCG31, NCG34, NCG35, NCG37, NCG38, NCG44, NCG45, NCG46, and NCG54) using cell line TXGPR40.

Figure 5:
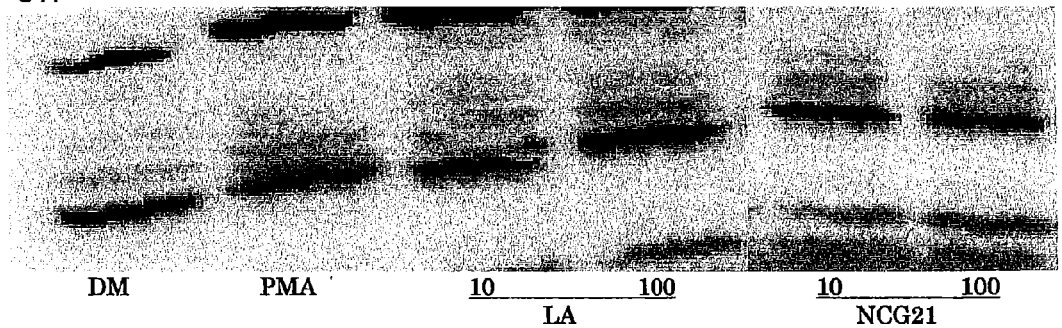
Figure 5:
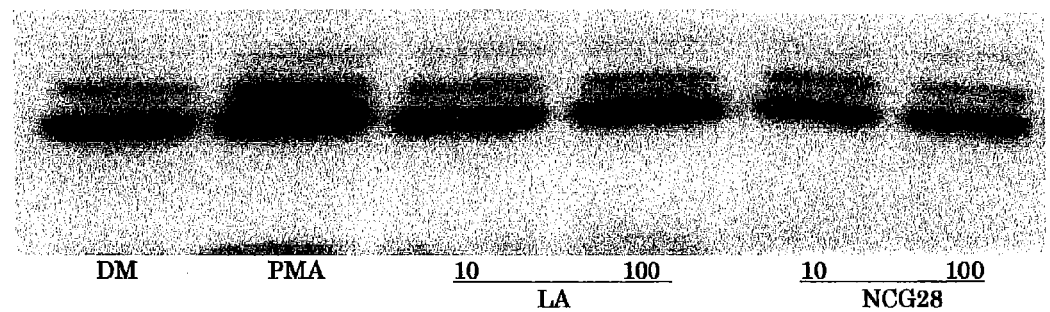
Figure 5:
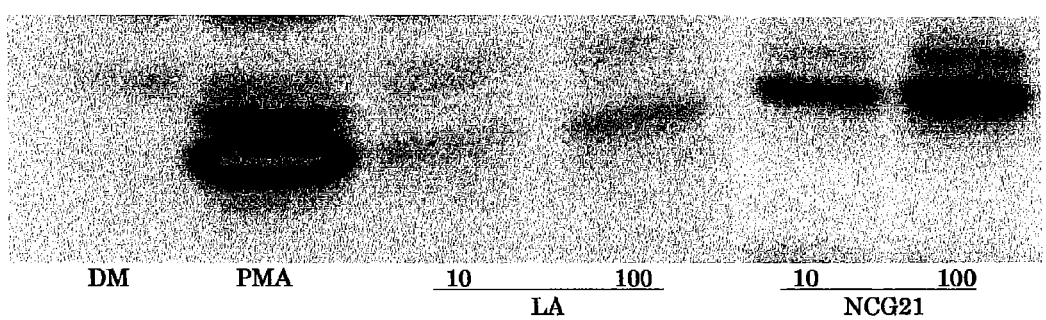
Figure 5:
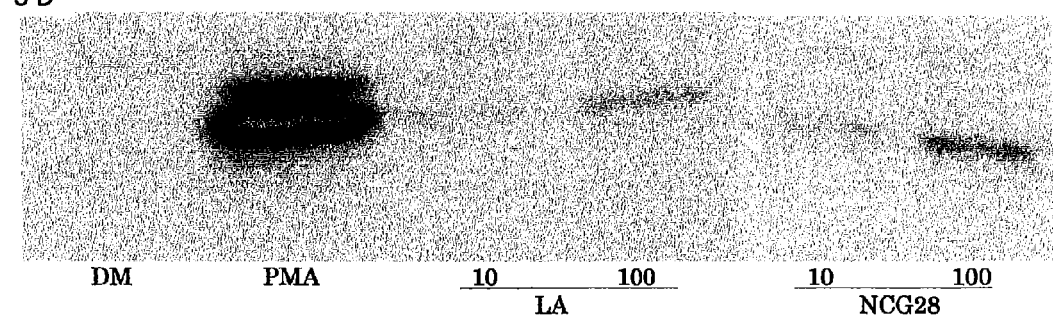

FIG. 5 is a diagram indicating the results of screening for GPR120 ligand by ERK assay in Test Example 1.

Here, DM denotes DMSO as a negative control, and PMA denotes Phorbol-12-myristate-13-acetate as a positive control. LA denotes cis-α-linolenic acid as a positive object. The compounds tested are NCG21 and NCG28.

5A is a diagram showing the results of total ERK detection by Western blotting in cell line TXGPR120 stimulated with NCG21.

5B is a diagram showing the results of total ERK detection by Western blotting in cell line TXGPR120 stimulated with NCG28.

5C is a diagram showing the results of phosphorylated ERK detection by Western blotting in cell line TXGPR120 stimulated with NCG21.

5D is a diagram showing the results of phosphorylated ERK detection by Western in cell line TXGPR120 stimulated with NCG28.

Figure 6:
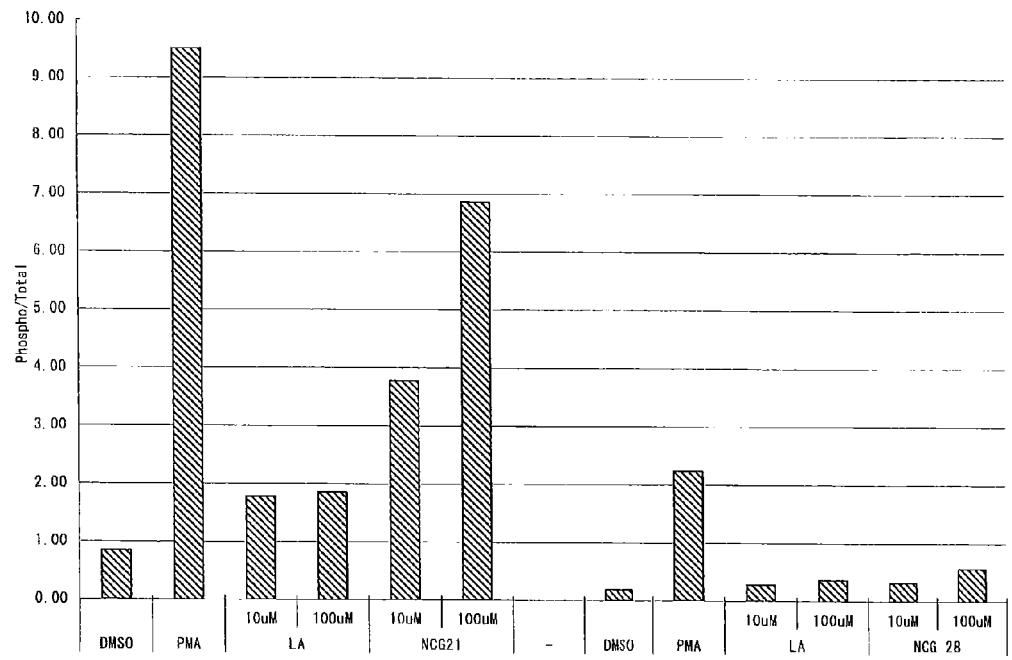

FIG. 6 is a diagram showing the results of screening for GPR120 ligand by ERK assay in Test Example 1. The vertical axis represents phospho-ERK/total ERK.

Figure 7:
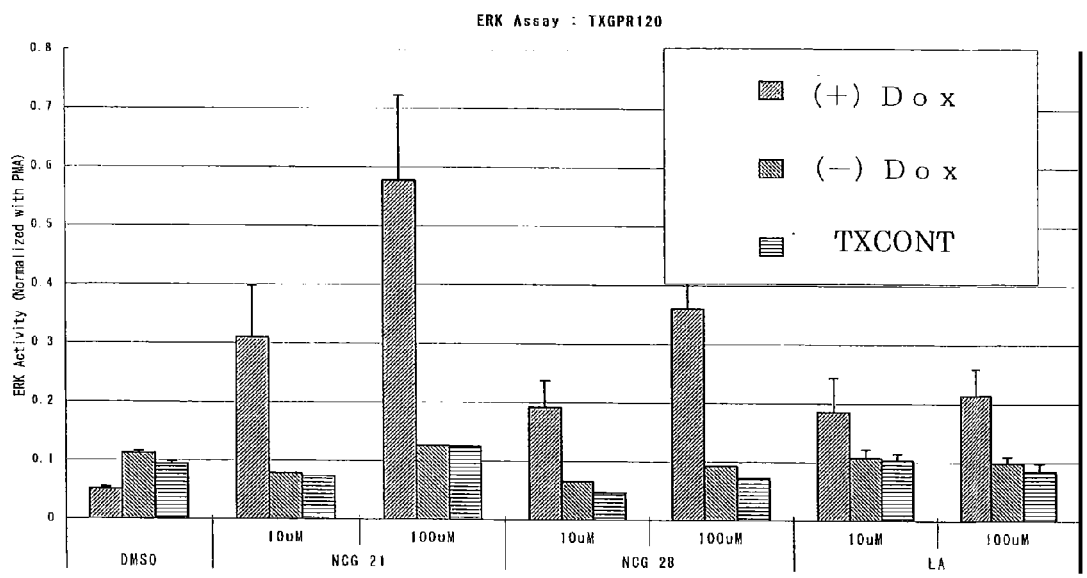

FIG. 7 is a diagram showing the comparison in ERK activity of the compounds (NCG21 and NCG28) using cell line TXGPR120. ERK activity of the compound for the cell treated with Doxycycline (Dox(+)) is compared with the negative controls TXCONT cell, which does not express GPR, and a cell without Doxycycline treatment (Dox(−)).

Figure 8:
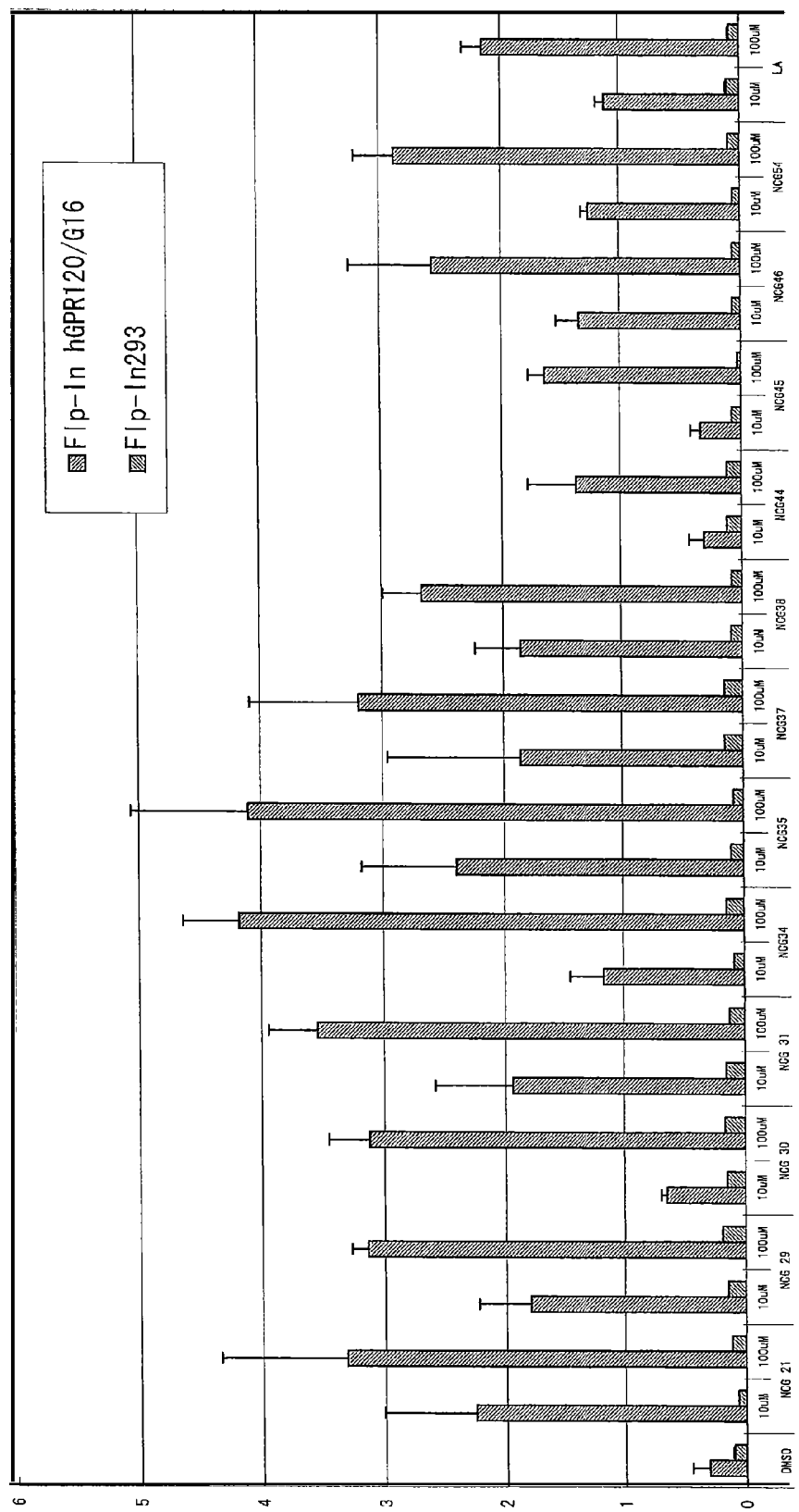

FIG. 8 is a diagram showing the comparisons in ERK activity of other compounds of the present invention (NCG29, NCG30, NCG31, NCG34, NCG35, NCG37, NCG38, NCG44, NCG45, NCG46, and NCG54) using Flp-In h GPR120/G15, which is similar to the cell line TXGPR120.

Figure 9:
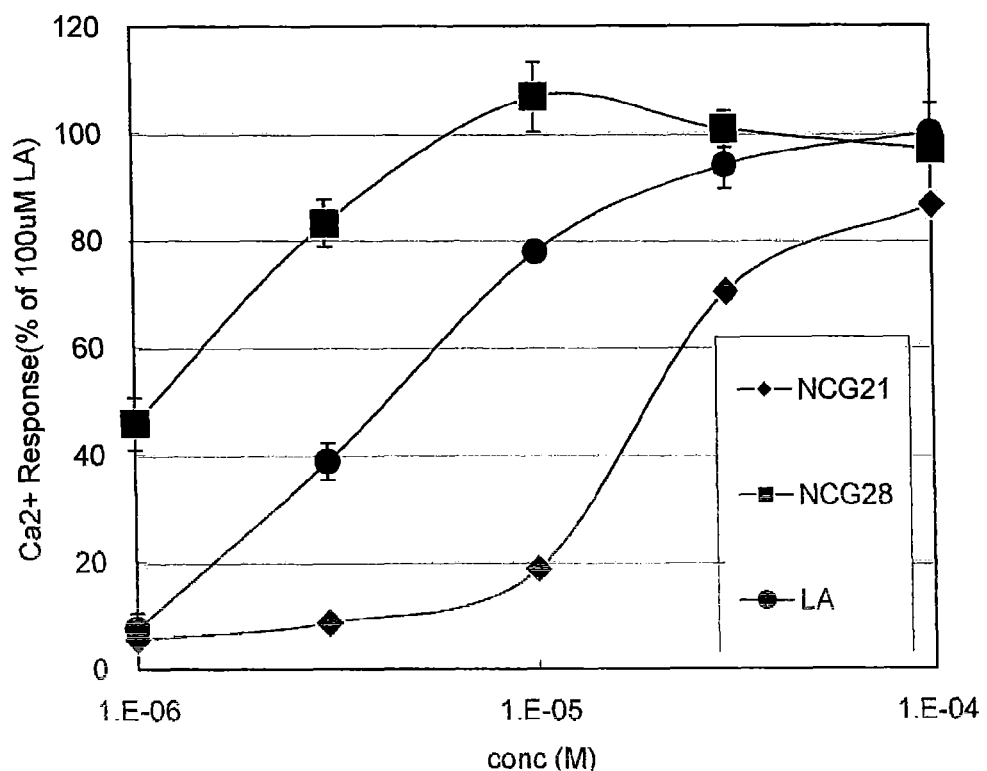

FIG. 9 is a diagram showing the relation between the intracellular $Ca^{2+}$ concentration and the ligand concentration in cell line TXGPR40.

Figure 10:
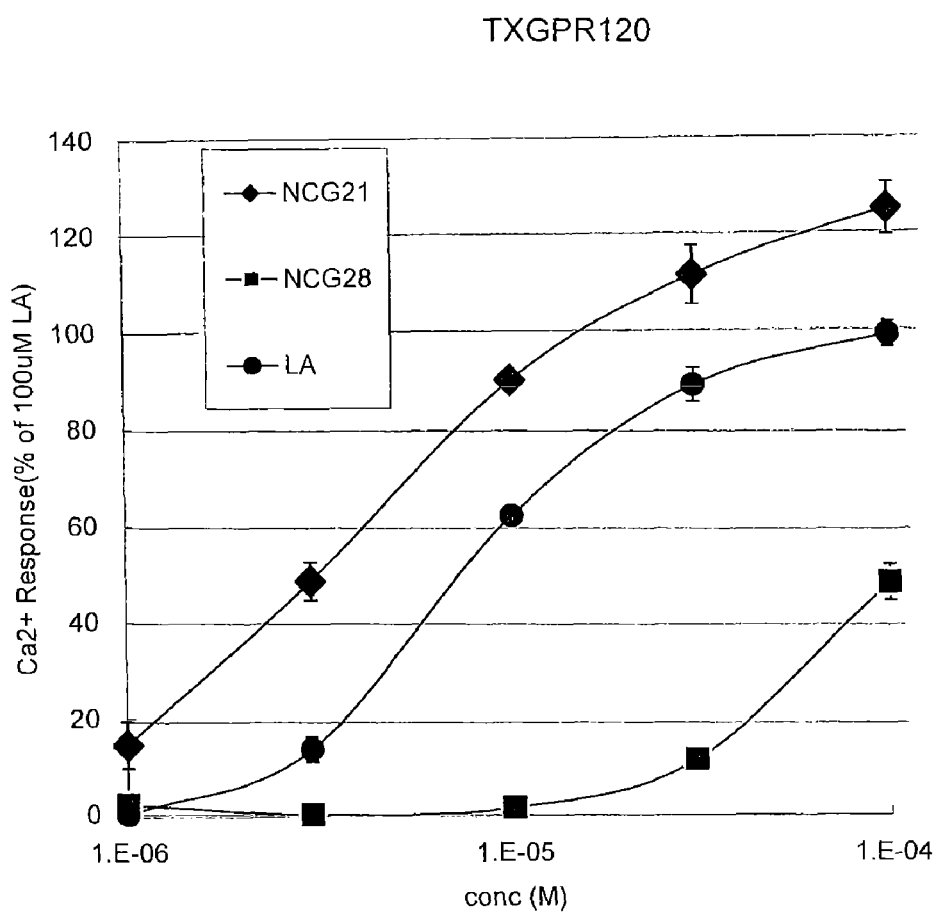

FIG. 10 is a diagram showing the relation between the intracellular $Ca^{2+}$ concentration and the ligand concentration in cell line TXGPR120.

BEST MODE FOR CARRYING OUT THE INVENTION

The phenyl compound according to the present invention is basically represented by the structural formula (A) below.

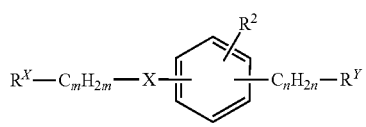

(A)

Particularly preferably, compound of the present invention is represented by the formula (i) below in which the $R^X$—$C_mH_{2m}$—X— and —$C_nH_{2n}$—$R^Y$ groups are linked to a benzene ring at its para positions:

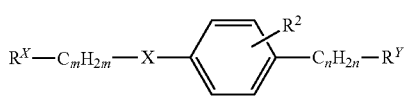

(i)

wherein:

$R^X$ denotes an aromatic hydrocarbon group, an aromatic heterocyclic group having 1 to 4 heteroatoms (wherein said aromatic hydrocarbon group or aromatic heterocyclic group may be substituted with 1 to 3 substituents), or a substituted amino group represented by the general formula (ii) below:

(ii)

wherein:

$R^Y$ denotes a carboxyl group, a 5- or 6-membered aromatic heterocyclic group having 1 to 4 heteroatoms (wherein said aromatic hydrocarbon group or aromatic heterocyclic group may be substituted with 1 to 3 substituents), or a carbamoyl group which may be substituted;

the ring Q denotes an aromatic hydrocarbon group or an aromatic heterocyclic group having 1 to 3 heteroatoms (wherein said aromatic hydrocarbon group or aromatic heterocyclic group may be substituted with 1 to 3 substituents);

$R^1$ denotes a $C_{1-6}$ alkyl group, an aromatic hydrocarbon group, or an aromatic heterocyclic group having 1 to 3 heteroatoms (wherein said $C_{1-6}$ alkyl group, aromatic hydrocarbon group, or aromatic heterocyclic group may be substituted with 1 to 3 substituents);

$R^2$ denotes a hydrogen atom, a $C_{1-4}$ alkyl group, or a $C_{1-4}$ alkoxy group;

m and n are identical or different and are integers of 1 to 5; and

X denotes an oxygen atom, a sulfur atom or —$NR^3$— (where $R^3$ denotes a hydrogen atom or a $C_{1-4}$ alkyl group).

A particularly preferred phenyl compound is an aralkylcarboxylic acid compound represented by the general formula (I) below:

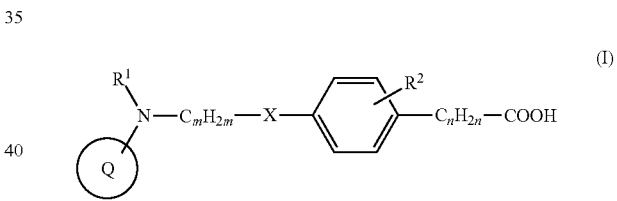

(I)

wherein the ring Q denotes an aromatic hydrocarbon group or an aromatic heterocyclic group having 1 to 4 heteroatoms (wherein said aromatic hydrocarbon group or aromatic heterocyclic group may be substituted with 1 to 3 substituents); $R^1$ denotes a $C_{1-6}$ alkyl group, an aromatic hydrocarbon group, or an aromatic heterocyclic group having 1 to 3 heteroatoms (wherein said $C_{1-6}$ alkyl group, aromatic hydrocarbon group, or aromatic heterocyclic group may be substituted with 1 to 3 substituents); $R^2$ denotes a hydrogen atom, a $C_{1-4}$ alkyl group, or a $C_{1-4}$ alkoxy group; m and n are identical or different and each denotes an integer of 1 to 5; and X denotes an oxygen atom, a sulfur atom or —$NR^3$— (where $R^3$ denotes a hydrogen atom or $C_{1-4}$ alkyl group).

In both general formulas (A) and (i), when $R^X$ is a phenoxyphenyl group, $R^Y$ is a 5- or 6-membered aromatic heterocyclic group having 1 to 4 heteroatoms (wherein said aromatic hydrocarbon group or aromatic heterocyclic group may be substituted with 1 to 3 substituents) or a carbamoyl group which may be substituted.

In the invention of chemical substance, n is 1, 3, 4, or 5, when the ring Q is a pyridyl group, $R^1$ is a $C_{1-6}$ alkyl group or a phenyl group, X is an oxygen atom, $R^2$ is a hydrogen atom, $R^Y$ is a carboxyl group and m is 2.

Examples of the compound represented by the general formula (i) above having particularly outstanding agonistic activity for GPR120 and/or GPR40 include but not limited to:
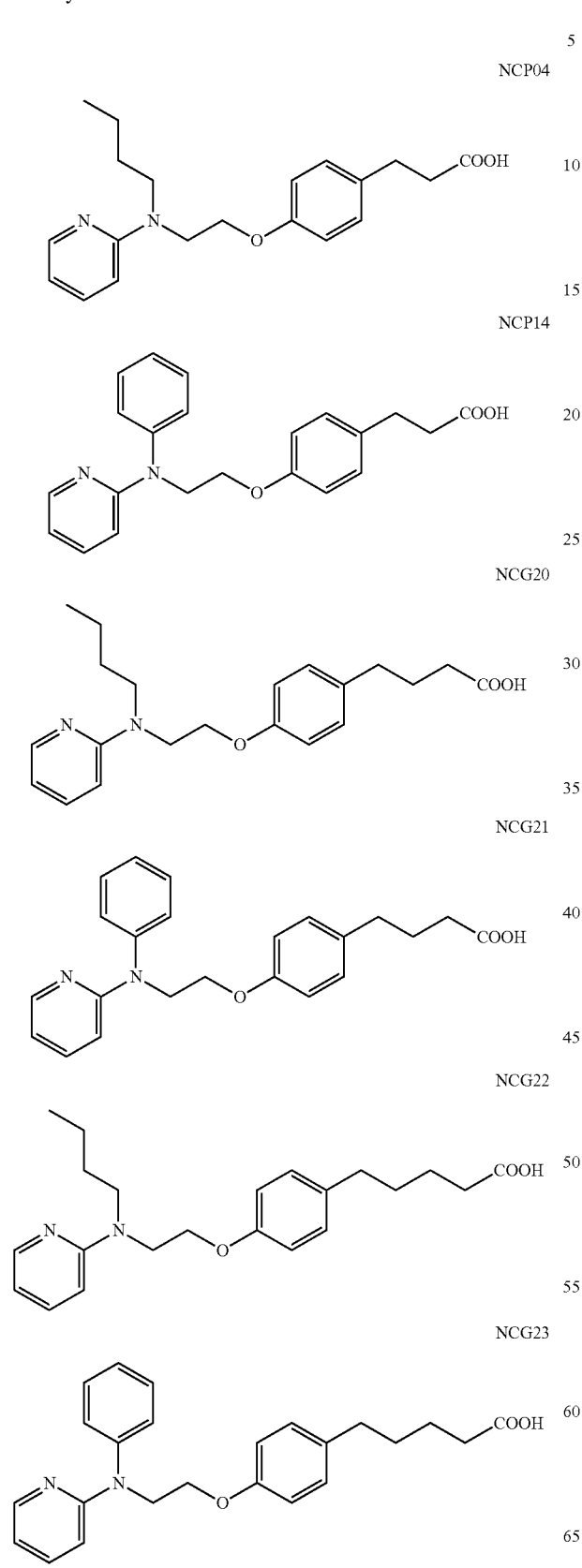
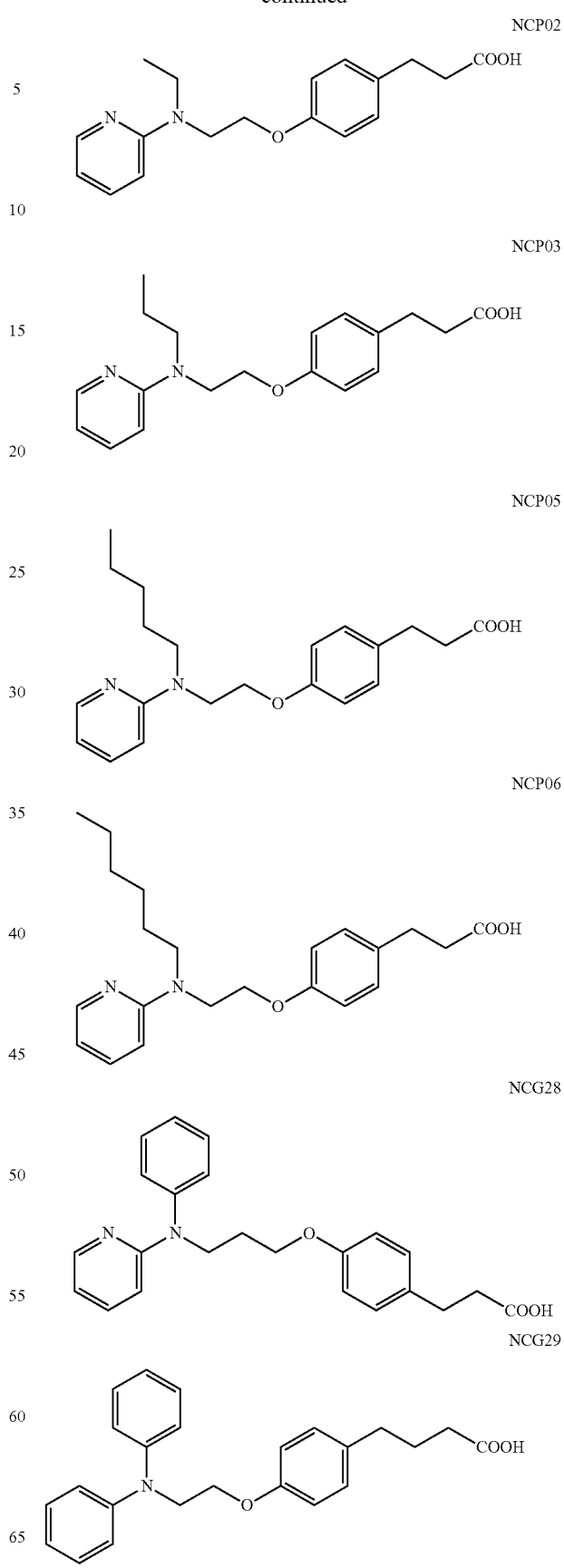

-continued

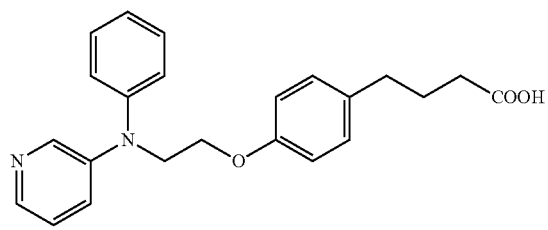

NCG30

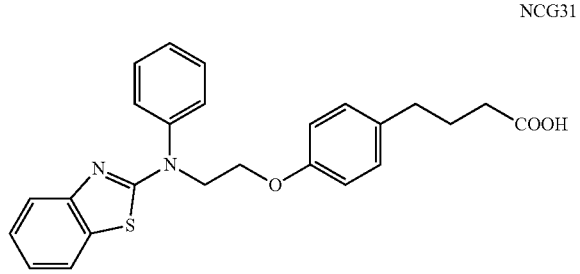

NCG31

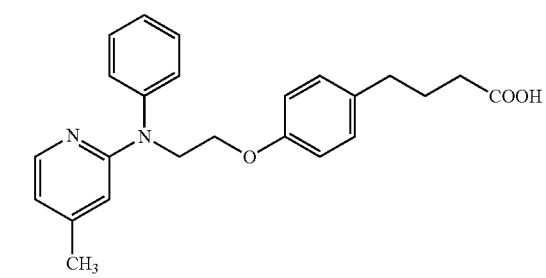

NCG34

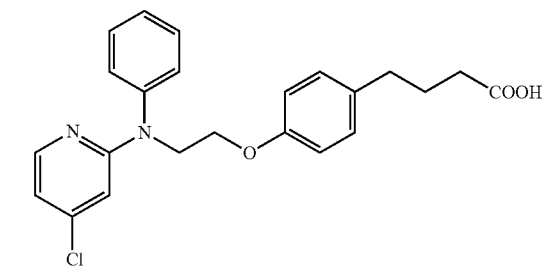

NCG35

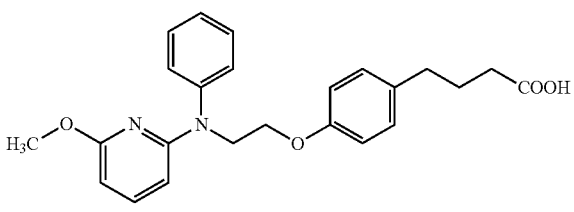

NCG37

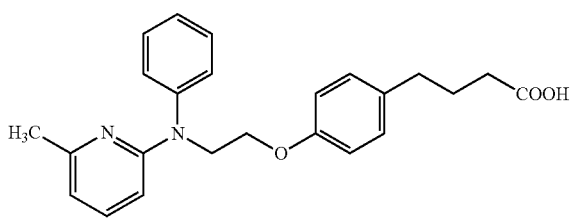

NCG38

-continued

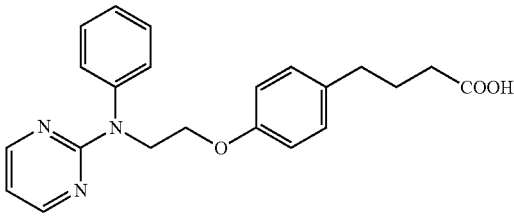

NCG44

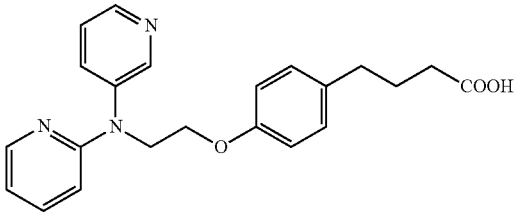

NCG45

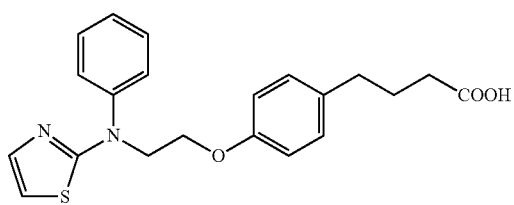

NCG46

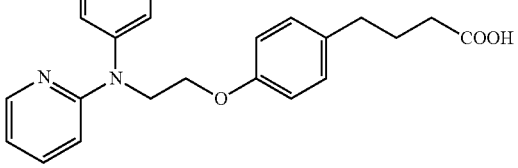

NCG54

Novel among the foregoing compounds are NCP04, NCG20, NCG21, NCG22, NCG23, NCG28, NCG29, NCG30, NCG31, NCG34, NCG35, NCG37, NCG38, NCG40, NCG45, NCG46, and NCG54.

The terms used in the present invention are defined as follows.

"Aromatic hydrocarbon group" means an aryl group having 6 to 14 carbon atoms, and includes, for example, phenyl group, naphthyl group, biphenyl group, anthryl group, indenyl group, azulenyl group, fluorenyl group and phenanthryl group. Said aryl group may be partly saturated in some instances. Examples of partly saturated aryl groups include, for example, dihydroindenyl and tetrahydronaphthyl. $C_{6-10}$ aryl groups are preferable, and biphenyl group, phenyl group, and naphthyl group are more preferable, and phenyl group is most preferable.

Preferred aromatic hydrocarbon group for $R^X$ is a phenoxyphenyl group. Preferred aromatic hydrocarbon group for the ring Q in the formula (I) and preferred aromatic hydrocarbon group for $R^1$ is phenyl group.

"Aromatic heterocyclic group having 1 to 4 heteroatoms" or "aromatic heterocyclic group having 1 to 3 heteroatoms" means any aromatic heterocyclic group that has 1 to 4 (or 1 to 3) identical or different heteroatoms selected from oxygen atom, nitrogen atom, and sulfur atom, as ring member atom(s) in addition to carbon atoms, in which the number of the ring member atoms is 3 to 14, and the rings may be condensed. Preferably, the heterocyclic group is a 5- to 7-membered, particularly preferably 5- to 6-membered, monocyclic aromatic heterocyclic group, or a heterocyclic group in which said aromatic heterocyclic group is condensed with a benzene ring. In the formula (i), a preferable heterocyclic group for $R^X$ is quinolyl group, and a preferable heterocyclic group for $R^Y$ is a tetrazolyl group. In the formula (I), a preferable heterocyclic group for the ring Q is pyridyl group, pyrimidyl group or thiazolyl group which may be condensed with a benzene ring, and a preferable heterocyclic group for $R^1$ is a pyridyl group.

"Monocyclic aromatic heterocyclic group having at least one nitrogen atom" means a 5- or 6-membered monocyclic aromatic heterocyclic group which has at least one nitrogen atom and additionally may have 1 to 3 heteroatoms selected from nitrogen atom, sulfur atom, and oxygen atom, or a heterocyclic group in which said monocyclic aromatic heterocyclic group is condensed with a benzene ring. It includes, for example, a pyridyl group, pyradinyl group, pyrimidinyl group, pyridadinyl group, 1,3,5-triazinyl group, pyrrolyl group, pyrazolyl group, imidazolyl group, 1,2,4-triazolyl group, tetrazolyl group, thienyl group, furyl group, oxazolyl group, isooxazolyl group, thiazolyl group, isothiazolyl group, thiadiazolyl group, quinolyl group and benzothiazolyl group. In the formula (I), a preferable monocyclic heterocyclic group for the ring Q is a pyridyl group, quinolyl group, thiazolyl group, benzothiazolyl group, pyrimidyl group, and quinazolynyl group, particularly preferably a pyridyl group, thiazolyl group, benzothiazolyl group, or pyrimidyl group. A preferred monocyclic heterocyclic group for $R^1$ is a pyridyl group.

"$C_{1-6}$ alkyl group" means linear or branched alkyl group having 1 to 6 carbon atoms. It includes, for example, a methyl group, ethyl group, propyl group, isopropyl group, butyl group, isobutyl group, sec-butyl group, tert-butyl group, pentyl group and hexyl group. A preferred $C_{1-6}$ alkyl group for $R^1$ is a n-butyl group. For the use as an agonist for GPR120, it should preferably have 4 to 6 carbon atoms, and as an agonist for GPR40, it should preferably have 1 to 5, particularly 3 to 6 carbon atoms, without being limited.

"$C_{1-4}$ alkyl group" means any linear or branched alkyl group having 1 to 4 carbon atoms. It includes, for example, a methyl group, ethyl group, propyl group, isopropyl group, butyl group, isobutyl group, sec-butyl group and tert-butyl group.

"$C_{1-4}$ alkoxy group" means any alkoxy group having 1 to 4 carbon atoms in which the alkyl moiety is the "$C_{1-4}$ alkyl group" mentioned above. It includes, for example, a methoxy group, ethoxy group, propoxy group, isopropoxy group, butoxy group, isobutoxy group, sec-butoxy group and tert-butoxy group.

"Halogen atom" means a fluorine atom, chlorine atom, bromine atom, and iodine atom, preferably, fluorine atom and chlorine atom.

"$C_{1-4}$ alkoxycarbonyl group" means any group in which said alkoxyl group having 1 to 4 carbon atoms is linked to a carbonyl group, and includes, for example, a methoxycarbonyl group, ethoxycarbonyl group, propoxycarbonyl group, isopropoxycarbonyl group, butoxycarbonyl group, isobutoxycarbonyl group, s-butoxycarbonyl group and t-butoxycarbonyl group.

"Amino group" means. in addition to an amino group, an amino group substituted with a $C_{1-4}$ alkyl group, specifically, a "mono $C_{1-4}$ alkylamino group" that is mono-substituted with a $C_{1-4}$ alkyl group, or a "di $C_{1-4}$ alkylamino group" that is di-substituted with $C_{1-4}$ alkyl groups. It also includes acylamino group.

"Mono $C_{1-4}$ alkylamino group" means an amino group substituted with one "$C_{1-4}$ alkyl group" defined above, and includes, for example, a methylamino group, ethylamino group, propylamino group, isopropylamino group, butylamino group, isobutylamino group, s-butylamino group, and t-butylamino group.

"Di $C_{1-4}$ alkylamino group" means an amino group substituted with two "$C_{1-4}$ alkyl group" defined above, which may be identical or different. The di $C_{1-4}$ alkylamino group includes, for example, dimethylamino group, diethylamino group, N-ethyl-N-methylamino group, dipropylamino group, and dibutylamino group.

"Acylamino group" means an amino group substituted with "acyl group" mentioned above. It includes, for example, a lower aliphatic acylamino group having 1 to 4 carbon atoms which may be linear or branched, such as acetylamino group, propionylamino group, butyrylamino group, and isobutyrylamino group, or an aromatic acylamino group such as benzoylamino group.

"$C_{1-4}$ alkoxy $C_{1-4}$ alkyl group" means a $C_{1-4}$ alkyl group substituted with said $C_{1-4}$ alkoxy. It includes, for example, methoxymethyl group, 2-methoxyethyl group, 3-methoxypropyl group, and 3-ethoxypropyl group.

"Carbamoyl group which may be substituted" means a carbamoyl group in which the amino group moiety may be substituted with a $C_{1-4}$ alkyl group or $C_{1-4}$ alkylsulfonyl group. It includes, for example, methylcarbamoyl group, ethylcarbamoyl group, dimethylcarbamoyl group, and methylsulfonylcarbamoyl group.

"Agonist for G protein-coupled receptor (GPCR)" specifically means an agonist for GPR120 and/or GPR40 receptor. Preferably, it is an agonist for GPR120.

A preferable aromatic hydrocarbon group for $R^X$ is an aromatic hydrocarbon group that is substituted with at least one substituent, and particularly preferably, a phenoxyphenyl group. When $R^X$ is phenoxyphenyl group, $R^Y$ is a 5- or 6-membered aromatic heterocyclic group having 1 to 4 heteroatoms (wherein said aromatic hydrocarbon group or aromatic heterocyclic group may be substituted with 1 to 3 substituents), preferably a tetrazolyl group, or a carbamoyl group which may be substituted with a substituent such as alkylsulfonyl group, X is preferably a nitrogen atom, and $R^2$ is preferably a hydrogen atom. When $R^X$ is quinolyl group, $R^Y$ is a carboxyl group, a tetrazolyl group, or a carbamoyl group substituted with alkylsulfonyl group, X is a nitrogen atom, and $R^2$ id a hydrogen atom.

A preferred aromatic heterocyclic group having 1 to 4 heteroatoms for $R^X$ may be a condensed ring, particularly preferably a quinolyl group.

$R^Y$ is most preferably a carboxy group. The preferable 5- or 6-membered aromatic heterocyclic group having 1 to 4 heteroatoms for $R^Y$ is a tetrazoyl group, and the preferred carbamoyl group which may be substituted for $R^Y$ is a carbamoyl group in which the amino group is substituted with one alkylsulfonyl group such as methylsulfonyl group.

$R^X$ is most preferably a substituted amino group represented by the formula (ii) below.

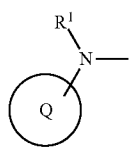

(ii)

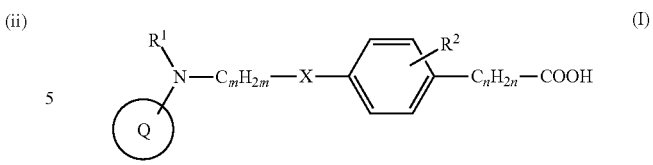

(I)

A preferred aromatic hydrocarbon group for the ring Q is a phenyl group, and a preferred aromatic heterocyclic group for the ring Q is a 5- or 6-membered aromatic heterocyclic group having at least one nitrogen atom. Said aromatic heterocyclic group may be condensed with a benzene ring. Preferred examples of such aromatic heterocyclic group include a pyridyl group which may be condensed with a benzene ring, a pyrimidyl group which may be condensed with a benzene ring, and a thiazolyl group which may be condensed with a benzene ring. These phenyl group or aromatic heterocyclic group may be substituted with 1 to 3 substituents selected from group A below.

[Group A]

(1) a $C_{1-4}$ alkyl group (2) a halogen atom, (3) a $C_{1-4}$ alkoxy group, (4) a $C_{1-4}$ alkoxy $C_{1-4}$ alkyl group, (5) an amino group, and (6) a hydroxyl group;

Particularly preferred substituents are a hydroxyl group, a $C_{1-4}$ alkoxy group, a halogen atom, and a $C_{1-4}$ alkyl group.

A preferred aromatic hydrocarbon group is a phenyl group, and a preferred $C_{1-6}$ alkyl group for $R^1$ is an ethyl group, propyl group, butyl group, n-butyl group, t-butyl group, pentyl group and hexyl group, and a preferred aromatic heterocyclic group for $R^1$ is a pyridyl group.

These aromatic hydrocarbon group or aromatic heterocyclic group may be substituted with 1 to 3 substituents selected from group B below.

[Group B]

(1) a $C_{1-4}$ alkyl group (2) a halogen atom, (3) a $C_{1-4}$ alkoxy group, (4) a $C_{1-4}$ alkoxy $C_{1-4}$ alkyl group, (5) an amino group, and (6) a hydroxyl group;

Each of n and m is an integer of 1 to 5, preferably 1 to 4. m is preferably an integer of 1 to 3, particularly preferably 2. n is preferably an integer of 2 to 4, particularly preferably 2 to 3, especially 3, in view of its agonist activity for GPR120. In the invention of chemical substance relating to the aralkylcarboxylic acid compound or pharmaceutically acceptable salt thereof, n should be 1, 3, 4, or 5, preferably 3, when the ring Q is a pyridyl group, $R^1$ is a $C_{1-6}$ alkyl group or phenyl group, X is an oxygen atom, $R^2$ is a hydrogen atom and m is 2.

X is particularly preferably an oxygen atom.

$R^2$ is particularly preferably a hydrogen atom.

Therefore, the most preferable compound according to the present invention is the aralkylcarboxylic acid compound represented by the general formula (I) below:

wherein, ring Q, $R^1$, $R^2$, X, m, and n are defined as above.

The following describes one example of the typical process for producing the aralkylcarboxylic acid compound represented by the general formula (i) above, particularly (I) above. The process for producing the compound of the present invention is not limited to this example. The compound of the present invention will be produced by appropriately combining and applying known methods.

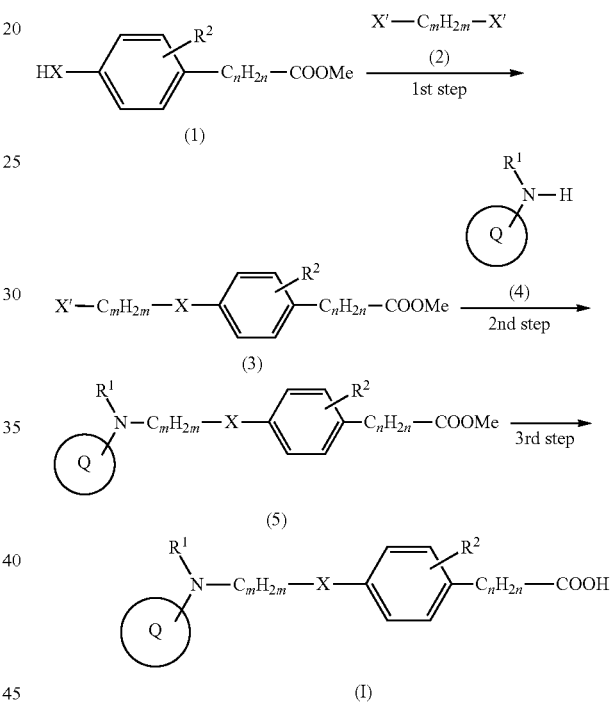

Wherein, ring Q, $R^1$, $R^2$, m, n, X, and $R^3$ are defined as above, and two of X' are identical or different, each denoting a halogen atom or hydroxyl group.

(The First Step)

The first step is a process for preparing the compound (3), which may be obtained by reacting the compound (1) with compound (2) by heating in a solvent in the presence of a base. X' in the compound (2) is a halogen atom such as bromine atom and chlorine atom, and may be identical or different. X' is preferably a bromine atom. The solvent includes, for example, polar aprotic solvents such as N,N-dimethylformamide, dimethylsulfoxide, and acetonitrile; etheric solvents such as diethyl ether, tetrahydrofuran, and dioxane; benzenoid solvents such as toluene and xylene; halogenated solvents such as dichloromethane and chloroform; and esteric solvents such as ethyl acetate and butyl acetate. A preferred solvent is a polar aprotic solvent such as N,N-dimethylformamide, dimethylsulfoxide and acetonitrile. The base used for reaction includes, for example, sodium hydride, lithium hydride, sodium carbonate, potassium carbonate, lithium carbonate, calcium carbonate, sodium hydrogen carbonate, potassium hydrogen carbonate, sodium hydroxide, potassium hydroxide, and lithium hydroxide. Preferably, potassium carbonate is used. The reaction temperature should be 40 to 100° C., preferably 50 to 80° C. The reaction time should be 5 to 100 hours, preferably 24 to 50 hours.

(The Second Step)

The second step is a process for preparing the compound (5), which may be obtained by reacting the compound (3) from the first step with the compound (4) by heating in a solvent in the presence of a base. The solvent includes, for example, polar aprotic solvents such as N,N-dimethylformamide, dimethylsulfoxide and acetonitrile; etheric solvents such as diethyl ether, tetrahydrofuran and dioxane; benzenoid solvents such as toluene and xylene; halogenated solvents such as dichloromethane and chloroform; and esteric solvents such as ethyl acetate and butyl acetate. A preferred solvent is a polar aprotic solvent such as N,N-dimethylformamide, dimethylsulfoxide and acetonitrile. The base used for reaction includes, for example, triethylamine, sodium hydride, lithium hydride, sodium carbonate, potassium carbonate, lithium carbonate, calcium carbonate, sodium hydrogen carbonate, potassium hydrogen carbonate, sodium hydroxide, potassium hydroxide and lithium hydroxide. Preferably, triethylamine or sodium hydride is used. The reaction temperature should be 40 to 100° C., preferably 50 to 80° C. The reaction time should be 1 to 100 hours, preferably 1 to 3 hours. This reaction will proceed smoothly with the aid of catalyst, such as sodium iodide.

(The Third Step)

The third step is a process for preparing the compound (1), which may be obtained by hydrolyzing the compound (5) from the second step in a solvent in the presence of a base. The solvent includes, for example, etheric solvents such as tetrahydrofuran and dioxane; and alcoholic solvents such as methanol and ethanol, and the alcoholic solvents such as methanol and ethanol are preferably used. The base used for reaction includes, for example, sodium carbonate, potassium carbonate, lithium carbonate, calcium carbonate, sodium hydrogen carbonate, potassium hydrogen carbonate, sodium hydroxide, potassium hydroxide and lithium hydroxide. Preferably, sodium hydroxide, potassium hydroxide and lithium hydroxide are used. The reaction temperature should be 10 to 100° C., preferably 20 to 30° C. The reaction time should be 1 to 100 hours, preferably 1 to 24 hours.

The novel agonist for GPCR, particularly the agonist for GPR120 and/or GPR40 according to the present invention comprises as an active ingredient a phenyl compound above, such as aralkylcarboxylic acid compound. The researches by the present inventors revealed that the foregoing compound is capable of activating (or enhancing) the function of GPR120 and/or GPR40.

Specifically, the agonist for GPCR according to the present invention is based on a new mechanism by which the foregoing compound acts on intestinal tract hormone secreting cells, thereby inducing the release of the intestinal tract hormones, which (specifically, CCK and GLP-1) act on the receptor (CCK receptor or GLP-1 receptor) of target cells to exhibit various pharmacological effects.

The present invention exhibits its efficacy in specific diseases by increasing CCK concentration in blood or target organs or GLP-1 concentration in blood or target organs. Therefore, the present invention enables an intensive therapy of various diseases by activating GPCR and increasing CCK concentration or GLP-1 concentration in blood or target organs.

The therapeutic effects exhibited by the increase in CCK concentration include, for example:

(i) Promotion of Digestive Activity:

This includes promoted secretion of pancreatic fluid, promoted secretion of gastric juice, promoted secretion of bile, retention of food in stomach, promoted bowel motility, and prevention of reflux by sphincter contraction in the lower part of esophagus, and accordingly, increasing CCK enables treating the diseases caused by incompetence of digestive activity.

(ii) Appetite Suppression:

Increasing CCK provides a feeling of fullness, thereby suppresses the appetite. Thus, the present invention enables treating the diseases involved with appetite, for example, preventing obesity or treating bulimia nervosa.

(iii) Enhancing Differentiation and Proliferation of Cells in Gastric Mucosa:

The present invention promotes differentiation and proliferation of the cells in gastric mucosa, thereby producing its utility as a therapeutic drug for gastric wall disorder.

(iv) Promotion of Insulin Secretion:

The present invention promotes the secretion of insulin from pancreatic $\beta$ cells, thereby producing its utility as a therapeutic drug for diabetes.

(v) Neural Restoration and Maintenance:

The present invention provides neural restoration and maintenance, thereby finds a utility as a therapeutic drug for mental disorders.

It should be understood that the utility of the present invention is not limited to the subjects mentioned above, and the present invention may address the treatment of any disease that could be treated by the increase in CCK concentration.

On the other hand, diseases and conditions that can be treated by increasing GLP-1 concentration include, for example, followings:

(i) Promotion of Insulin Secretion from Pancreatic $\beta$ Cells:

The present invention promotes insulin secretion from pancreatic $\beta$ cells, thereby finding utility as a therapeutic drug for diabetes.

(ii) Enhancing Differentiation and Proliferation of Pancreatic $\beta$ Cells:

The present invention enhances differentiation and proliferation of pancreatic $\beta$ cells, thereby finding utility as a drug to prevent transition of hyperglycemia, insulin resistance and obesity into diabetes. The present invention may also be used as a drug for improving the survival of $\beta$ cells after engraftment.

(iii) Suppression of Gastric Acid Secretion:

The present invention is capable of suppressing gastric acid secretion, thereby find a utility as a therapeutic drug for gastric hyperacidity.

(iv) Suppression of Bowel Motility:

The present invention is capable of suppressing bowel motility, thereby find a utility as a therapeutic drug for diarrhea.

(v) Maintenance of Neural Plasticity and Survival:

The present invention is capable of maintaining the plasticity and survival of nerves, thereby fining a utility as a therapeutic drug for diseases due to neurological disorder.

(vi) Appetite Suppression:

The present invention is capable of suppressing an appetite, therefore may also be used as a prophylactic or therapeutic drug for obesity.

It should be understood that the utility of the present invention is not limited to the subjects mentioned above, and the present invention may address the treatment of any diseases that could be treated by the increase in GLP-1 concentration.

The phenyl compound, particularly aralkylcarboxylic acid compound, of the present invention induces the releases of both CCK and GLP-1 simultaneously. They often produce the similar drug efficacy, and although they seem to antagonize each other in digestive activity, however, their cooperation provides a smooth digestive activity, wherein the simultaneous releases of both CCK and GLP-1 makes the phenyl compound a physiologically rational therapeutic drug.

Therefore, the phenyl compound, particularly aralkylcarboxylic acid compound, of the present invention induces the release of CCK or GLP-1 through GPR120, and then CCK or GLP-1 effectively acts on target organs for the treatment as follows:
(i) coordinated promotion of digestive activity and treatment of digestion disorder;
(ii) prevention and treatment of obesity by appetite suppression, and treatment of hyperphagia;
(iii) prevention and treatment of diabetes by promotion of insulin secretion from pancreatic β cells or by promotion of differentiation and proliferation of β cells or precursor cells thereof, or an enhancer of the therapeutic effect of the engraftment of β cells or precursor cells thereof;
(iv) enhancement of the therapeutic effect of nerve grafting and nerve suturing by maintaining the plasticity and survival of nerve cells, or treatment of diseases resulting from the disorder in nerve cells such as Alzheimer disease;
(v) treatment of anomalous bowel motility due to enteritis by normalizing bowel motility;
(vi) suppression of impairment of the intestinal cells or nerve cells in intestinal tract.

It is also known that GPR120 is expressed in intestinal tract as well as in lung, pituitary gland, fat cells, and tongue. Accordingly, the present invention is also capable of:
(vii) treating lung diseases such as COPD (chronic obstructive pulmonary disease) by improvement of lung functions by, for example, promoting the secretion of a surfactant;
(viii) promoting the secretion of pituitary hormones from the pituitary gland;
(ix) treating and/or preventing obesity by accelerating lipolysis in fat cells;
(x) improving fat favor.

Moreover, it is known that GPR120 is expressed in pituitary gland, and that the secretion of adrenocorticotropic hormone (ACTH) is suppressed through this receptor (PCT WO2004/065960 A1).

Therefore, the present invention is also expected to be effective as therapeutics for hypersecretory of ACTH or hypersecretory of glucocorticoid (cortisol) and adrenal androgen induced by the stimulation by ACTH.

On the other hand, all the phenyl compounds, particularly aralkylcarboxylic acid compounds, of the present invention exhibit an outstanding agonistic activity for GPR40, whereas only NCG21 shows a relatively weak agonistic activity for GPR40 (see Table 3). GPR40 is expressed in pancreatic β cells and its activation promotes insulin secretion.

Therefore, the agonistic compound for GPR40 is capable of being used as:
(i) a therapeutic drug for diabetes which works by accelerating the secretion of insulin from pancreatic β cells;
(ii) a prophylactic for diabetes which prevents the transition of hyperglycemia, insulin resistance and obesity into diabetes, by enhancing differentiation and proliferation of β cells or precursor cells thereof. The agonistic compound for GPR40 is also capable of being used as a medicament for improving the engraftment and survival of β cells.

The agonist for GPCR comprising as an active ingredient the phenyl compound, particularly aralkylcarboxylic acid compound, of the present invention produces the above-mentioned drug efficacy, and it can be made into a pharmaceutical preparation in the following manner.

The agonist for GPCR according to the present invention may be made into a pharmaceutical preparation adapted to the therapeutically suitable route of administration including intravenous and oral administration. The solution or suspension for intravenous administration may contain, although not limited to: a sterilized diluent such as injectable water, physiological saline, nonvolatile oil, polyethylene glycol, glycerin, propylene glycol, or other synthetic solvents, preservatives such as benzyl alcohol or other methylparabens, antioxidant such as ascorbic acid or sodium hydrogen sulfite, benzalkonium chloride, analgesic such as procaine hydrochloride, chelating agent such as ethylenediaminetetraacetic acid (EDTA), buffer agent such as acetate, citrate or phosphate, and osmoregulating agent such as sodium chloride or dextrose.

The pH may be adjusted with acid or base such as hydrochloric acid or sodium hydroxide. Parenteral preparations may be contained in an ampoule, glass or plastic disposable syringes, or vials for multiple dose administration.

Preparations suitable for injection comprise a sterilized injectable solution or dispersion, comprising a sterilized aqueous solution or dispersion medium and a sterilized powder (comprising lyophilized protein, nucleic acid, etc.) for the preparation at time of use. A suitable carrier for intravenous administration includes physiological saline, bacteriostatic water, CREMOPHOR EL (registered trade mark of BASF, Parsippany, N.J.), and phosphate-buffered physiological saline (PBS). The agonist for GPCR for injection should be sterilized and should have sufficient fluidity for syringability. The carrier may be water, ethanol, polyols (such as glycerol, propylene glycol, and liquid polypropylene glycol), or solvent or dispersion medium containing adequate additives. Adequate fluidity will be ensured by employing a coating material such as lectin, by maintaining adequate particle size in the case of dispersion, and by using a surfactant. Various antibacterial and antifungal agents may be used to prevent contamination by microorganisms, such as paraben, chlorobutanol, phenol, ascorbic acid, and thimerosal. The composition may also contain any isotonic agent, which includes polyalcohols such as sugar, mannitol and sorbitol, and sodium chloride. The composition may also contain an adsorption retardant such as aluminum monostearate and gelatin.

A sterilized injectable solution may be prepared by adding into an appropriate solvent necessary ingredients, either alone or in combination with other ingredients, and adding the active compound in an adequate amount, then sterilizing the mixture. The dispersion is generally prepared by incorporating the active compound into a sterilized medium containing a basic dispersion medium and other optional ingredients. The sterilized powder for a sterilized injectable solution is prepared by vacuum drying and freeze-drying to give a powder comprising the active ingredient and any necessary ingredients derived from the sterilized solution.

The pharmaceutical preparation for oral administration may contain any inactive diluent or any innocuous carrier. The oral preparation may be encapsulated in a gelatin capsules or pressure-compressed to give a tablet. For the treatment by oral administration, the active compound is incorporated with a filler, and used in a form of a tablet, troche or capsule. The oral preparation may also be prepared using a fluidic carrier. The preparation may further contain a pharmaceutically acceptable binder and/or adjuvant substance.

The tablets, pills, capsules, troches, and their analogs may contain any of the following components and any other components having similar properties: fillers such as microcrystalline cellulose; binders such as acasia, tragacanth or gelatin; swelling agents such as starch, lactose, alginic acid, PRIMO-GEL or corn starch; lubricants such as magnesium stearate or STRROTES; smoothing agents such as colloidal silicon dioxide; sweeteners such as sucrose or saccharin; and flavoring additives such as peppermint, methyl salicylate or orange flavor.

The pharmaceutical preparations for systemic administration may be transmucousally or transdermally applied. For transmucosal or transdermal administration, a penetrating agent may be used for the penetration into the target barrier. The penetrating agents for transmucosal administration include surfacactants, bile salts and fusidic acid derivatives. A transnasal spray or suppository can be employed for transmucosal administration. For transmucosal administration, the active compound may be incorporated into an ointment, gel or cream.

The pharmaceutical composition of the present invention may also be prepared in the form of suppository (for example, with a base such as cocoa butter or other glyceride) or retention enema for rectal delivery.

A controlled-release preparation may be prepared by using a carrier that is capable of preventing being removed immediately from the body. The carriers include, for example, biodegradable or biocompatible polymers such as ethylene-vinyl acetate, polyacid anhydride, polyglycolic acid, collagen, polyorthoester and polylactic acid. Such ingredients are commercially available from ALZA Corporation (Mountain View, Calif.) and NOVA Pharmaceuticals, Inc. (Lake Elsinore, Calif.), or they may be readily prepared by those who are skilled in the art. Also, a suspension of liposomes may also be used as a pharmaceutically acceptable carrier. Useful liposomes are, although not limited, prepared as a lipid composition containing phosphatidylcholine, cholesterol and PEG derivative phosphatiadyl ethanol (PEG-PE), filtered through a filter having a appropriate pore size to give an adequate size for the use, then purified by reverse phase evaporation. For example, Fab' fragments of an antibody may be bound to liposome by a disulfide exchange reaction (Martin and Papahadjopoulos, 1982). For detailed description of the preparation, refer to Eppstein et al., 1985 and Hwang et al., 1980.

The dosage of the agonist for GPCR according to the present invention in the treatment or prevention of a specific disease varies depending on the conditions of patient (or animal) to be treated and the method for administration. A person skilled in the art can readily determine an optimal dosage. For example, in the case of parenteral administration, dosage is preferably from about 0.1 μg to 500 mg per kg of patient body weight per day, which would usually be administered in a single dose or multiple doses. A preferable dosage is about 0.1 μg/kg to about 250 mg/kg per day, more preferably about 0.5 mg/kg to about 100 mg/kg per day.

For oral administration, tablets containing 1.0 to 1000 mg of the active ingredient is preferably provided. A preferable dosage of active ingredient is 0.01 to 100 mg/kg for each patient (or animal). The compound is administered 1 to 4 times a day, preferably once or twice a day.

The agonistic activity for GPR120 and GPR40 can be measured for the screening for the phenyl compound, particularly the aralkylcarboxylic acid compound, of the present invention that can be used as a preferable medicament for a disease not described herein.

The invention will be described in more detail with reference to the following examples, which are not intended to limit the scope of the present invention.

Example 1

Preparation of 4-{4-[2-(2-butylpyridinylamino)ethoxy]phenyl}butanoic acid (5, NCG20)

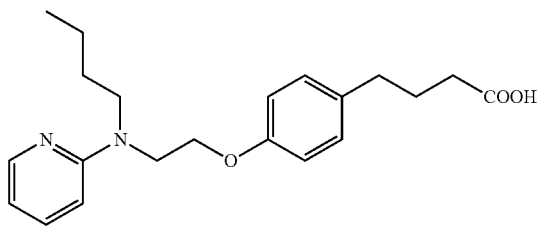

Step 1: Preparation of 4-(4-hydroxyphenyl)butanoic acid (1)

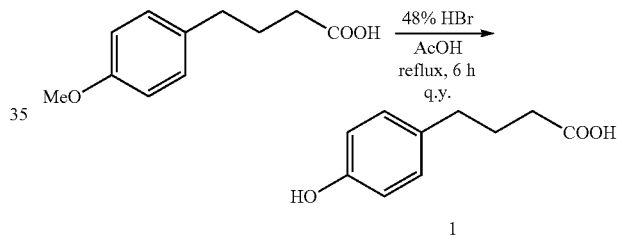

4-(4-methoxyphenyl)butanoic acid (5.0 g) was dissolved in 48% hydrobromic acid (50 mL) and acetic acid (80 mL), then the solution was refluxed by heating for 6 hours. Ethyl acetate (300 mL) is added into the reaction solution, then organic layer was washed with water (100 mL) and saturated sodium chloride solution (50 mL), dried on anhydrous sodium sulfate, filtered and vacuum concentrated, then washed with n-hexane to give the above-identified compound (4.6 g, yield 99%).

$^1$H-NMR (CDCl$_3$, 500 MHz, δ; ppm) 7.04 (2H, d, J=8.6 Hz), 6.75 (2H, d, J=8.6 Hz), 2.60 (2H, t, J=8.0 Hz), 2.36 (2H, t, J=7.3 Hz), 1.92 (2H, quintet, J=7.6 Hz).

Step 2: Preparation of 4-(4-hydroxyphenyl)butanoic acid methyl ester (2)

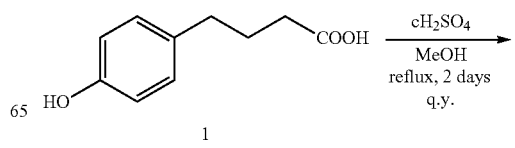

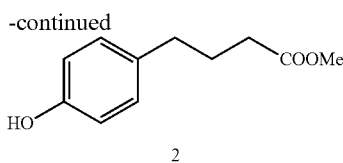

The 4-(4-hydroxyphenyl)butanoic acid (1) (4.6 g) from the previous step was dissolved in methanol (60 mL), concentrated sulfuric acid (1 mL) was added, and refluxed by heating for two days. The reaction solution was poured into water, and extracted with ethyl acetate (200 mL). The organic layer was washed with water (50 mL), saturated aqueous solution of sodium hydrogen carbonate (50 mL) and saturated sodium chloride solution (50 mL). After drying on anhydrous sodium sulfate, filtration and vacuum concentration, the above-identified compound (4.9 g, yield 99%) was obtained.

$^1$H-NMR (CDCl$_3$, 500 MHz, δ; ppm) 7.03 (2H, d, J=8.5 Hz), 6.75 (2H, d, J=8.3 Hz), 4.85 (1H, s), 3.67 (3H, s), 2.58 (2H, t, J=7.6 Hz), 2.32 (2H, t, J=7.3 Hz), 1.92 (2H, quintet, J=7.6 Hz).

Step 3: Preparation of 4-(4-(2-bromoethoxy)phenyl)butanoic acid methyl ester (3)

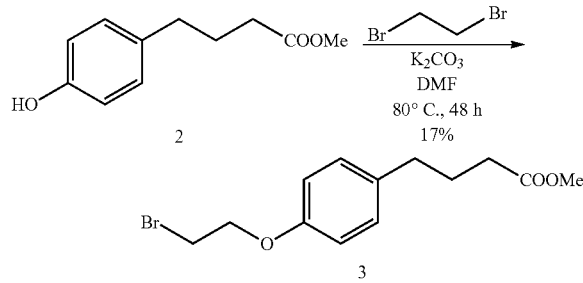

4-(4-hydroxyphenyl)butanoic acid methyl ester (2) (2.6 g) from the previous step was dissolved in N,N'-dimethylformamide (30 mL), 1,2-dibromoethane (12.6 g) and potassium carbonate (3.7 g) were added, and stirred at 80° C. for two days. The reaction solution was poured into water, and extracted with ethyl acetate (100 mL). The organic layer was washed with water (50 mL) and saturated sodium chloride solution (50 mL). After drying on anhydrous sodium sulfate, filtration and vacuum concentration, the residue was purified by silica gel flash column chromatography (developing solvent: n-hexane:ethyl acetate=8:1) to give the above-identified compound (676 mg, yield 17%).

$^1$H-NMR (CDCl$_3$, 500 MHz, δ; ppm) 7.10 (2H, d, J=8.9 Hz), 6.84 (2H, d, J=8.9 Hz), 4.27 (2H, t, J=6.4 Hz), 3.66 (3H, s), 3.63 (2H, t, J=6.4 Hz), 2.59 (2H, t, J=7.6 Hz), 2.32 (2H, t, J=7.6 Hz), 1.92 (2H, quintet, J=7.6 Hz).

Step 4: Preparation of N-butylpyridine-2-amine (4)

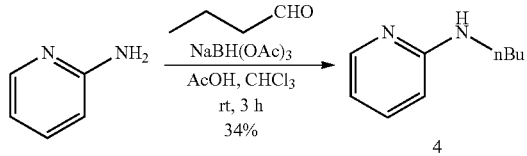

2-aminopyridine (5.0 g) was dissolved in chloroform (40 mL) and acetic acid (10 mL), and n-butyraldehyde (4.2 g) was added, then stirred at room temperature for 30 minutes. Sodium triacetoxyborohydride (16.9 g) was added and stirred at room temperature for three hours. Ethyl acetate (300 mL) was added to the reaction solution, and the organic layer was washed with saturated aqueous solution of sodium hydrogen carbonate (200 mL) and saturated sodium chloride solution (50 mL). After drying on anhydrous sodium sulfate, filtration, and vacuum concentration, the residue was purified by silica gel flash column chromatography (developing solvent: n-hexane:ethyl acetate=2:1) to give the above-identified compound (2.7 g, yield 34%).

$^1$H-NMR (CDCl$_3$, 500 MHz, δ; ppm) 8.06 (1H, d, J=4.9 Hz), 7.40 (1H, t, J=7.8 Hz), 6.54 (1H, dd, J=6.1 Hz), 6.36 (1H, d, J=8.6 Hz), 4.56 (1H, broad s), 3.24 (2H, q, J=7.4 Hz), 1.60 (2H, quintet, J=7.3 Hz), 1.43 (2H, sextet, J=7.6 Hz), 0.95 (3H, t, J=7.4 Hz).

Step 5: Preparation of 4-{4-[2-(2-butylpyridinylamino)ethoxy]phenyl}butanoic acid (5, NCG20)

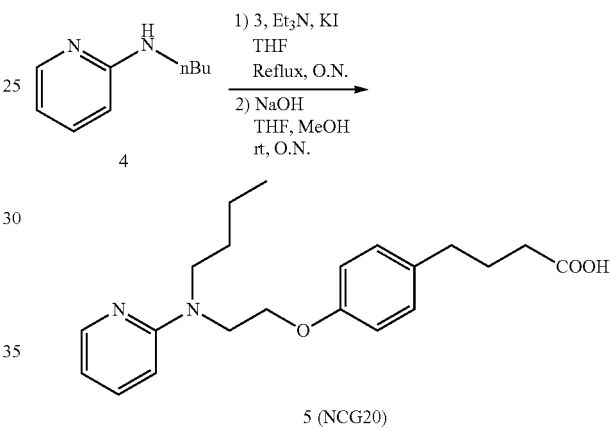

4-(4-(2-bromoethoxy)phenyl)butanoic acid methyl ester (3) (956 mg) from Step 3, and N-butylpyridine-2-amine (4) (1.4 g) from Step 4, were dissolved in tetrahydrofuran (6 mL), then triethylamine (0.88 mL) and potassium iodide (530 mg) were added, and refluxed overnight by heating. Ethyl acetate (100 mL) was added to the reaction solution, and the organic layer was washed with water (100 mL) and saturated sodium chloride solution (50 mL). After drying on anhydrous sodium sulfate, filtration and vacuum concentration, the residue was purified by silica gel flash column chromatography (developing solvent: n-hexane:ethyl acetate=6:1) to give a mixture of 4-{4-[2-(2-butyl(pyridin-2-yl)amino)ethoxy] phenyl}butanoic acid methyl ester and N-butylpyridine-2-amine (4). This mixture was dissolved in methanol (4 mL) and tetrahydrofuran (4 mL), 2N sodium hydroxide aqueous solution (1 mL) was added, then stirred overnight at room temperature. The reaction solution was concentrated with 2N hydrochloric acid (1.1 mL), then the residue was purified by silica gel flash column chromatography (developing solvent: n-hexane:ethyl acetate=1:1) to give the above-identified compound (128 mg, yield 11%) as a colorless oil.

$^1$H-NMR (CDCl$_3$, 500 MHz, δ; ppm) 8.14 (1H, d, J=4.0 Hz), 7.41 (1H, dt, J=1.9, 7.1 Hz), 7.06 (2H, d, J=8.6 Hz), 6.82 (2H, d, J=8.5 Hz), 6.51 (1H, t, J=4.9 Hz), 6.50 (1H, d, J=7.4 Hz), 4.14 (2H, t, J=6.1 Hz), 3.91 (2H, t, J=5.8 Hz), 3.49 (2H, t, J=7.7 Hz), 2.60 (2H, t, J=7.3 Hz), 2.34 (2H, t, J=7.3 Hz), 1.92 (2H, quintet, J=7.7 Hz), 1.62 (2H, quintet, J=7.7 Hz), 1.37 (2H, sextet, J=7.7 Hz), 0.96 (3H, t, J=7.3 Hz); MS (EI) m/z: 356 (M+); HRMS calcd for C21H28N2O3 356.210, found 356.211.

Example 2

Preparation of 4-{4-[2-(2-phenylpyridinylamino)ethoxy]phenyl}butanoic acid (7, NCG21)

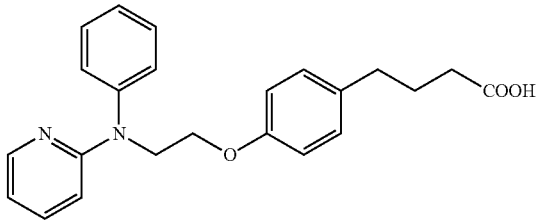

Step 1: Preparation of N-phenylpyridine-2-amine (6)

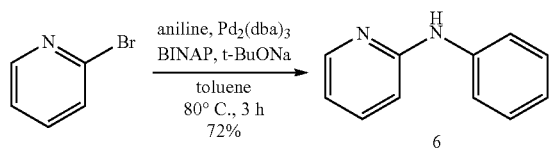

2-bromopyridine (3.0 g) and aniline (5.3 g) were dissolved in toluene (40 mL), tris(dibenzylideneacetone)dipalladium (0) (350 mg), 2,2'-bis(diphenylphosphino)-1,1'-binaphthyl (480 mg) and sodium tert-butoxide (2.6 g) were added, then stirred at 80° C. for three hours. Ethyl acetate (100 mL) was added to the reaction solution, and then washed with water (100 mL). The organic layer was extracted with 2N hydrochloric acid (100 mL), and washed with ethyl acetate (100 mL). The water layer was made alkaline with 2N sodium hydroxide aqueous solution (150 mL) and then extracted with ethyl acetate (200 mL). The organic layer was washed with a saturated sodium chloride solution (50 mL). After drying on anhydrous sodium sulfate, filtration and vacuum concentration, the residue was washed with diethyl ether to give the above-identified compound (2.1 g, yield 72%).

1H-NMR (CDCl3, 500 MHz, δ; ppm) 8.21 (1H, dd, J=0.9, 4.9 Hz), 7.49 (1H, dt, J=2.1, 7.9 Hz), 7.40-7.30 (4H, m), 7.06 (1H, m), 6.88 (1H, d, J=8.2 Hz), 6.73 (1H, ddd, J=0.9, 4.9, 7.1 Hz), 6.61 (1H, broad s).

Step 2: Preparation of 4-{4-[2-(2-phenylpyridinylamino)ethoxy]phenyl}butanoic acid methyl ester

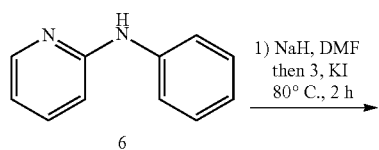

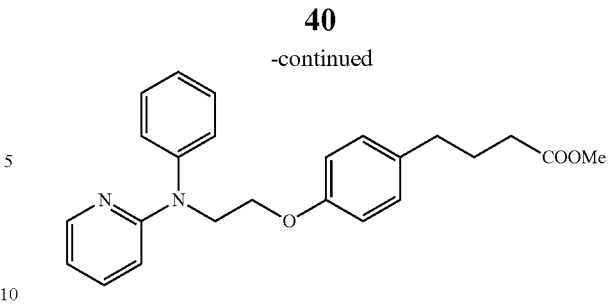

N-phenylpyridine-2-amine (6) (305 mg) from Step 1 was dissolved in N,N-dimethylformamide (3 mL), sodium hydride (60%) (86 mg) was added, then stirred at 60° C. for 30 minutes. Potassium iodide (150 mg) and the solution of 4-(4-(2-bromoethoxy)phenyl)butanoic acid methyl ester (3) (539 mg) from Step 3 of Example 1 in N,N-dimethylformamide (2 mL) were added to the reaction solution, then stirred at 80° C. for two hours. Ethyl acetate (100 mL) was added to the reaction solution, and the organic layer was washed with water (100 mL) and a saturated sodium chloride solution (50 mL). After drying on anhydrous sodium sulfate, filtration and vacuum concentration, the residue was purified by silica gel flash column chromatography (developing solvent: n-hexane: ethyl acetate=6:1) to give the above-identified compound (150 mg, yield 21%).

1H-NMR (CDCl3, 500 MHz, δ; ppm) 8.20 (1H, d, J=4.9 Hz), 7.41 (2H, t, J=7.6 Hz), 7.34 (2H, d, J=7.3 Hz), 7.30-7.20 (2H, m), 7.04 (2H, d, J=8.5 Hz), 6.80 (2H, d, J=8.6 Hz), 6.60 (1H, t, J=7.1 Hz), 6.41 (1H, d, J=8.6 Hz), 4.33 (2H, t, J=6.7 Hz), 4.26 (2H, t, J=6.7 Hz), 3.65 (3H, s), 2.56 (2H, t, J=7.3 Hz), 2.30 (2H, t, J=7.3 Hz), 1.90 (2H, quintet, J=7.3 Hz).

Step 3: Preparation of 4-{4-[2-(2-phenylpyridinylamino)ethoxy]phenyl}butanoic acid (7, NCG21)

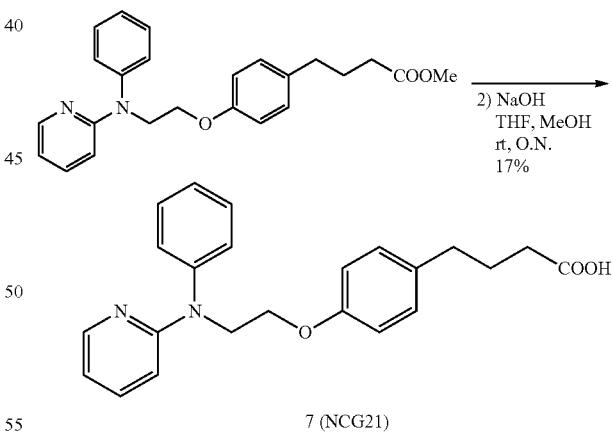

4-{4-[2-(2-phenylpyridinylamino)ethoxy]phenyl}butanoic acid methyl ester (149 mg) from the previous step was dissolved in methanol (2 mL) and tetrahydrofuran (2 mL), and 2N sodium hydroxide aqueous solution (0.6 mL) was added, then stirred overnight at room temperature. The reaction solution was concentrated with 2N hydrochloric acid (0.6 mL), then the residue was purified by silica gel flash column chromatography (developing solvent: chloroform: methanol=19:1) to give the above-identified compound (115 mg, yield 80%) as a colorless crystal.

mp 98-99° C.; $^1$H-NMR (CDCl$_3$, 500 MHz, δ; ppm) 8.21 (1H, d, J=4.0 Hz), 7.41 (2H, t, J=7.3 Hz), 7.33 (2H, d, J=7.4 Hz), 7.30-7.20 (2H, m), 7.04 (2H, d, J=8.6 Hz), 6.79 (2H, d, J=8.6 Hz), 6.60 (1H, t, J=7.0 Hz), 6.41 (1H, d, J=8.9 Hz), 4.32 (2H, t, J=5.2 Hz), 4.26 (2H, t, J=5.8 Hz), 2.59 (2H, t, J=7.4 Hz), 2.34 (2H, t, J=7.4 Hz), 1.91 (2H, quintet, J=7.4 Hz); MS (EI) m/z: 376 (M$^+$); HRMS calcd for C$_{23}$H$_{24}$N$_2$O$_3$ 376.179, found 376.178.

Example 3

Preparation of 5-{4-[2-(2-phenylpyridinylamino)ethoxy]phenyl}pentanoic acid (12, NCG23)

NCG23

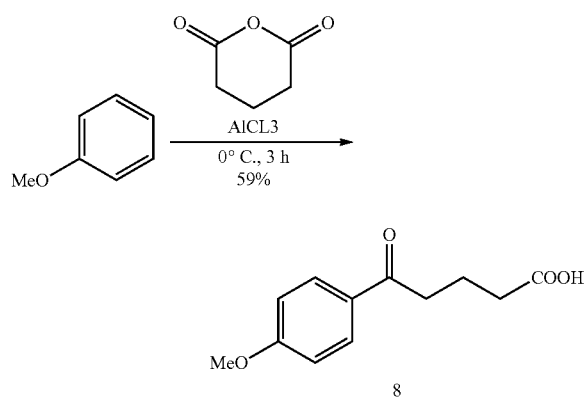

Step 1: Preparation of 5-(4-methoxyphenyl)-5-oxopentanoic acid (8)

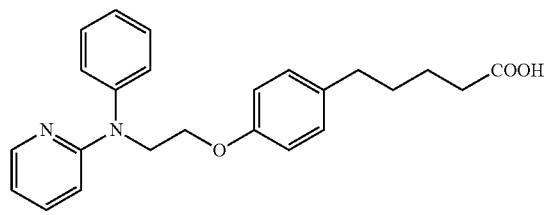

Glutaric anhydride (10.0 g) was dissolved in anisole (100 mL), aluminum chloride (25.7 g) was added, then stirred for three hours on ice. Ethyl acetate (300 mL) was added to the reaction solution, and the organic layer was washed with water (100 mL) and a saturated sodium chloride solution (100 mL). After drying on anhydrous sodium sulfate, filtration and vacuum condensation, the residue was washed with n-hexane to give the above-identified compound (11.5 g, yield 59%) as a colorless solid.

$^1$H-NMR (CDCl$_3$, 500 MHz, δ; ppm) 7.95 (2H, d, J=8.9 Hz), 6.93 (2H, d, J=8.9 Hz), 3.87 (3H, s), 3.03 (2H, t, J=7.0 Hz), 2.50 (2H, t, J=7.3 Hz), 2.08 (2H, quintet, J=7.0 Hz).

Step 2: Preparation of 5-(4-methoxyphenyl)pentanoic acid (9)

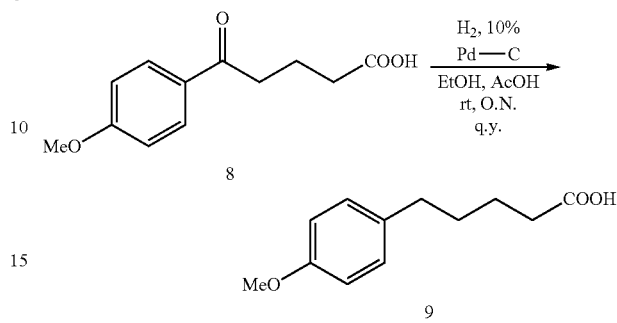

5-(4-methoxyphenyl)-5-oxopentanoic acid (8) (11.5 g) from the previous step was dissolved in ethyl alcohol (150 mL) and acetic acid (50 mL), 10% palladium-activated carbon (1.2 g) was added, then stirred overnight in hydrogen atmosphere at room temperature. After filtration and vacuum concentration, the above-identified compound was obtained as a colorless solid (10.7 g, yield 99%).

$^1$H-NMR (CDCl$_3$, 500 MHz, δ; ppm) 7.08 (2H, d, J=8.6 Hz), 6.82 (2H, d, J=8.8 Hz), 3.78 (3H, s), 2.57 (2H, t, J=7.0 Hz), 2.37 (2H, t, J=7.0 Hz), 1.75-1.55 (4H, m).

Step 3: Preparation of 5-(4-hydroxyphenyl)pentanoic acid

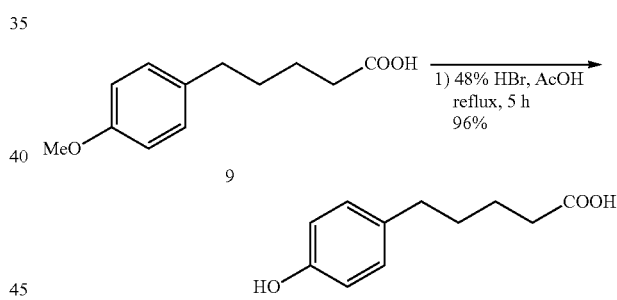

The above-identified compound was obtained (9.9 g, yield 99%) by a similar process to the Step 1 of Example 1, wherein 4-(4-methoxyphenyl)butanoic acid was replaced by 5-(4-methoxyphenyl)pentanoic acid (9) (10.7 g) from the previous step.

$^1$H-NMR (CDCl$_3$, 500 MHz, δ; ppm) 7.03 (2H, d, J=8.6 Hz), 6.74 (2H, d, J=8.5 Hz), 2.56 (2H, t, J=7.4 Hz), 2.37 (2H, t, J=7.3 Hz), 1.72-1.56 (4H, m).

Step 4: Preparation of 5-(4-hydroxyphenyl)pentanoic acid methyl ester

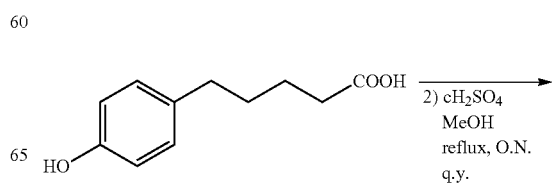

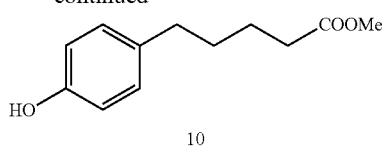

10

The above-identified compound was obtained (10.5 g, yield 99%) by a similar process to the Step 2 of Example 1, wherein 4-(4-hydroxyphenyl)butanoic acid was replaced by 5-(4-methoxyphenyl)pentanoic acid (9.9 g) from in the previous step.

$^1$H-NMR (CDCl$_3$, 500 MHz, δ; ppm) 7.02 (2H, d, J=8.5 Hz), 6.75 (2H, d, J=8.6 Hz), 5.10 (1H, s), 3.67 (3H, s), 2.55 (2H, t, J=7.7 Hz), 2.33 (2H, t, J=7.1 Hz), 1.70-1.55 (4H, m).

Step 5: Preparation of methyl ester of 5-4-(2-bromoethoxy)phenyl)pentanoic acid (11)

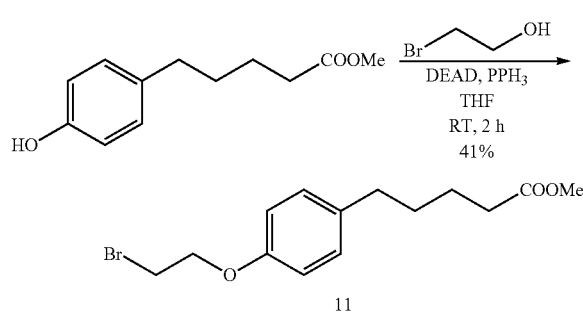

5-(4-hydroxyphenyl)pentanoic acid methyl ester (10) (5.0 g) from the previous step, 2-bromoethanol (3.3 g), and toluene solution of 2.2M diethylazodicarboxylate (16.4 mL) were dissolved in tetrahydrofuran (65 mL), then triphenylphosphine (9.5 g) was added on ice, and stirred at room temperature for two hours. After vacuum concentration, the residue was purified by silica gel flash column chromatography (developing solvent: n-hexane:ethyl acetate=8:1) to give the above-identified compound (3.1 g, yield 41%).

$^1$H-NMR (CDCl$_3$, 500 MHz, δ; ppm) 7.09 (2H, d, J=8.6 Hz), 6.83 (2H, d, J=8.9 Hz), 4.27 (2H, t, J=6.4 Hz), 3.66 (3H, s), 3.62 (2H, r, J=6.4 Hz), 2.57 (2H, t, J=7.6 Hz), 2.33 (2H, t, J=7.3 Hz), 1.70-1.55 (4H, m).

Step 6 and Step 7: Preparation of 5-{4-[2-(2-phenylpyridinylamino)ethoxy]phenyl}pentanoic acid (12, NCG23)

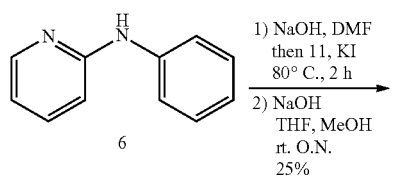

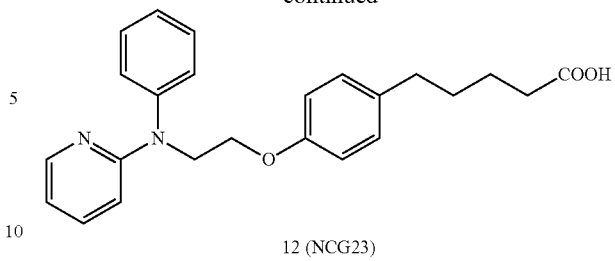

12 (NCG23)

The above-identified compound was obtained as a colorless crystal (176 mg, yield 25%) by a similar process to the Step 2 and Step 3 in Example 2, wherein 4-(4-(2-bromoethoxy)phenyl)butanoic acid methyl ester (3) was replaced by 5-4-(2-bromoethoxy)phenyl)pentanoic acid methyl ester (11) (565 mg) from the previous step.

mp 74-75° C.; $^1$H-NMR (CDCl$_3$, 500 MHz, δ; ppm) 8.21 (1H, d, J=4.9 Hz), 7.41 (2H, t, J=8.3 Hz), 7.33 (2H, d, J=8.6 Hz), 7.30-7.22 (2H, m), 7.03 (2H, d, J=8.6 Hz), 6.79 (2H, d, J=8.6 Hz), 6.60 (1H, t, J=6.0 Hz), 6.41 (1H, d, J=8.9 Hz), 4.32 (2H, t, J=6.1 Hz), 4.26 (2H, t, J=6.1 Hz), 2.55 (2H, t, J=7.4 Hz), 2.35 (2H, t, J=7.0 Hz), 1.72-1.57 (4H, m); MS (EI) m/z: 390 (M$^+$); HRMS calcd for C$_{24}$H$_{26}$N$_2$O$_3$ 390.194, found 390.195.

Example 4

Preparation of 5-{4-[2-(2-butylpyridinylamino)ethoxy]phenyl}pentanoic acid (13, NCG22)

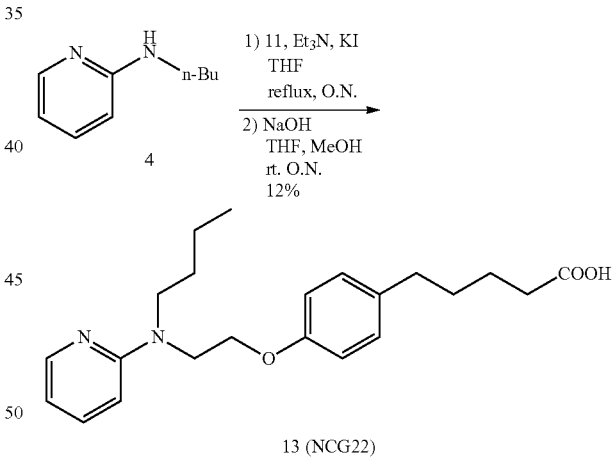

13 (NCG22)

The above-identified compound was obtained as a colorless oil (107 mg, yield 14%) by a similar process to the Step 5 in Example 1, wherein 4-(4-(2-bromoethoxy)phenyl)butanoic acid methyl ester (3) was replaced by of 5-4-(2-bromoethoxy)phenyl)pentanoic acid methyl ester (11) (595 mg) from Step 5 in Example 3.

$^1$H-NMR (CDCl$_3$, 500 MHz, δ; ppm) 8.14 (1H, d, J=4.9 Hz), 7.41 (1H, dt, J=1.9, 7.1 Hz), 7.05 (2H, d, J=8.6 Hz), 6.82 (2H, d, J=8.6 Hz), 6.51 (1H, t, J=4.9 Hz), 6.50 (1H, d, J=7.4 Hz), 4.14 (2H, t, J=6.2 Hz), 3.91 (2H, t, J=5.8 Hz), 3.49 (2H, t, J=7.7 Hz), 2.56 (2H, t, J=7.4 Hz), 2.35 (2H, t, J=7.0 Hz), 1.57-1.70 (6H, m), 1.37 (2H, sextet, J=7.6 Hz), 0.96 (3H, t, J=7.7 Hz); MS (EI) m/z: 370 (M$^+$); HRMS calcd for C$_{22}$H$_{30}$N$_2$O$_3$ 370.226, found 370.226.

The following compounds were prepared in the similar way as mentioned above or according to any known methods.
TABLE 1
Structural formula
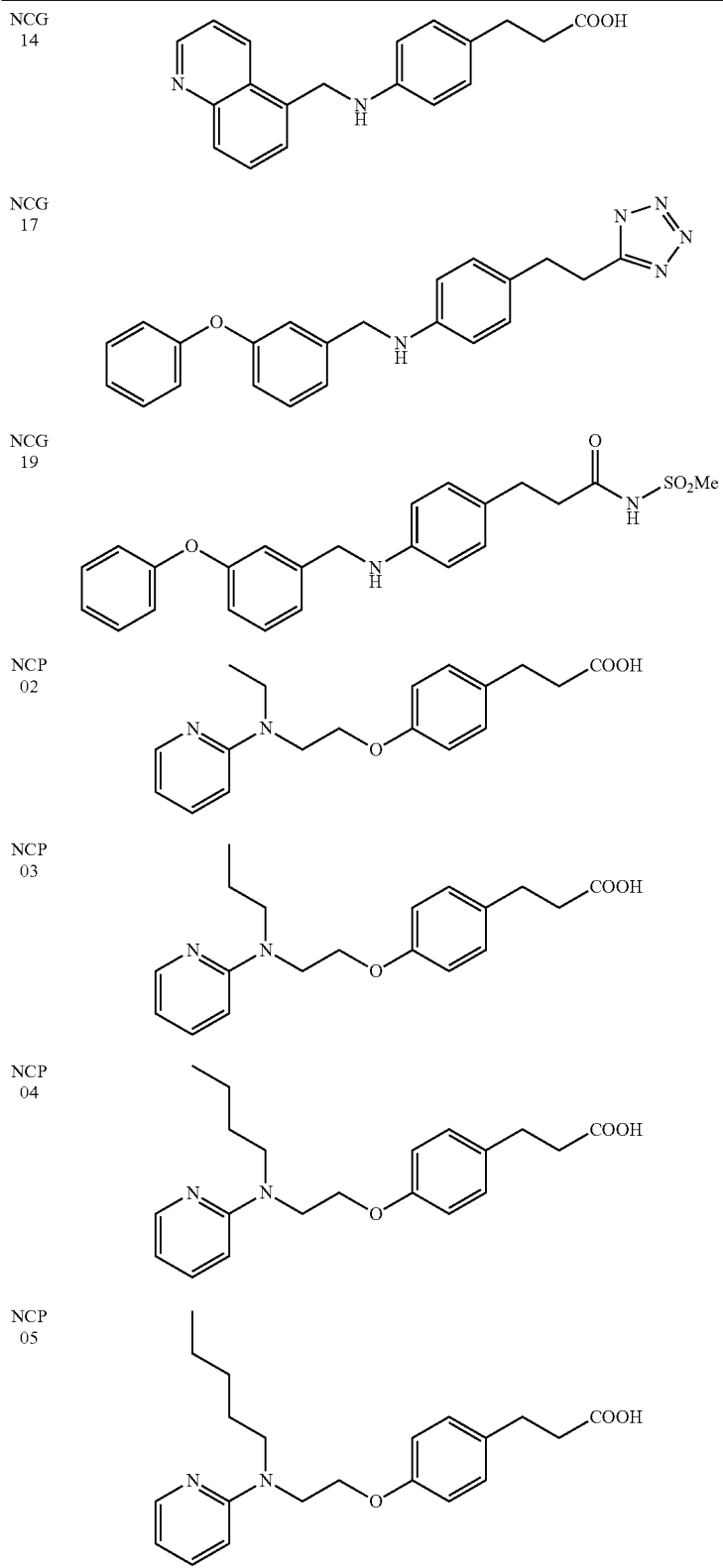
NCG 14
NCG 17
NCG 19
NCP 02
NCP 03
NCP 04
NCP 05

TABLE 1-continued

Structural formula

NCP 06: *(structure: 2-pyridyl-N(hexyl)-N-CH2CH2-O-C6H4-CH2CH2-COOH)*

NCP 14: *(structure: 2-pyridyl-N(phenyl)-N-CH2CH2-O-C6H4-CH2CH2-COOH)*

NCG 28: *(structure: 2-pyridyl-N(phenyl)-N-CH2CH2CH2-O-C6H4-CH2CH2-COOH)*

NCG 29: *(structure: diphenylamino-CH2CH2-O-C6H4-CH2CH2CH2-COOH)*

NCG 30: *(structure: 3-pyridyl-N(phenyl)-N-CH2CH2-O-C6H4-CH2CH2CH2-COOH)*

NCG 31: *(structure: benzothiazol-2-yl-N(phenyl)-N-CH2CH2-O-C6H4-CH2CH2CH2-COOH)*

TABLE 1-continued

| | Structural formula |
|---|---|
| NCG 34 | 4-(4-(2-((4-methylpyridin-2-yl)(phenyl)amino)ethoxy)phenyl)butanoic acid (NCG34) |
| NCG 35 | 4-(4-(2-((4-chloropyridin-2-yl)(phenyl)amino)ethoxy)phenyl)butanoic acid |
| NCG 37 | 4-(4-(2-((6-methoxypyridin-2-yl)(phenyl)amino)ethoxy)phenyl)butanoic acid |
| NCG 38 | 4-(4-(2-((6-methylpyridin-2-yl)(phenyl)amino)ethoxy)phenyl)butanoic acid |
| NCG 44 | 4-(4-(2-(phenyl(pyrimidin-2-yl)amino)ethoxy)phenyl)butanoic acid |
| NCG 45 | 4-(4-(2-(pyridin-2-yl(pyridin-3-yl)amino)ethoxy)phenyl)butanoic acid |

TABLE 1-continued

Structural formula

NCG 46: [structure showing phenyl-thiazol-2-yl-amino-ethoxy-phenyl-butanoic acid derivative]

NCG 54: [structure showing 4-(dimethylamino)phenyl-(pyridin-2-yl)amino-ethoxy-phenyl-butanoic acid derivative]

These compounds were used for various tests shown below.

Test Example 1

Screening for GPR40 and GPR120 Ligands by Extracellular Signal-Regulated Kinase (ERK) Assay This Test 1 was carried out by using the following materials and methods.

1. Recovery of Protein (1) In this test, the cell lines TXGPR40 and TXGPR120 were plated in 35-mm dishes in $5 \times 10^5$ cells/per dish. After their colonization on the dishes was confirmed, the cells were treated with Doxycycline (10 μg of Doxycycline was added to the cell solution), and starved (the medium was replaced with FBS(−) medium) after 28 hours, then assayed 20 hours thereafter.

Here, TXGPR40 and TXGPR120 each denotes the cell line transfected with the plasmid in which human GPR40 (hGPR40) or human GPR120 (hGPR120) gene, respectively, has been incorporated into a expression vector that expresses said gene upon the treatment with Doxycycline, so that the cell is capable of a stable expression of GPR40 or GPR120 protein.

(2) The ligand used in this test includes NCP04, NCP14, NCG20, NCG21, NCG22, NCG23, NCP02, NCP03, NCP05, NCP06, NCG14, NCG17, NCG19, NCG28, NCG29, NCG30, NCG31, NCG34, NCG35, NCG37, NCG38, NCG44, NCG45, NCG46, and NCG54.

Each ligand was dissolved in DMSO, diluted tenfold with the medium to make the total amount of 100 μl. DMSO was used as the negative control, and PMA (phorbol-12-myristate-13-acetate) was used as the positive control.

(3) The medium was removed from the dish of the cell to reduce the total amount of liquid to 0.9 ml.

(4) The ligand solution was added dropwise to the cell solution, and dispersed by gently shaking the dish, and allowed to react at room temperature.

(5) After 5 minutes of reaction, the medium was discarded, and the remaining medium on the dish was removed on ice using an aspirator.

(6) 150 μl of Lysis buffer (50 mM HEPES (pH 7.0), 150 mM NaCl, 10% glycerol, 1% NonidetP-40, 2 mM $MgCl_2$, 1 mM EDTA, 100 mM NaF, 10 mM sodium phosphate, 1 mM $Na_3VO_4$, 20 mM β-glycerophosphate, and Proteinase inhibitor) were added, then the cells were collected using a cell scraper.

(7) The recovered liquid was mixed with 150 μl (equal amount) of 1×SDS Sample Buffer (0.1 M Tris-HCl (pH 6.8), 4% SDS, 12% mercaptoethanol, 20% glycerol, BPB), then used for Western Blotting mentioned below, or stored at −20° C.

2. SDS-PAGE (1) The crude enzyme solution mixed with SDS Sample Buffer was subjected to ultrasonication with a sonifier, then incubated at 90° C. for five minutes.

(2) The mixture was vortexed and centrifuged at 15,000 rpm for five minutes at 4° C.

(3) The supernatant of the centrifuged sample was applied to two 7.5% acrylamide gel slabs placed in an electrophoresis tank filled with 1×SDS-PAGE Running Buffer (25 mM Tris, 0.2 M Glycin, and 1% SDS). Electrophoresis was carried out under a constant current of 40 mA for about 80 to 90 minutes.

3. Blotting (Semi-Dry Method)

(1) A PVDF membrane cut in the same size as the gel slab was immersed in methanol for about 15 seconds and then shaken in Transfer Buffer C solution (25 mM Tris, 0.02% SDS, 2% methanol and 40 mM 6-aminohexanoic acid) at room temperature to swell for 15 minutes. Filter paper for blotting was cut into a 10-cm square.

(2) On the blotting apparatus were placed sequentially two pieces of filter paper immersed in A solution (0.3 M Tris, 0.02% SDS and 2% methanol), two pieces of filter paper immersed in B solution (25 mM Tris, 0.02% SDS and 2% methanol), and the membrane thereon. The gel slab after electrophoresis, and finally two pieces of filter paper immersed in C solution was placed thereon, and the apparatus was closed.

(3) The protein was transferred to the membrane at 15 V for 30 minutes.

4. Blocking (1) The following procedure was all carried out at room temperature. After the protein transfer, the membrane was placed into a vial containing 1×TTBS (0.2 M Tris, 1.5 M NaCl, 0.2% Tween 20) and washed for 15 minutes.

(2) TTBS was discarded, and about 10 ml of Block Ace was added and blocked on a shaker for one hour.

5. Primary Antibody (1) The primary antibodies (p44/42 MAP Kinase Antibody and Phospho-p44/42 MAP Kinase Antibody) were each diluted 1000-fold with TTBS.

(2) After blocking, the Block Ace solution was removed, the solution of the primary antibody was added and allowed to react on the shaker for two hours.

6. Secondary Antibody (1) The secondary antibody (Anti-rabbit Ig, Horseradish Peroxidase linked F(ab')$_2$ fragments) was diluted 5000-fold with TTBS.

(2) The primary antibody solution was removed and the membrane was washed three times on the shaker in TTBS for five to ten minutes each.

(3) TTBS was removed and the solution of secondary antibody was added and left for 1 hour on the shaker.

7. Detection (1) 2 ml each of Detection Reagent 1 and Detection Reagent 2 from ECL kit were mixed together on ice.

(2) The solution of secondary antibody was removed from the membrane reacted with the secondary antibody and then washed three times on the shaker in TTBS for five minutes each.

(3) The liquid was thoroughly removed from the membrane, which was then placed in a plastic bag, and 2 ml of the Detection Reagent mixture was added per each membrane.

(4) The membrane was kept in contact with a film in the cassette for one to five minutes, and the film was developed using an automatic developing machine.

8. Analysis (1) The developed film were scanned and processed by a computer to digitized each band by using "Image J" application (Image J 1.345: a free software program released from National Institutes of Health).

(2) The values of individual drugs were normalized by DMSO and PMA and compared.

Each ligand (10 µM or 100 µM in concentration) was reacted with TXGPR40 and TXGPR120. Resulting signals were digitized and normalized by DMSO and PMA.

Figure 1:
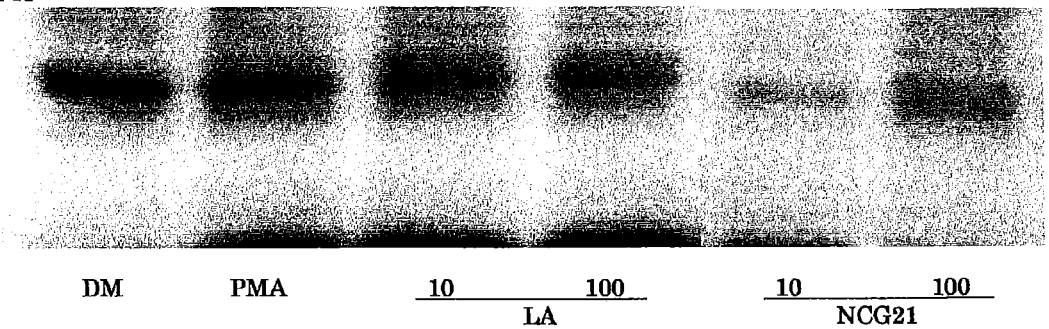
FIG. 1 is a diagram indicating the results of the screening for a GPR40 ligand by ERK assay in Test Example 1.
Figure 1:
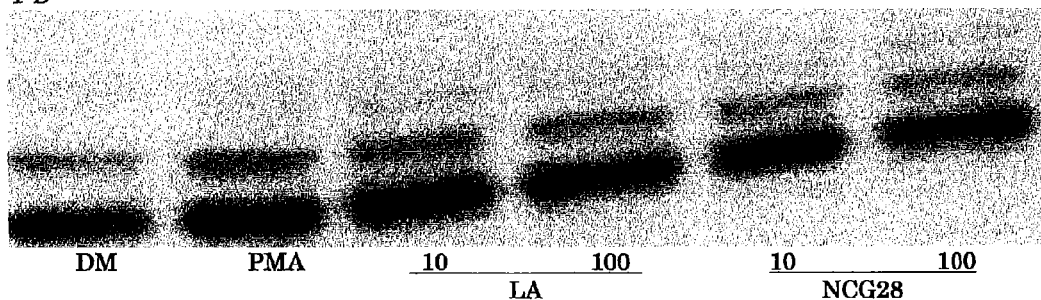
Figure 1:
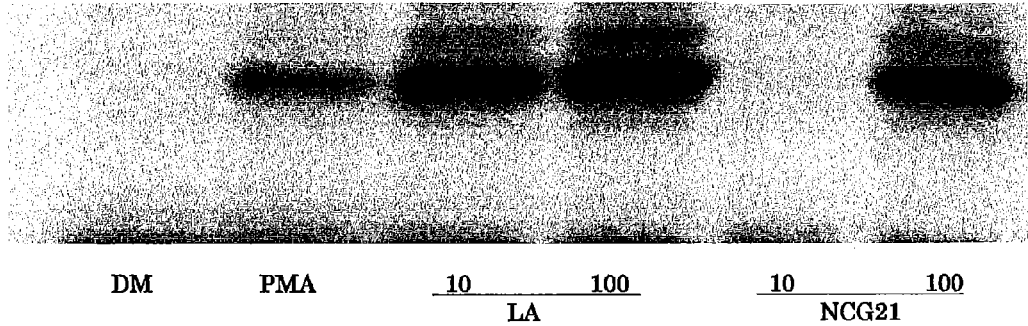
Figure 1:
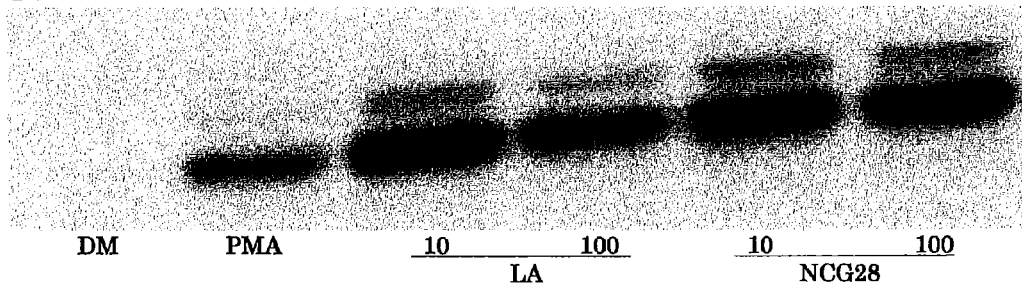

The results of TXGPR40 and TXGPR120 are shown in FIGS. 1 and 2, respectively.

The ERK activity of the compound for those cell treated with Doxycycline (Dox(+)) was compared with the negative controls, TXCONT, which has been transfected with an expression vector without the GPR insert, and the cell without Doxycycline treatment (Dox(−)).

Here, DM denotes DMSO as a negative control, and PMA denotes Phorbol-12-myristate-13-acetate as a positive control. LA denotes cis-α-linolenic acid as a positive object. The compounds tested are NCG21 and NCG28.

1A is a diagram of total ERK detection by Western blotting in a cell line TXGPR40 stimulated with NCG21.

1B shows the results of total ERK detection by Western blotting in cell line TXGPR40 stimulated with NCG28.

1C shows the results of phosphorylated ERK detection by Western blotting in cell line TXGPR40 stimulated with NCG21.

1D shows the results of phosphorylated ERK detection by Western blotting in cell line TXGPR40 stimulated with NCG28.

FIG. 2 is a diagram showing the results of the screening for GPR40 ligand by ERK assay in Test Example 1. The vertical axis represents phospho-ERK/total ERK.

In the case of GPR40, stimulation with NCG21 and NCG28 activates ERK, and particularly stimulation with NCG28 activates ERK at lower concentrations.

FIG. 3 shows the comparison in ERK activity of each compound (NCG21 or NCG28) using the cell line TXGPR40. Likewise, FIG. 4 shows the comparison in ERK activity of the compounds NCG21, NCG29, NCG30, NCG31, NCG34, NCG35, NCG37, NCG38, NCG44, NCG45, NCG46, and NCG54, arranged left to right. The ERK activity of the compound for those cells treated with Doxycycline (Dox(+)) was compared with that for the negative controls, TXCONT without GPR incorporated therein and the cells without Doxycycline treatment (Dox(−)). NCG28, NCG29, NCG30, NCG31, NCG35, and NCG38 strongly activated ERK for GPR40.

FIG. 5 shows the result of screening for GPR120 ligand by ERK assay in Test Example 1.

In FIG. 5, DM denotes DMSO as a negative control, and PMA denotes Phorbol-12-myristate-13-acetate as a positive control. LA denotes cis-α-linolenic acid as a positive object. The compounds tested are NCG21 and NCG28.

FIG. 5A shows the results of total ERK detection by Western blotting in cell line TXGPR120 stimulated with NCG21.

FIG. 5B shows the results of total ERK detection by Western blotting in cell line TXGPR120 stimulated with NCG28.

FIG. 5C shows the results of phosphorylated ERK detection by Western blotting in cell line TXGPR120 stimulated with NCG21.

FIG. 5D shows the results of phosphorylated ERK detection by Western in cell line TXGPR120 stimulated with NCG28.

In the case of GPR120, stimulation with NCG21 and NCG28 activate ERK, although stimulation with NCG21 activates ERK more strongly.

FIG. 6 is a diagram showing the results of screening for GPR120 ligand by ERK assay in Test Example 1. The vertical axis represents phospho-ERK/total ERK.

In the case of GPR120, stimulation with NCG21 and NCG28 activates ERK, although stimulation with NCG21 activates ERK more strongly.

FIG. 7 is a diagram showing the comparison in ERK activity of the compounds (NCG21 and NCG28) using cell line TXGPR120. Likewise, FIG. 8 shows the comparison in ERK activity of other compounds of the present invention (NCG29, NCG30, NCG31, NCG34, NCG35, NCG37, NCG38, NCG44, NCG45, NCG46, and NCG54, arranged from left to right) using the cell line TXGPR120. The ERK activity of the Doxycycline-treated cell (Dox(+)) was compared with the negative controls, TXCONT which has not been introduced with GPR and the cell without Doxycycline treatment (Dox(−)).

The results show that NCG21, NCG29, NCG30, NCG31, NCG34, NCG35, NCG37, NCG38, NCG46, and NCG54, especially NCG21, NCG29, NCG31, NCG35, NCG37, and NCG38, strongly activate ERK for GPR120, and hence they are outstanding agonists for GPR120. Moreover, some of these compounds, such as NCG21, NCG30, NCG37, NCG46, and NCG54 are found to be selective for GRP120.

Test Example 2

GLP-1 (Glucagon-Like Peptide) Release Test in Mice

C57BL/6J mice (8 weeks old) were anesthetized with Nembutal (pentobarbital sodium) (60 mg/kg body weight), a catheter was inserted into the colon through the celiotomy, and the solution of the test compound was administered through the catheter (NCG21 as a suspension in PEG at 100 mmol/g body weight, at a rate of 100 µl/min). After 15 minutes, a blood sample was taken from the portal vein, centrifuged at 8000 rpm for 10 minutes, and the supernatant was stored at −80° C. GLP-1 (ng/mL) was determined using ELISA kit (Wako Pure Chemical Industries, Ltd.) within the next day. Each group consists of 12 mice, except that 11 mice were used for NCG21.

TABLE 2

|  | DMSO | LA | NCG21 |
|---|---|---|---|
| Average* | 1.61 | 3.87 | 4.02 |
| SE | 0.30 | 0.56 | 0.69 |
| T test vs DMSO |  | 0.0017 | 0.0035 |
| T test vs NCG15 |  |  | 0.0045 |

*Average GLP-1 concentration: ng/mL

As shown in Table 2, the positive control LA (cis-α-linolenic acid) increased the GLP-1 concentration in the portal blood 2.4 times more than the control DMSO, whereas NCG21 (one compound in Example 2), which was shown to have an agonistic activity for GPR120, increased the GLP-1 concentration 2.5 times more than DMSO. This increase is significantly high as compared with that of DMSO. The results demonstrate that the agonist for GPR120 selected in vitro also activates GPR120 and induces GLP-1 release into blood in vivo.

Test Example 3

Determination of Intracellular $Ca^{2+}$ Concentration (1) In this test, The cell lines TXGPR40, TXGPR120 and GPR120/Flp-in were plated onto a collagen-coated black 96-well plate in $2 \times 10^5$ cells/well. The 96-well plates containing the cells were centrifuged and treated with Doxycycline (final concentration 10 µg/mL), incubated in a $CO_2$ incubator for 21 hours, then used for assay.

TXGPR40, TXGPR120, and GPR120/Flp-in each denote the cell line transfected with the plasmid in which human GPR40 (hGPR40) or human GPR120 (hGPR120) gene, respectively, has been incorporated into a expression vector that expresses said gene upon the treatment with Doxycycline, so that the cell is capable of a stable expression of GPR40 or GPR120 protein.

(2) The ligand used in this test includes NCP04, NCP14, NCG20, NCG21, NCG22, NCG23, NCP02, NCP03, NCP05, NCP06, NCG14, NCG17, NCG19, NCG28, NCG29, NCG30, NCG31, NCG34, NCG35, NCG37, NCG38, NCG44, NCG45, NCG46, and NCG54. Each ligand was dissolved in DMSO and adjusted to the concentration of 10 mM, then diluted with Hanks' Balanced Salt Solution (pH 7.4) containing 20 mM HEPES (referred to as FLIPR buffer hereinafter) to the final concentration of 1 to 100 µM. 1% DMSO was used as the negative control, and LA was used as the positive control.

The ligands and controls were placed in different 96-well plates from the plates for the cells.

(3) The 96-well plate containing the cells was removed from the $CO_2$ incubator. A fluorescent dye prepared in a twofold higher concentration (Ca Assay Kit Component A diluted with FLIPR Buffer) was added in 50 µL/well, then allowed to stand in the dark at room temperature for one hour.

(4) After one hour, the 96-well plate containing the cells and the 96-well plate in which ligands and controls were prepared were set on FLIPR (Fluorometric Imaging Plate Reader) for determination.

(5) Fluorometry using FLIPR was carried out at a laser output of 1.0 W for five minutes. Ten minutes after the start of the determination, the ligand (25 µL) was added dropwise to the cell plate at a rate of 50 µL/sec. The intensity of fluorescence was automatically digitized by the application program installed in the FLIPR from the image taken by the CCD camera (with exposure time of 0.40 sec). The interval of data sampling was one second for the initial one minute after the start of operation, and six seconds for the subsequent four minutes.

(6) The maximum fluorescence intensity was obtained from the data showing the change in the fluorescence intensity over time observed in each well. The maximum fluorescence intensity was plotted against ligand concentration, and $pEC_{50}$ was calculated. The ratio of the fluorescence intensity for each ligand to LA at 10 µM was calculated as the relative intensity of each ligand.

The intracellular $Ca^{2+}$ concentration was determined using hGPR40 and hGPR120. The results of the test with hGPR40 are shown in FIG. 9 and the results of the test with hGPR120 are shown in FIG. 10.

These results revealed NCG21 exhibits an outstanding agonistic activity for hGPR120. Therefore, NCG21 is expected to be effective as a preventive and therapeutic drug for diabetes that works by enhancing the secretion of insulin, as a therapeutic drug for insufficient digestion by enhancing the secretion of digestive juice, and as a preventive and therapeutic drug for obesity by suppressing an appetite.

Tables 3 and 4 below show the relative intensity and $pEC_{50}$ values relating to the intracellular $Ca^{2+}$ concentration and the results of assay of extracellular signal-regulated kinase (ERK) in Test Example 1. In these tables 3 and 4, +++ denotes a higher value than LA, ++ denotes 50 to 100% of LA, and + denotes 0 to 100% of LA.

TABLE 3

|  | $[Ca^{2+}]$/GPR40 | | $[Ca^{2+}]$/GPR120 | | $[Ca^{2+}]$/GPR120/Flp-In | | ERK/GPR40 | | ERK/GPR120 | |
|---|---|---|---|---|---|---|---|---|---|---|
|  | 10 µM (ratio vs. LA) | $pEC_{50}$ | 10 µM (ratio vs. LA) | $pEC_{50}$ | 10 µM (ratio vs. LA) | $pEC_{50}$ | 10 µm | 100 µm | 10 µm | 100 µm |
| NCG14 | 1.17 |  | 0.00 |  | 0.43 | 4.83 | ++ | − |  |  |
| NCG17 | 1.34 | 5.47 | 0.00 |  | 0.59 | 5.23 | ++ | − |  |  |
| NCG19 | 1.29 | 5.54 | 0.04 |  | 0.33 | 4.77 | ++ | − |  |  |

TABLE 3-continued

| | [Ca²⁺]/GPR40 | | [Ca²⁺]/GPR120 | | [Ca²⁺]/GPR120/Fl p-In | | ERK/GPR40 | | ERK/GPR120 | |
|---|---|---|---|---|---|---|---|---|---|---|
| | 10 µM (ratio vs. LA) | pEC₅₀ | 10 µM (ratio vs. LA) | pEC₅₀ | 10 µM (ratio vs. LA) | pEC₅₀ | 10 µm | 100 µm | 10 µm | 100 µm |
| NCG20 | 0.10 | 4.56 | 0.04 | | 0.41 | 4.90 | + | +++ | + | +++ |
| NCG21 | 0.26 | 4.73 | 1.90 | 5.54 | 1.04 | 5.90 | + | ++ | +++ | +++ |
| NCG22 | 0.30 | 4.69 | 0.02 | | 0.14 | 4.72 | + | ++ | ++ | ++ |
| NCG23 | 0.99 | 5.11 | 0.02 | | 0.58 | 5.04 | ++ | +++ | ++ | ++ |
| NCP02 | 1.47 | 5.47 | 0.00 | | 0.45 | 4.81 | + | +++ | + | + |
| NCP03 | 1.25 | 5.28 | 0.00 | | 0.57 | 4.75 | ++ | +++ | + | ++ |
| NCP04 | 2.15 | 5.59 | 0.00 | | 0.33 | 4.74 | +++ | +++ | + | +++ |
| NCP05 | 1.22 | 5.25 | 0.00 | | 0.45 | 4.94 | +++ | +++ | + | +++ |
| NCP14 | 0.98 | 5.01 | 0.00 | | 0.56 | 4.81 | ++ | ++ | − | ++ |
| NCG28 | 1.37 | 5.95 | 0.02 | | 0.54 | 5.17 | +++ | +++ | ++ | +++ |

TABLE 4

| | [Ca²⁺]/GPR40 | | [Ca²⁺]/GPR120 | | [Ca²⁺]/GPR120/Fl p-In | | ERK/GPR40 | | ERK/GPR120 | |
|---|---|---|---|---|---|---|---|---|---|---|
| | 10 µM (ratio vs. LA) | pEC₅₀ | 10 µM (ratio vs. LA) | pEC₅₀ | 10 µM (ratio vs. LA) | pEC₅₀ | 10 uM | 100 uM | 10 uM | 100 uM |
| NCG29 | 0.21 | 4.68 | 0.85 | 4.92 | 0.88 | 5.37 | ++ | +++ | +++ | +++ |
| NCG30 | 0.01 | | 0.71 | 4.81 | 0.88 | 5.43 | − | + | ++ | +++ |
| NCG31 | 0.32 | 4.72 | 0.61 | 4.77 | 0.73 | 5.16 | +++ | +++ | +++ | +++ |
| NCG34 | 0.43 | 4.65 | 0.49 | 4.54 | 0.81 | 5.16 | + | +++ | +++ | +++ |
| NCG35 | 0.68 | 5.11 | 0.61 | 4.79 | 1.00 | 5.34 | +++ | +++ | +++ | +++ |
| NCG37 | 0.28 | 4.79 | 0.56 | 4.75 | 0.91 | 5.46 | − | + | +++ | +++ |
| NCG38 | 0.34 | 4.87 | 0.56 | 4.65 | 0.81 | 5.17 | ++ | +++ | +++ | +++ |
| NCG44 | 0.01 | | 0.49 | 4.64 | 0.85 | 5.45 | − | + | + | ++ |
| NCG45 | 0.01 | | 0.01 | | 0.65 | 5.00 | − | − | + | ++ |
| NCG46 | 0.30 | 4.67 | 1.60 | 5.28 | 1.06 | 5.78 | − | ++ | +++ | +++ |
| NCG54 | 0.07 | 4.62 | 0.66 | 4.80 | 0.92 | 5.62 | + | ++ | +++ | +++ |

It was found that NCG14, NCG17, and NCG19 are selective agonists for GPR40, whereas the other compounds are effective as agonists for both GPR120 and GPR40.

As mentioned above, in the case of hGPR120, NCG21 as well as the other compounds NCP02, NCP03, NCP04, NCP05, NCP06, NCP14, NCG14, NCG17, NCG19, NCG20, NCG22, NCG23, NCG28, NCG29, NCG30, NCG31, NCG34, NCG35, NCG37, NCG38, NCG44, NCG45, NCG46, and NCG54 are found to exhibit a similar effect in the cell in which GPR120 has been transgenically expressed. Therefore, these compounds are useful as agonistic agents (agonists) for GPR120.

Similarly, in the case of hGPR40, the compounds of the present invention NCP02, NCP03, NCP04, NCP05, NCP14, NCG14, NCG17, NCG19, NCG20, NCG21, NCG22, NCG23, NCG28, NCG29, NCG31, NCG34, NCG35, NCG38, NCG46, and NCG54 showed a specific reactivity to the cell in which GPR40 has been transgenically expressed. Therefore, these compounds are useful as agonistic agents (agonists) for GPR40.

NCG21, NCG30, NCG37, NCG46, and NCG54 exhibit agonistic activity for both GPR40 and GPR120, although their agonistic activity is selective, acting relatively mildly for GPR40 but acting strongly for GPR120. All of other compounds activate both GPR120 and GPR40.

As described in Nature Medicine, 11(1), 90-94, 2005 and Japanese Patent Application published as JP, A, 2005-15358, a GPR120 agonist promotes the release of GLP-1 or CCK from GPR120-expressing cells. A GPR120 agonist is useful for a coordinated promotion of digestive activity, as a therapeutic for digestion disorder, as a prophylactic or therapeutic for obesity by suppressing an appetite, as a therapeutic for hyperphagia, as a prophylactic or therapeutic for diabetes by enhancing differentiation and proliferation of pancreatic β cells, particularly for improving therapeutic effects in engrafting of β cells or precursor cells thereof, for improving therapeutic effects in nerve engrafting and nerve suturing by maintaining the plasticity and survival of nerve cells, or as a therapeutic for diseases resulting from neurological disorder such as Alzheimer disease which, as a therapeutic for anomalous bowel motility due to enteritis by normalizing bowel motility, and as a therapeutic for lung diseases such as COPD (chronic obstructive pulmonary disease) by accelerating the secretion of surfactants in lung, as also apparent from the following articles:

(i) As an agent for coordinated promotion of digestive activity, and as a therapeutic drug for digestion disorder;
Nutrition 2001; 17(3): 230-5, Best Pract Res Clin Endocrinol Metab 2004; 18(4): 569-86, Dig Dis Sci. 2004; 49(3): 361-9, Endocrinology 2004; 145(6); 2653-9, Pharmacol Toxicol 2002; 91(6): 375-81, Gastroenterology 2004; 127 (3): 957-69, Best Pract Res Clin Endocrinol Metab 2004; 18(4): 569-86, Med Res Rev. 2003; 23(5): 559-605, Med Res Rev. 2003; 23(5): 559-605, Horm Metab Res 2004;

36(11-12): 842-5, Horm Metab Res 2004; 36(11-12); 842-5, Am J Phyusiol Endocrinol Metab 2004; 287(6): E1209-15, Dig Dis Sci 1998; 43(4): 799-805, (ii) As a prophylactic or therapeutic for obesity by suppressing appetite, and as a therapeutic drug for hyperphagia;
Physiol Behav. 2004; 83(4): 617-21, Best Pract Res Cli Endocrinol Metab. 2004; 18(4): 569-86, Trends Endocrinol Metab. 2004; 15(6): 259-63, Curr Drug Target CNS Neurol disord 2004; 3(5): 379-88

(iii) As a prophylactic or therapeutic for diabetes by enhancing differentiation and proliferation of pancreatic β cells, particularly as an agent to enhance therapeutic effect in engrafting of β cells or precursor cells thereof;
Diabetology, 2005; 48(9); 1700-13, Diabetes 2004; 53 suppl 3:S225-32, Hormone Metab Res. 2004 (11-12): 766-70, Hormone Metab Res. 2004, 36(11-12): 846-51

(iv) As an agent to accelerate the effect of treatment in nerve grafting and nerve suturing by maintaining the flexibility and survival of nerve cells, or as a therapeutic drug for diseases resulting from neurological disorder such as Alzheimer disease;
Curr Drug Target CNS Neurol Disord 2002; 1(5): 495-510, Curr Drug Targets. 2004; 5(69:565-71), Curr Alzheimer Res 2005, 2(3): 377-85

(v) As a therapeutic for anomalous bowel motility due to enteritis by normalizing bowel motility;
Drug 2003; 63(12): 1785-97, Br J Pharmacol. 2004; 141(8): 1275-84, (vi) As a therapeutic for lung disease such as COPD (chronic obstructive pulmonary disease) by accelerating the secretion of surfactants;
Endocrinology. 1998; 139(5): 2363-8. Am J Respir Crit Care Med. 2001; 163(4): 840-6.

The invention claimed is:

1. A method for activating GPCR120 in an animal, said method comprising administering to the animal an agonist for GPCR120, wherein the agonist comprises as an active ingredient an aralkylcarboxylic acid compound represented by the general formula (I):

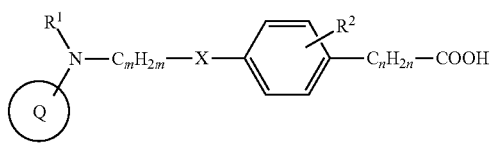

wherein:
the ring Q is a phenyl group, a pyridyl group wherein said pyridyl group may be substituted with one or two substituents selected from the group consisting of a halogen atom, a $C_{1-4}$ alkyl and a $C_{1-4}$ alkoxy group, or a thiazolyl group which may be condensed with a benzene ring,
$R^1$ is a phenyl wherein said phenyl may be substituted with an amino group,
$R^2$ is a hydrogen atom,
X is an oxygen atom, and
m is an integral number of 2, and n is an integral number of 3
or a pharmaceutically acceptable salt thereof.

2. A method for treating or preventing a disease associated with GPCR120 in a patient in need thereof, said method comprising administering to the patient an agonist for GPCR120, wherein the agonist comprises as an active ingredient an aralkylcarboxylic acid compound represented by the general formula (I):

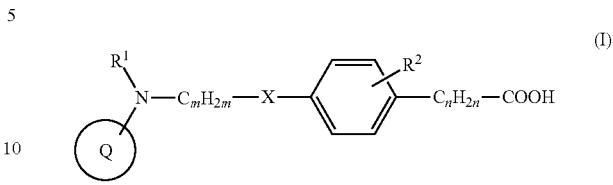

wherein:
the ring Q is a phenyl group, a pyridyl group wherein said pyridyl group may be substituted with one or two substituents selected from the group consisting of a halogen atom, a $C_{1-4}$ alkyl and a $C_{1-4}$ alkoxy group, or a thiazolyl group which may be condensed with a benzene ring,
$R^1$ is a phenyl wherein said phenyl may be substituted with an amino group,
$R^2$ is a hydrogen atom,
X is an oxygen atom, and
m is an integral number of 2, and n is an integral number of 3
or a pharmaceutically acceptable salt thereof.

3. The method of claim 2 wherein the patient is administered a pharmaceutical composition comprising the agonist for GPCR120.

4. A method for activating GPCR120 in an animal according to claim 1, wherein the activating GPCR120 is to suppress an appetite, to enhance differentiation and proliferation of pancreatic beta cells, or to treat and/or prevent obesity by suppressing an appetite, diabetes by enhancing insulin secretion, metabolic syndrome, digestive organ disease, neurological disorder, psychological disorder, lung disease, or pituitary hormone secretion incompetence.

5. The method for treating or preventing a disease associated with GPCR120 according to claim 2, wherein the pharmaceutical composition is an appetite suppressant, an obesity inhibitor suppressing an appetite, a therapeutic drug enhancing insulin secretion for diabetes, a differentiation and proliferation enhancer of pancreatic beta cells, a therapeutic drug for metabolic syndrome, a therapeutic drug for digestive organ disease, a therapeutic drug for neurological disorder, a therapeutic drug for psychological disorder, a therapeutic drug for lung disease, or a therapeutic drug for pituitary hormone secretion incompetence.

6. The method for activating GPCR120 in an animal according to claim 1, wherein the active ingredient is an aralkylcarboxylic acid compound selected from the following group:

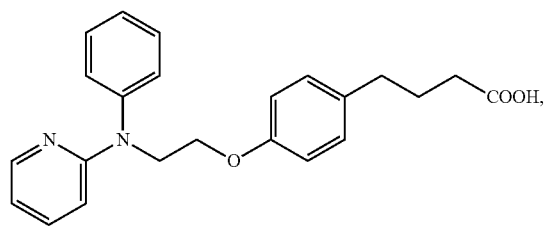

NCG21

NCG29
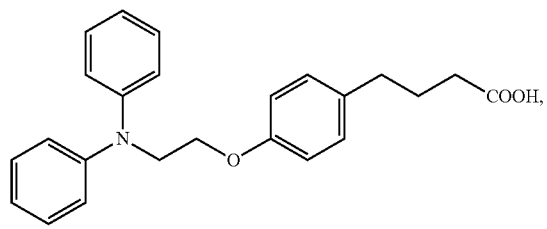
NCG38
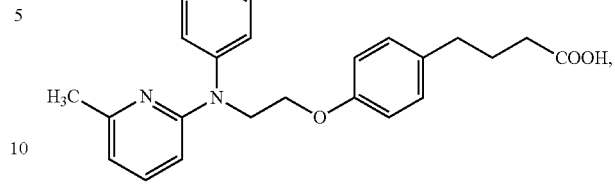
NCG30
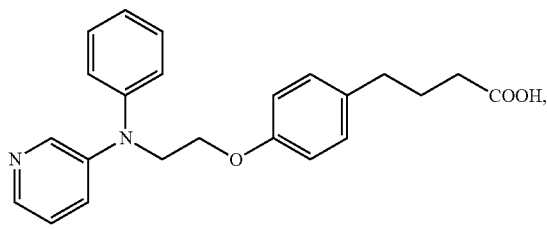
NCG46
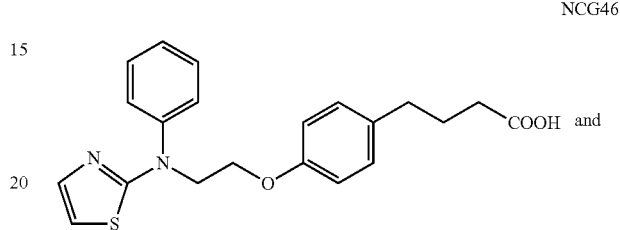
NCG31
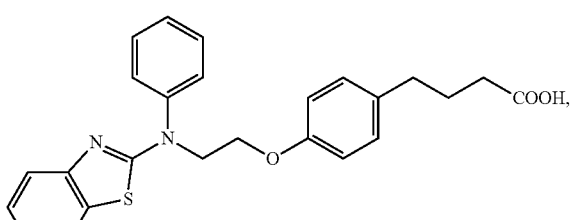
NCG54
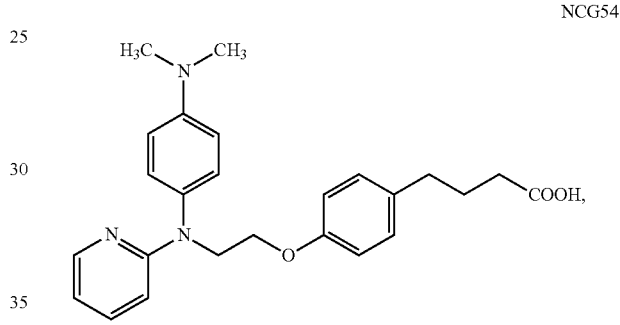
or a pharmaceutically acceptable salt thereof.
7. The method for activating GPCR120 in an animal according to claim 6, wherein the active ingredient is NCG21, NCG30, NCG37, NCG46 or NCG54 below:
NCG34
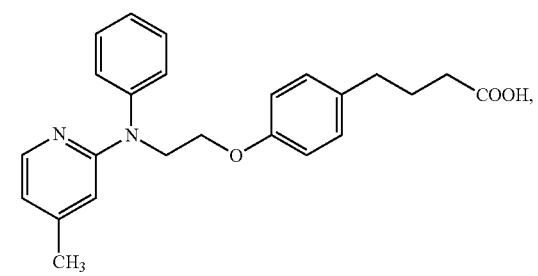
NCG35
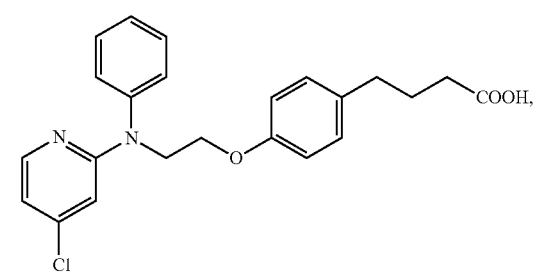
NCG37
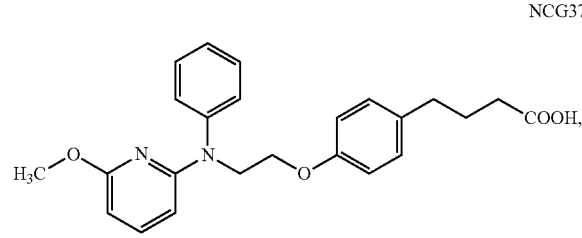
NCG21
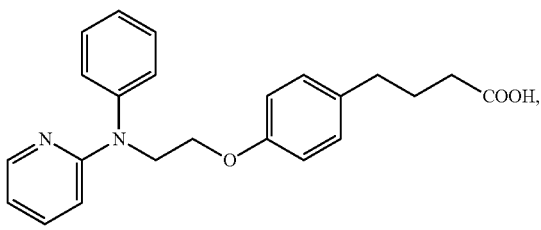
NCG30
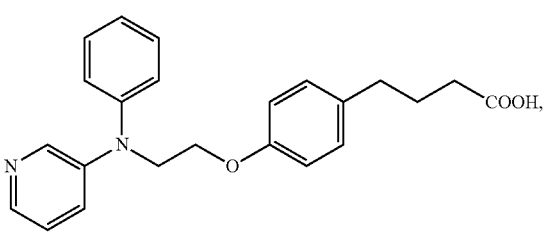

-continued

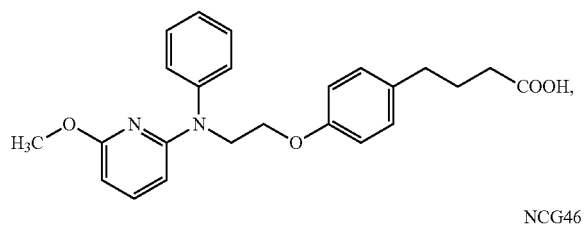
NCG37

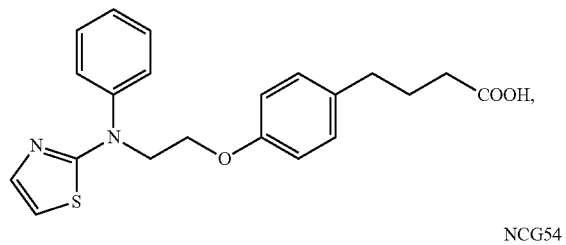
NCG46

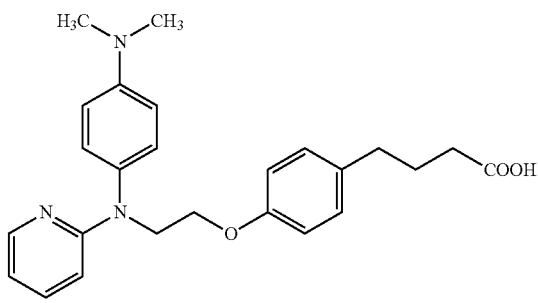
NCG54 or a pharmaceutically acceptable salt thereof.

8. The method for activating GPCR120 in an animal according to claim 7, wherein the active ingredient is NCG21 or NCG46 below:

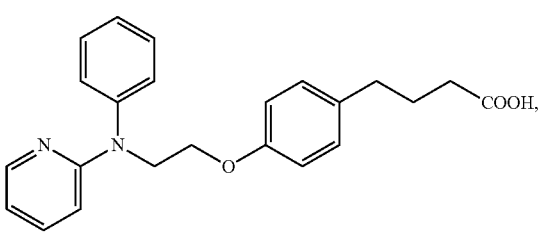
NCG21

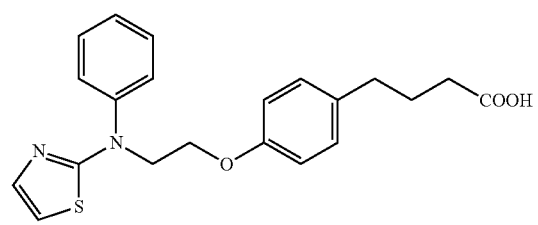
NCG46 or a pharmaceutically acceptable salt thereof.

9. The method for treating or preventing a disease associated with GPCR120 according to claim 2, wherein the active ingredient is an aralkylcarboxylic acid compound selected from the following group:

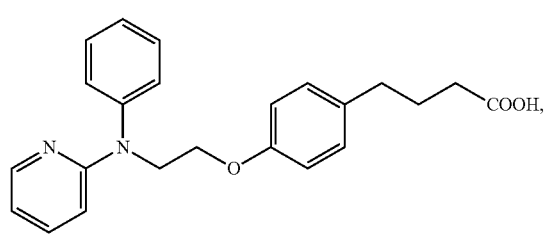
NCG21

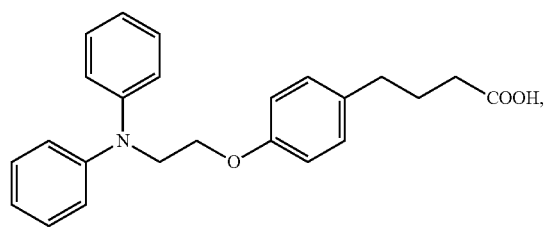
NCG29

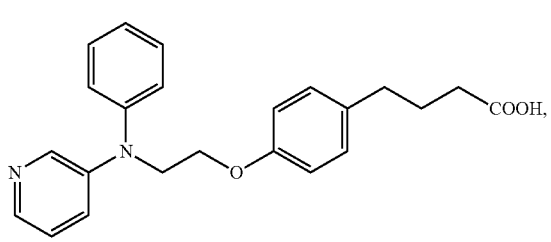
NCG30

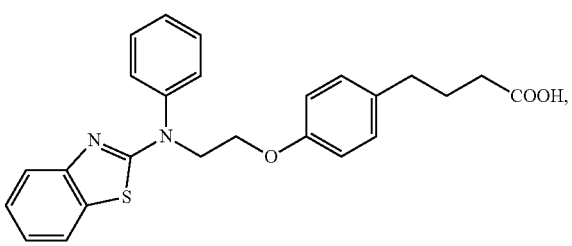
NCG31

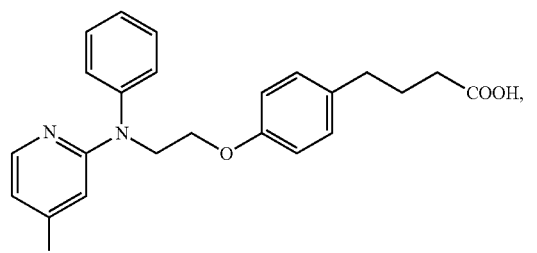
NCG34

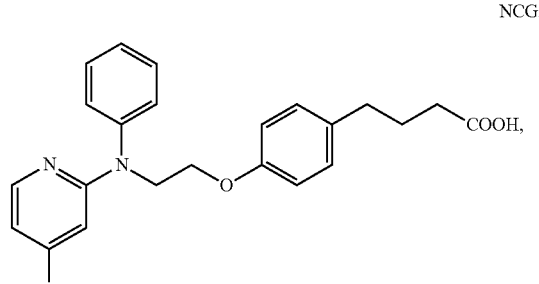
NCG35

NCG37

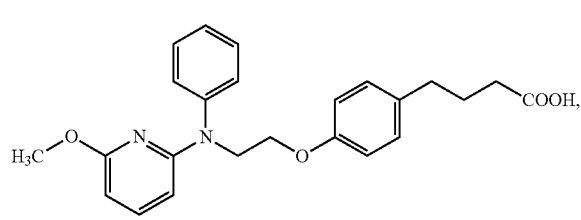

NCG38

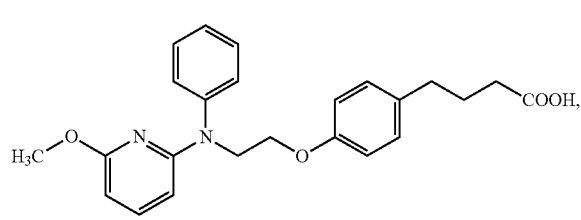

NCG46

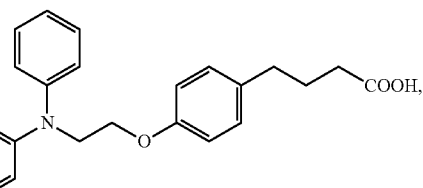

and

NCG54

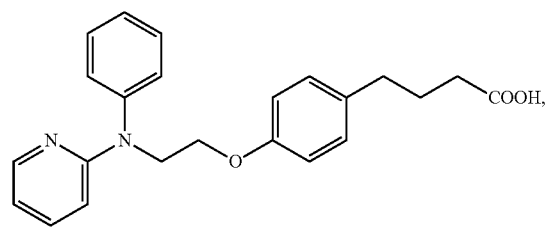

or a pharmaceutically acceptable salt thereof.

10. The method for treating or preventing a disease associated with GPCR120 according to claim 9, wherein the active ingredient is NCG21, NCG30, NCG37, NCG46 or NCG54 below:

NCG21

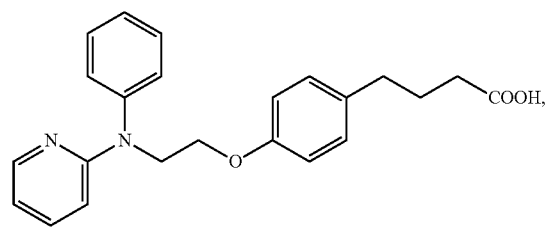

NCG30

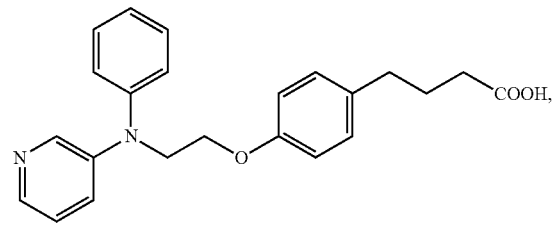

NCG37

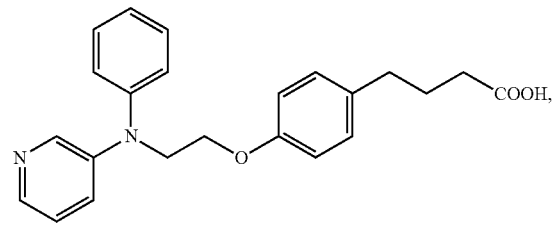

NCG46

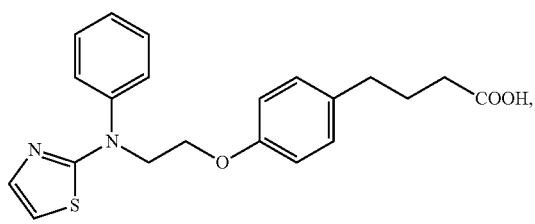

NCG54

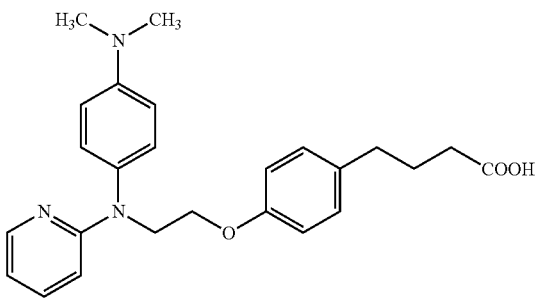

or a pharmaceutically acceptable salt thereof.

11. The method for treating or preventing a disease associated with GPCR120 according to claim 10, wherein the active ingredient is NCG21 or NCG46 below:

NCG21

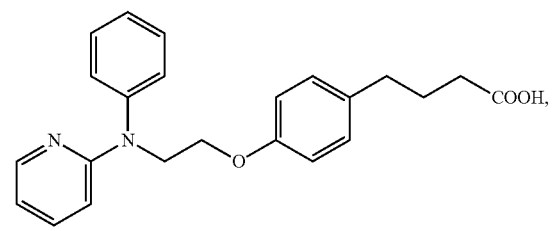

-continued

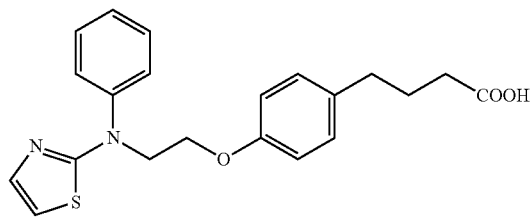

NCG46 or a pharmaceutically acceptable salt thereof.

12. The method for treating or preventing a disease associated with GPCR120 according to claim 3, wherein the pharmaceutical composition is administered intravenously, orally, transmucosally, or transdermally.

13. The method for treating or preventing a disease associated with GPCR120 according to claim 3, wherein the pharmaceutical composition is administered transmucosally.

14. The method for treating or preventing a disease associated with GPCR120 according to claim 3, wherein the pharmaceutical composition is administered by rectal delivery.

15. The method for treating or preventing a disease associated with GPCR120 according to claim 3, wherein the pharmaceutical composition is prepared in the form of suppository or retention enema.

* * * * *